(12) United States Patent
Bae et al.

(10) Patent No.: US 10,103,335 B2
(45) Date of Patent: Oct. 16, 2018

(54) MATERIAL FOR ORGANIC LIGHT EMITTING DEVICE, ORGANIC LIGHT EMITTING DEVICE, AND DISPLAY DEVICE INCLUDING THE SAME

(71) Applicant: SAMSUNG DISPLAY CO., LTD., Yongin, Gyeonggi-Do (KR)

(72) Inventors: Sung-Soo Bae, Seoul (KR); Jung Sub Lee, Bucheon-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 523 days.

(21) Appl. No.: 14/670,378

(22) Filed: Mar. 26, 2015

(65) Prior Publication Data

US 2015/0295185 A1    Oct. 15, 2015

(30) Foreign Application Priority Data

Apr. 14, 2014 (KR) .................. 10-2014-0044460

(51) Int. Cl.
*H01L 51/00* (2006.01)
*C07D 403/04* (2006.01)
*C07D 495/04* (2006.01)
*C07F 7/08* (2006.01)

(52) U.S. Cl.
CPC ........ *H01L 51/0067* (2013.01); *C07D 403/04* (2013.01); *C07D 495/04* (2013.01); *C07F 7/0809* (2013.01); *C07F 7/0812* (2013.01); *H01L 51/0071* (2013.01);
(Continued)

(58) Field of Classification Search
CPC .................. H01L 51/0069; C07D 403/04
See application file for complete search history.

(56) References Cited

U.S. PATENT DOCUMENTS

| 2005/0181233 A1 | 8/2005 | Sohn et al. |
| 2006/0227081 A1 | 10/2006 | Joo et al. |
| 2008/0124455 A1 | 5/2008 | Shin et al. |

(Continued)

FOREIGN PATENT DOCUMENTS

| JP | 2001-160488 | 6/2001 |
| JP | 2009-76835 | 4/2009 |

(Continued)

OTHER PUBLICATIONS

U.S. Office action dated Nov. 19, 2015, for cross reference U.S. Appl. No. 13/633,707, (14 pages).

(Continued)

*Primary Examiner* — Kuo Liang Peng
(74) *Attorney, Agent, or Firm* — Lewis Roca Rothgerber Christie LLP

(57) ABSTRACT

A material for an organic light emitting device includes a compound represented by one of the following Chemical Formulae 1 to 3 and a compound represented by the following Chemical Formula 4.

In the above Chemical Formulae 1 to 4, each substituent is the same as defined in the detailed description.

11 Claims, 2 Drawing Sheets

(52) U.S. Cl.
CPC ...... *H01L 51/0072* (2013.01); *H01L 51/0073* (2013.01); *H01L 51/0074* (2013.01); *H01L 51/0094* (2013.01)

(56) References Cited

U.S. PATENT DOCUMENTS

| | | | |
|---|---|---|---|
| 2010/0013381 | A1 | 1/2010 | Stoessel et al. |
| 2010/0066243 | A1 | 3/2010 | Igarashi et al. |
| 2010/0230660 | A1 | 9/2010 | Yokoyama et al. |
| 2011/0057175 | A1 | 3/2011 | Kim et al. |
| 2011/0084259 | A1 | 4/2011 | Lee et al. |
| 2011/0156014 | A1 | 6/2011 | Kim et al. |
| 2011/0297919 | A1 | 12/2011 | Kwak et al. |
| 2011/0309348 | A1 | 12/2011 | Kwak et al. |
| 2012/0181518 | A1 | 7/2012 | Ogiwara et al. |
| 2013/0200339 | A1 | 8/2013 | Lee et al. |
| 2014/0001443 | A1 | 1/2014 | Lee et al. |
| 2014/0319485 | A1 | 10/2014 | Lee |
| 2015/0041770 | A1* | 2/2015 | Lee .................. H01L 51/0067 257/40 |

FOREIGN PATENT DOCUMENTS

| | | |
|---|---|---|
| JP | 2011-57672 A | 3/2011 |
| JP | 2011-178742 | 9/2011 |
| JP | 2011-210873 | 10/2011 |
| JP | 2011-251962 A | 12/2011 |
| JP | 2012-1538 A | 1/2012 |
| JP | 2012-156499 | 8/2012 |
| KR | 10-2005-0079727 | 8/2005 |
| KR | 10-2010-0024340 | 3/2010 |
| KR | 10-2010-0129101 A | 12/2010 |
| KR | 10-2011-0068330 | 6/2011 |
| KR | 10-2011-0137712 A | 12/2011 |
| KR | 10-2012-0021215 | 3/2012 |
| KR | 10-2012-0052879 | 5/2012 |
| KR | 2012-0092910 | 8/2012 |
| KR | 10-2013-0091542 | 8/2013 |
| KR | 10-2014-0003259 | 1/2014 |
| WO | WO 2008/020611 A1 | 2/2008 |
| WO | WO 2012/067425 | 5/2012 |

OTHER PUBLICATIONS

U.S. Notice of Allowance dated Sep. 29, 2015, for cross reference U.S. Appl. No. 14/203,457 (now U.S. Pat. No. 9,257,656), (16 pages).
Treibs, W., Jerusalem Symposia on Quantum Chemistry and Biochemistry, (1971), STN abstract, (1 page).
STN-Registry CAS:205-57-2, Nov. 16, 1984, (3 pages).
SIPO Office action dated Jan. 13, 2016, with English translation, for Chinese Patent application 201210579965.1, (11 pages).
English machine translation of Japanese Publication 2001-160488 dated Jun. 12, 2001, listed above, (12 pages).
English machine translation of Japanese Publication 2011-178742 dated Sep. 15, 2011, listed above, (33 pages).
English machine translation of Korean Publication 10-2012-0092910 dated Aug. 22, 2011, listed above, (26 pages).

* cited by examiner

US 10,103,335 B2

MATERIAL FOR ORGANIC LIGHT EMITTING DEVICE, ORGANIC LIGHT EMITTING DEVICE, AND DISPLAY DEVICE INCLUDING THE SAME

CROSS-REFERENCE TO RELATED APPLICATION

This application claims priority to and the benefit of Korean Patent Application No. 10-2014-0044460, filed in the Korean Intellectual Property Office on Apr. 14, 2014, the entire content of which is incorporated herein by reference.

BACKGROUND

1. Field

A material for an organic light emitting device, an organic light emitting device and a display device including the same are disclosed.

2. Description of the Related Art

Since an organic light emitting device has light emitting characteristics and does not require a separate light source (unlike a liquid crystal display (LCD)), the thickness and the weight may be reduced.

Further, since an organic light emitting device exhibits high definition characteristics such as low power consumption, high luminance, high response speed, or the like, it has been spotlighted as the next generation display device for portable electronic devices.

An organic light emitting device includes a plurality of organic light emitting diodes having a hole injection electrode, an organic emission layer, and an electron injection electrode.

In the organic emission layer, light emitting is achieved by the energy generated when exitons produced by the combination of electrons and holes drop from the exited state to the ground state, and the organic light emitting device forms an image therewith.

SUMMARY

An aspect according to one or more embodiments of the present invention, is directed toward a material for an organic light emitting device having high efficiency and long life-span.

According to one embodiment, a material for an organic light emitting device includes a compound represented by one of the following Chemical Formulae 1 to 3 and a compound represented by the following Chemical Formula 4.

Chemical Formula 1

Chemical Formula 2

Chemical Formula 3

In the above Chemical Formulae 1 to 3, $L_1$ to $L_4$ are each independently a single bond, a substituted or unsubstituted C6 to C30 arylene group, a substituted or unsubstituted C3 to C30 heteroarylene group, or a combination thereof;

$R_1$ to $R_4$ are each independently hydrogen, deuterium, a substituted or unsubstituted C1 to C30 alkyl group, a substituted or unsubstituted C1 to C30 haloalkyl group, a halogen, a cyano group, a substituted or unsubstituted C3 to C30 cycloalkyl group, a substituted or unsubstituted C5 to C7 heterocycloalkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C1 to C30 alkoxy group, a substituted or unsubstituted C6 to C30 aryloxy group, a substituted or unsubstituted C3 to C30 heteroaryl group, a nitro group, —P(=O)$R_aR_b$, —P(=S)$R_aR_b$, a hydroxyl group, or a combination thereof, wherein $R_a$ and $R_b$ are each independently a substituted or unsubstituted C6 to C30 aryl group, a substituted or unsubstituted C3 to C30 heteroaryl group, or a combination thereof; and X is N, S or O.

When X=N, *-$L_4$-$R_4$ is not hydrogen.

Chemical Formula 4

In the above Chemical Formula 4, $R_1$ to $R_5$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxyl group, a carboxyl group, or a combination thereof;

A is C, N, O or S; B is N, O or S;

C and D are each independently N or C;

L is a single bond, a substituted or unsubstituted C6 to C40 arylene group, or a substituted or unsubstituted C3 to C40 heteroarylene group;

Ar is a substituted or unsubstituted C6 to C40 aryl group, a substituted or unsubstituted C5 to C40 heterocycloalkyl group, a substituted or unsubstituted C3 to C40 heteroaryl group, or a combination thereof.

In the above Chemical Formulae 1 to 3, $L_1$ to $L_4$ may be each independently a substituted or unsubstituted C3 to C30 heteroarylene group; and $R_1$ to $R_4$ may be each independently a substituted or unsubstituted C5 to C7 heterocycloalkyl group, a substituted or unsubstituted C3 to C30 heteroaryl group, or a combination thereof, wherein the heteroarylene group, heterocycloalkyl group and heteroaryl group each independently includes at least one heteroatom selected from B, N, O, S, P and Si.

In the above Chemical Formula 4, Ar may be phenyl, biphenyl, terphenyl, naphthyl, anthracenyl, phenanthryl, pyrenyl, fluorenyl, carbazolyl, N-carbazolephenyl, quinolinyl, isoquinolinyl, or a combination thereof.

The compound represented by one of the above Chemical Formulae 1 to 3 may be one selected from the following chemical structures 1 to 68 of Group 1.

Group 1

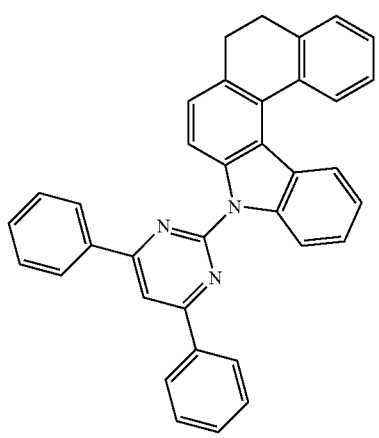

1

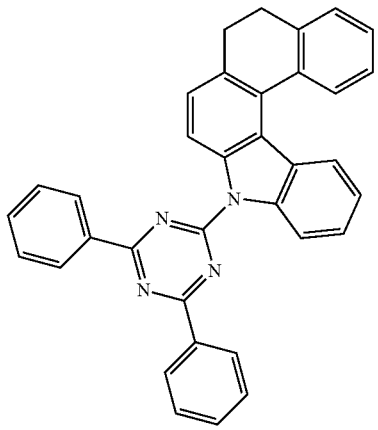

2

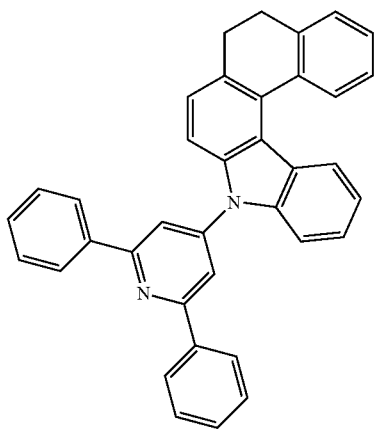

3

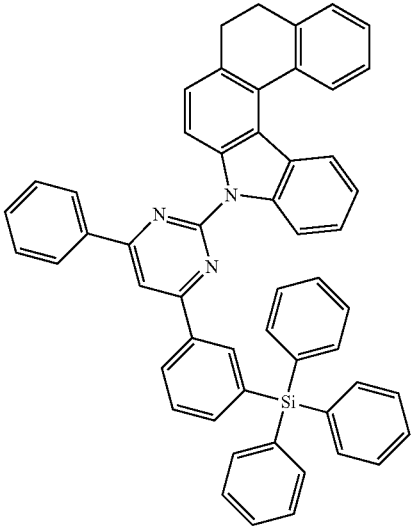

4

5
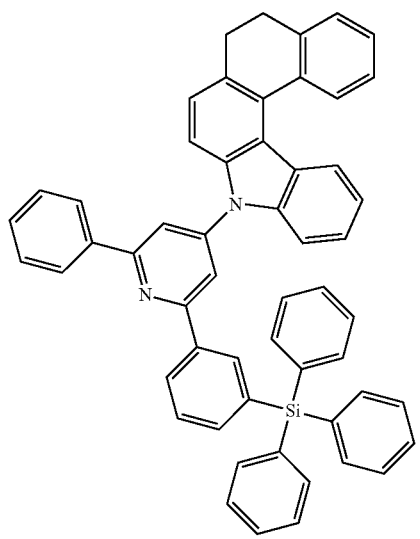
6
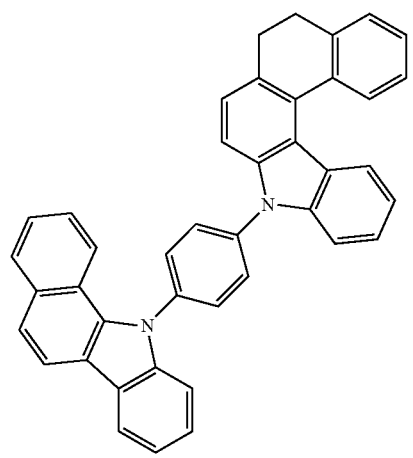
7
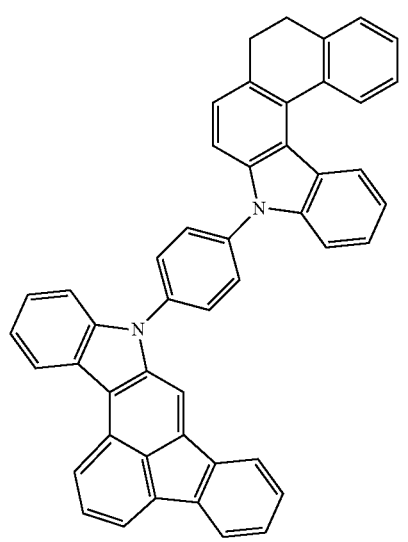
8
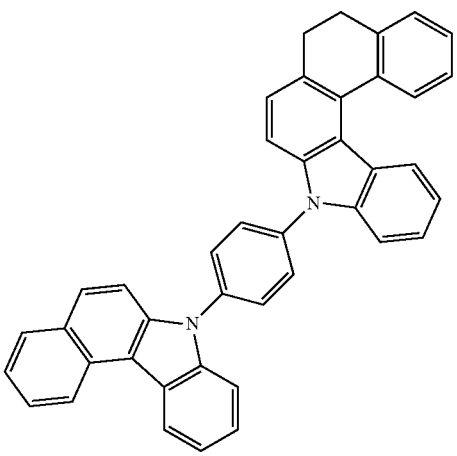
9
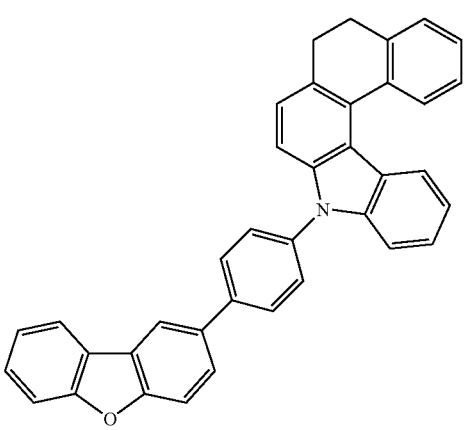
10
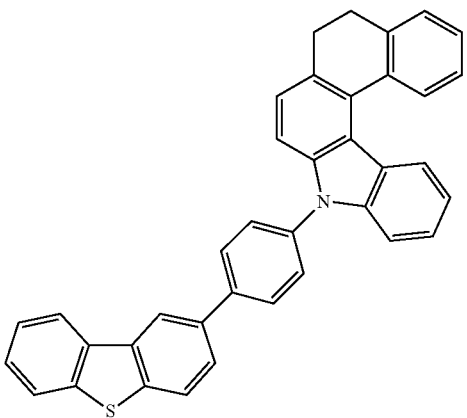

-continued
11
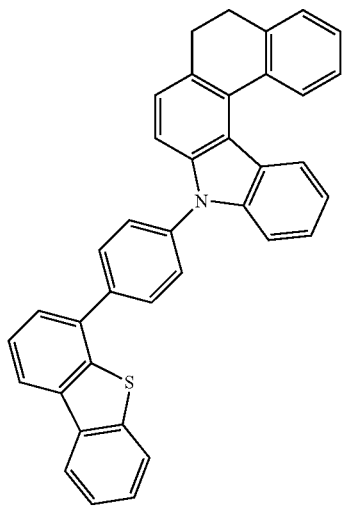
14
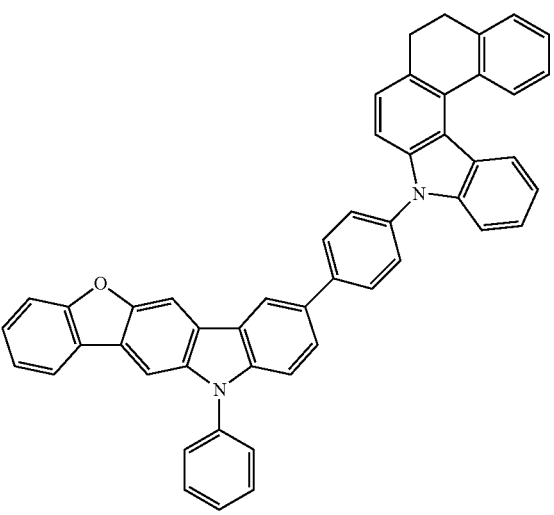
12
13
15
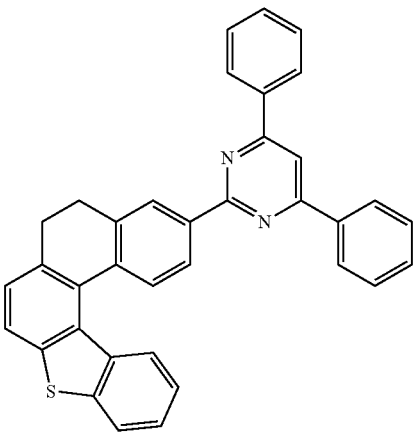
16
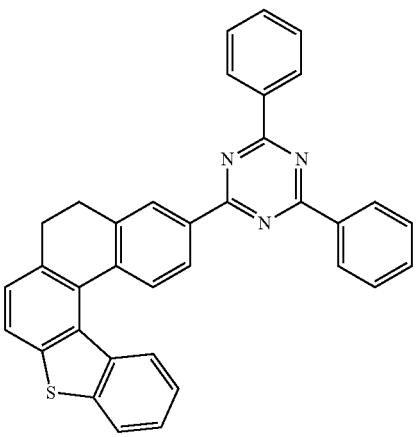

17
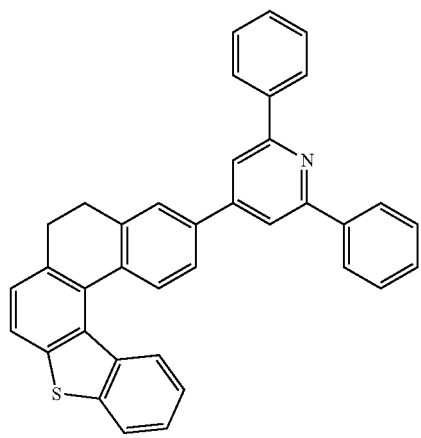
18
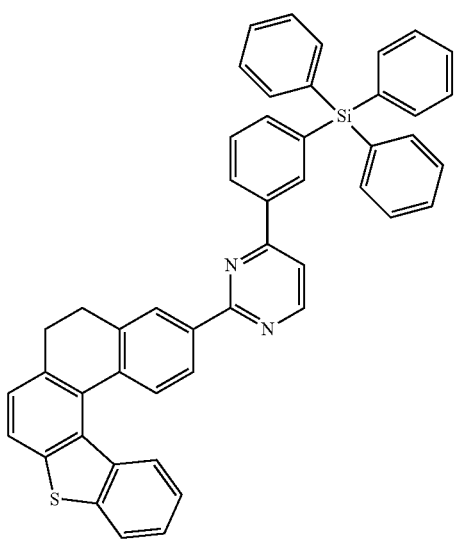
19
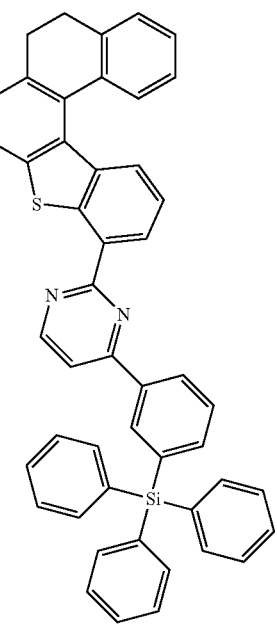
20
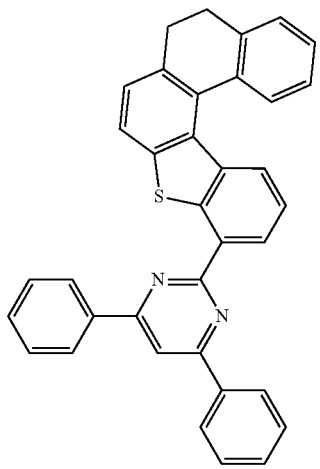
21
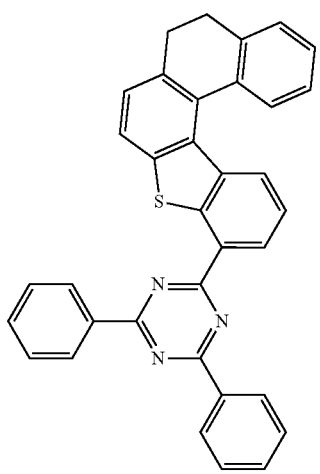
22
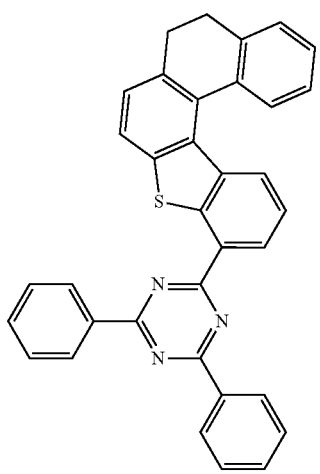

23
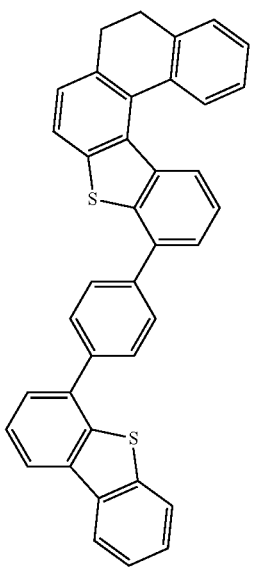
24
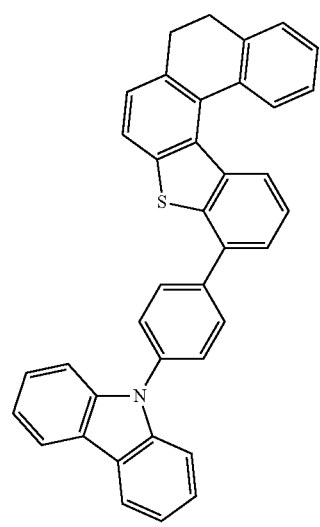
25
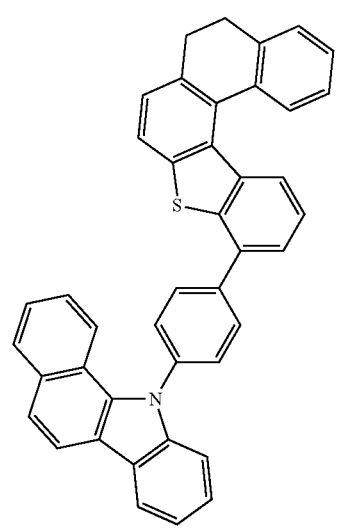
26
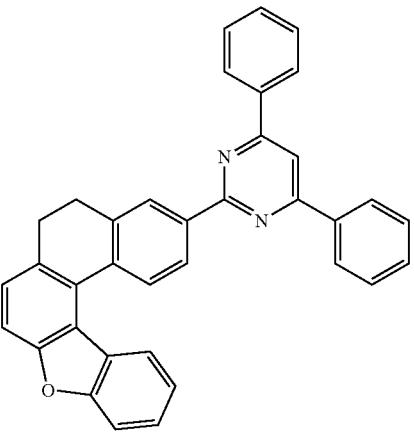
27
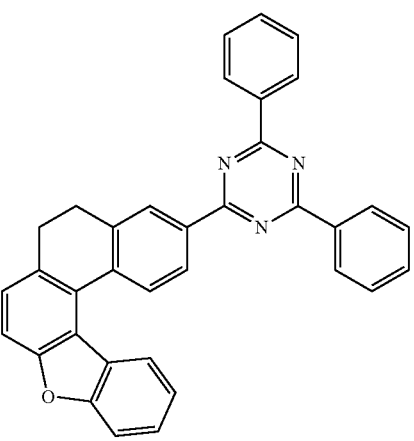
28
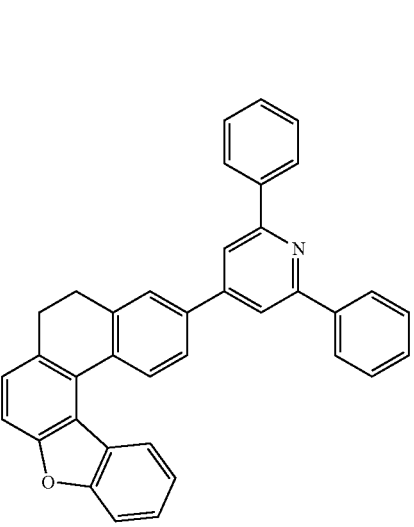

-continued
29
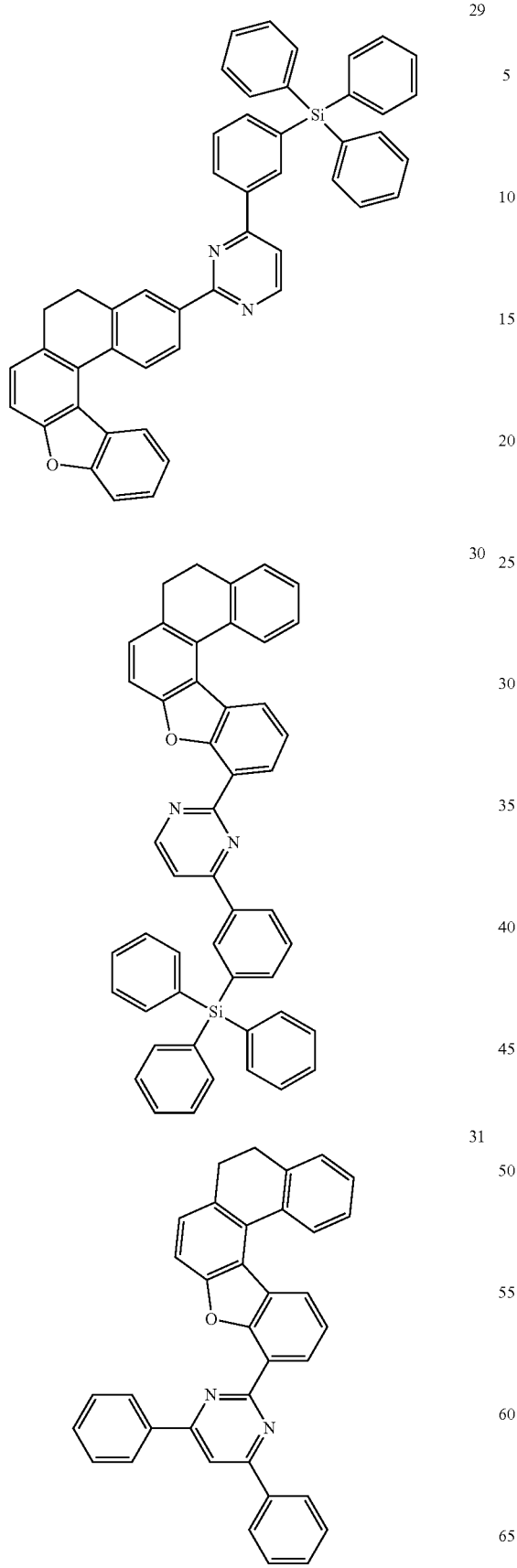
30
31
32
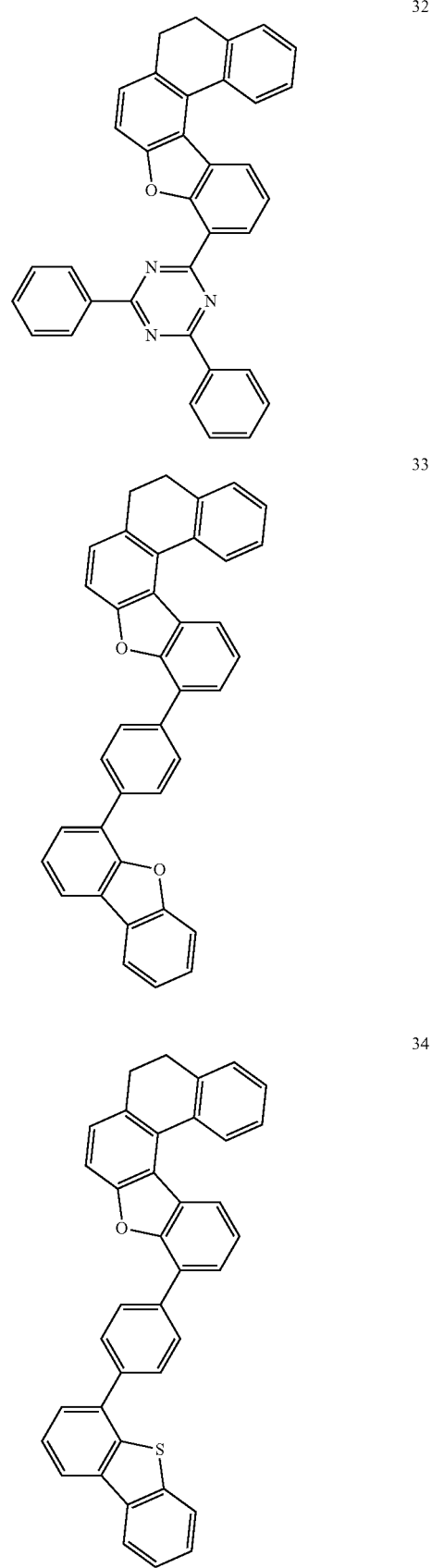
33
34

35
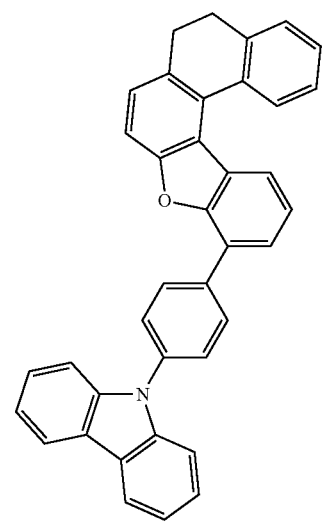
36
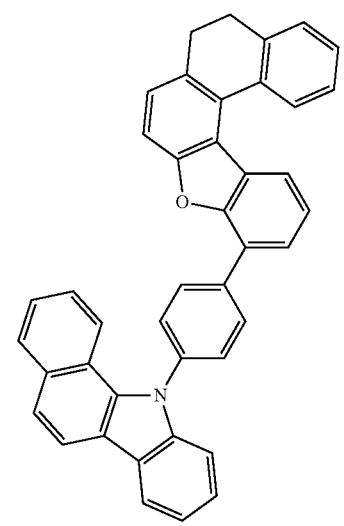
37
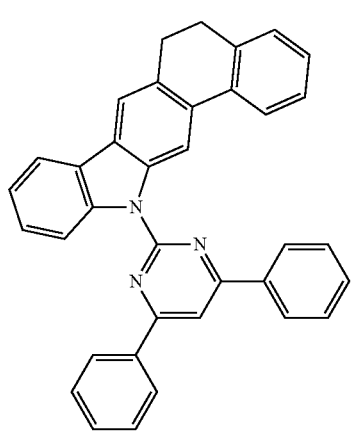
38
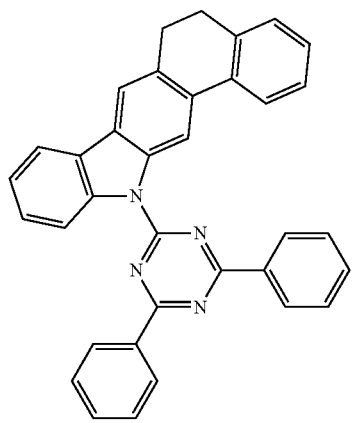
39
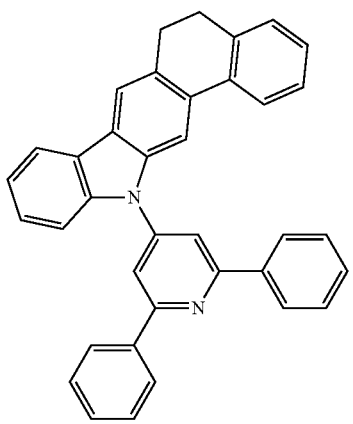
40
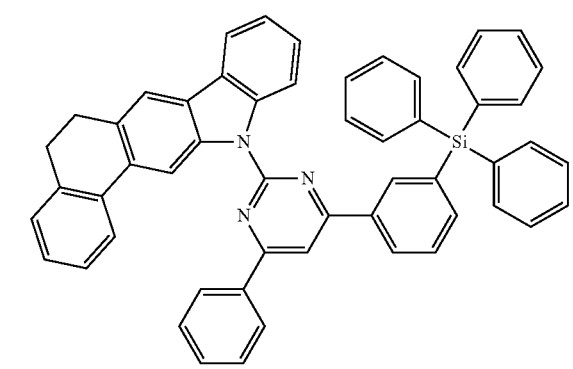
41
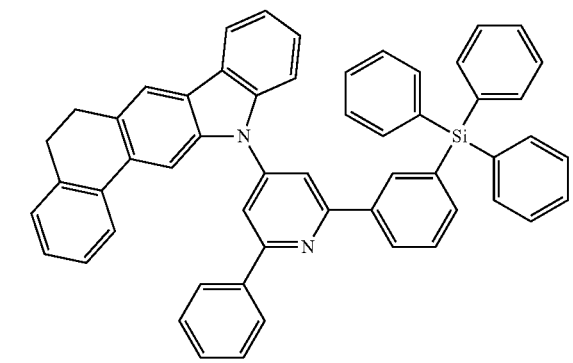

42
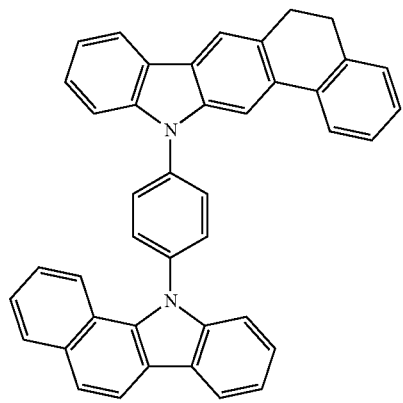
43
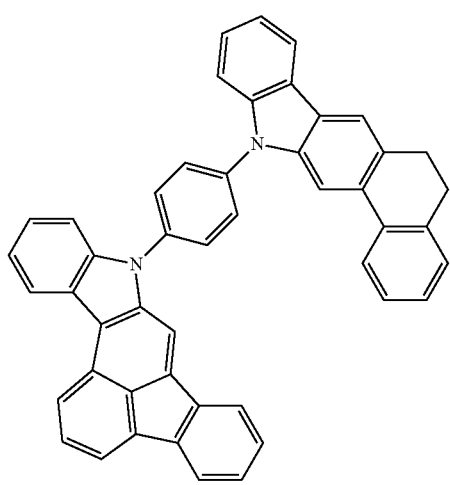
45
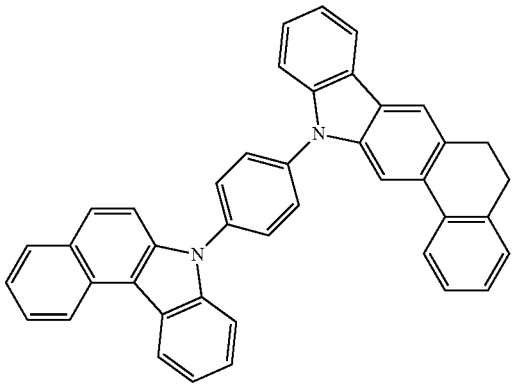
46
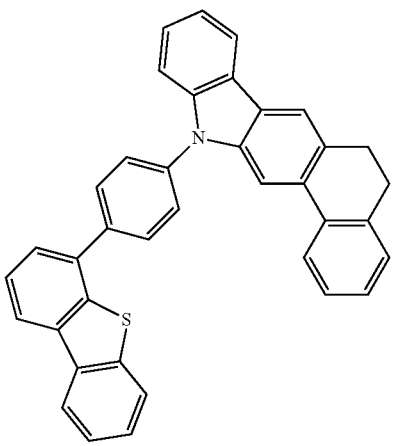
47

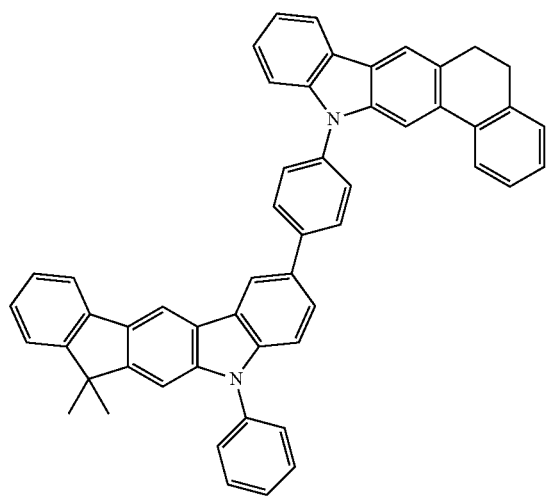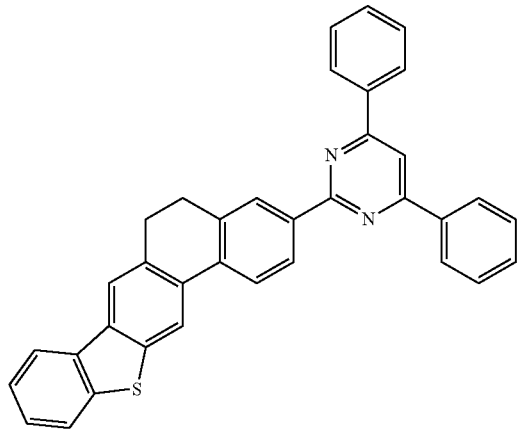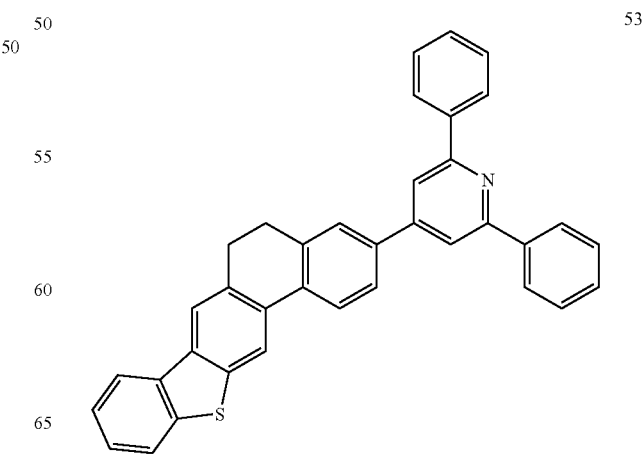

54
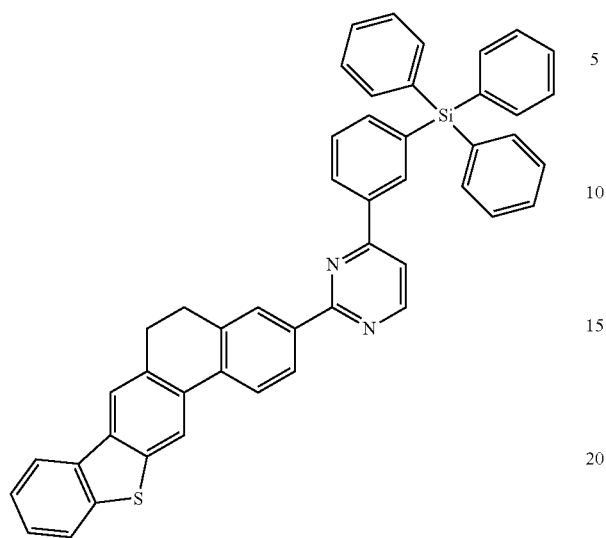
55
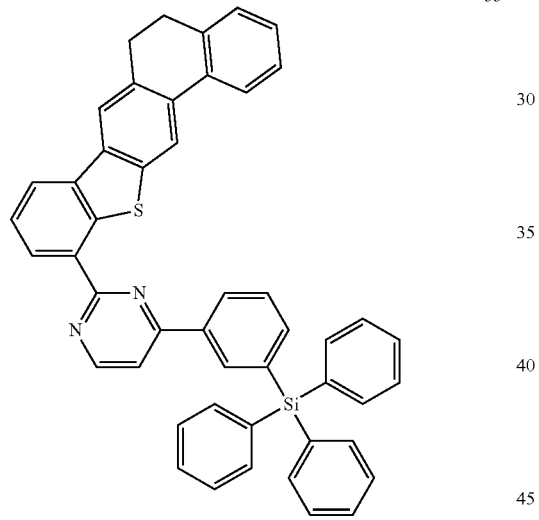
56
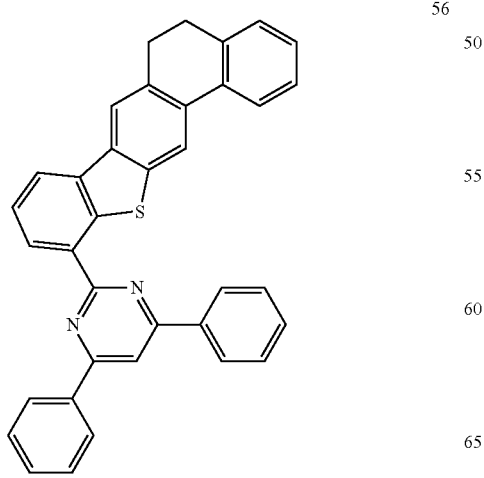
57
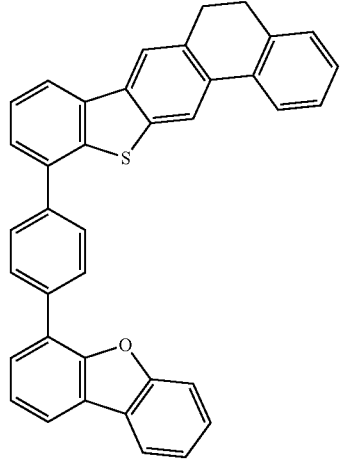
58
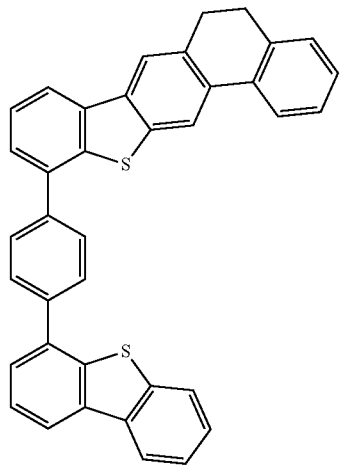
59
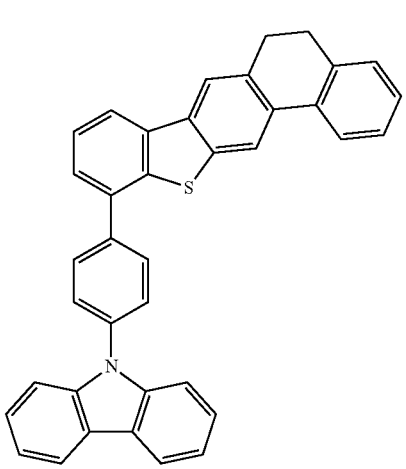

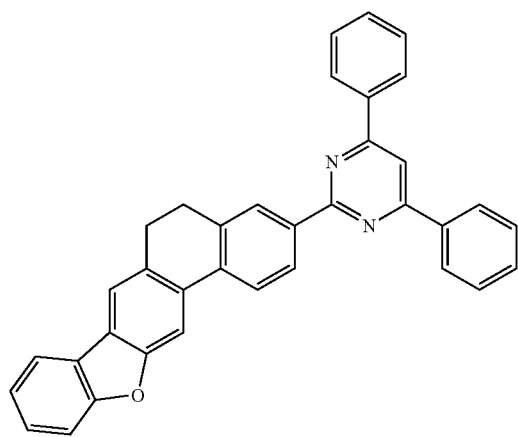
60
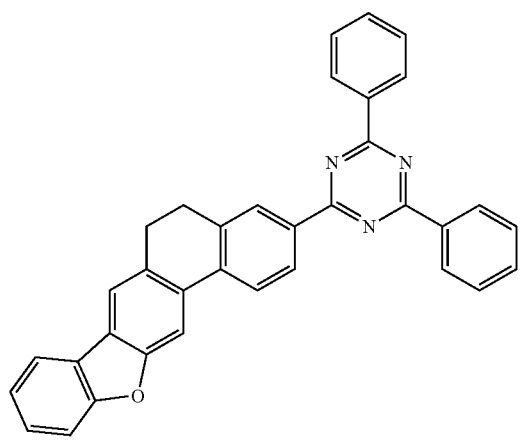
61
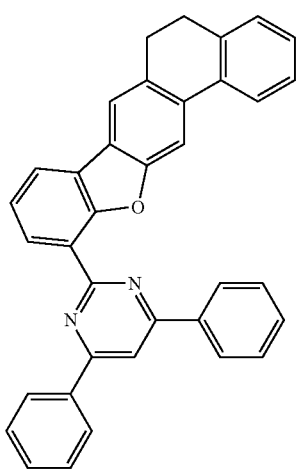
62
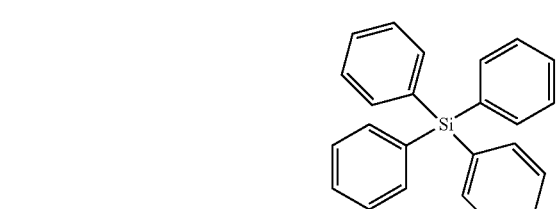
63
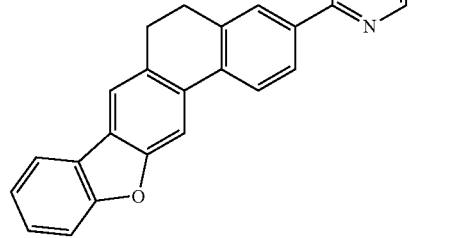
64
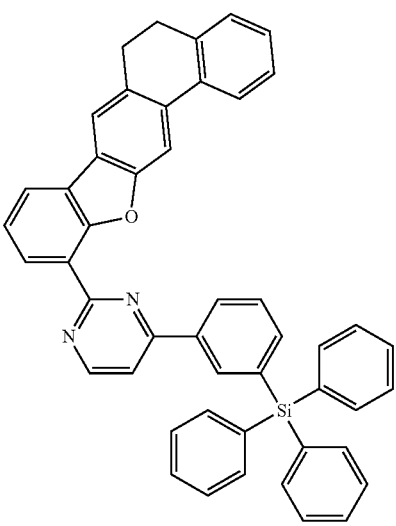
65

66
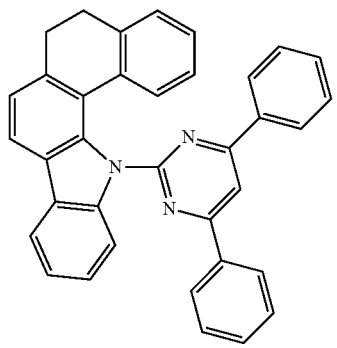
67
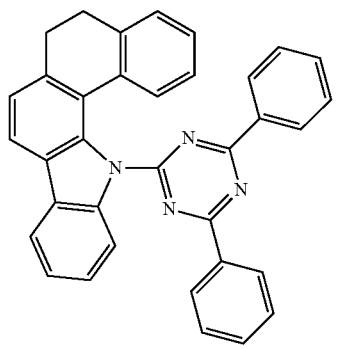
68
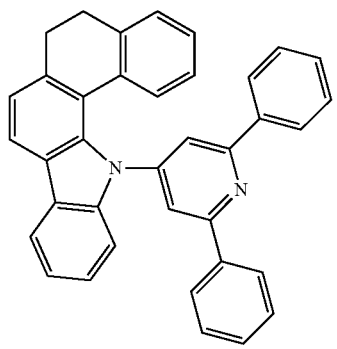
The compound represented by the above Chemical Formula 4 may be selected from one of the following chemical structures 69 to 92 of Group 2.
Group 2
[69]
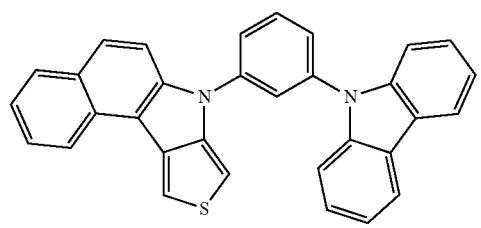
[70]
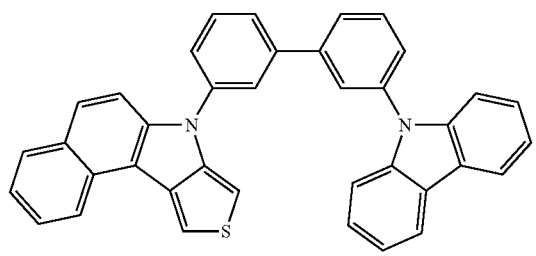
[71]
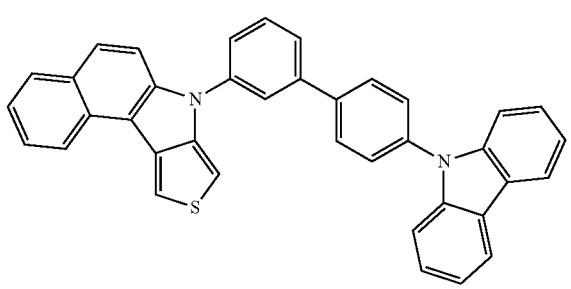
[72]
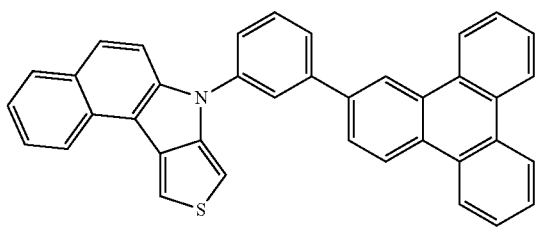
[73]
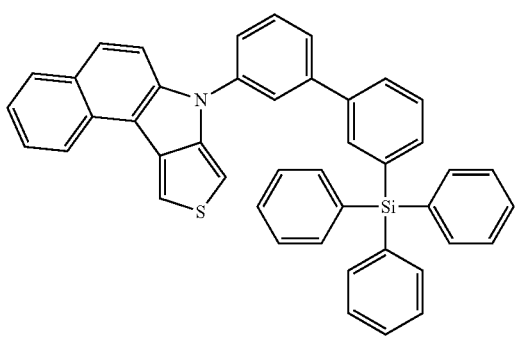
[74]

[75]
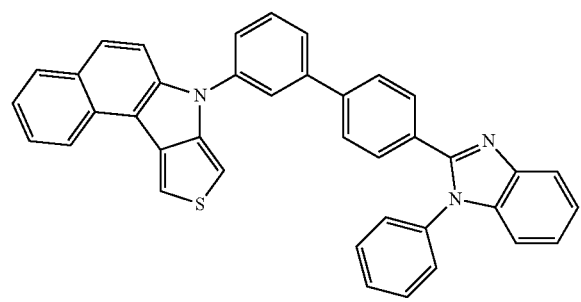
[76]
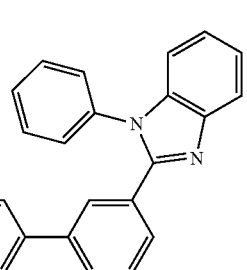
[77]
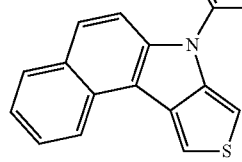
[78]
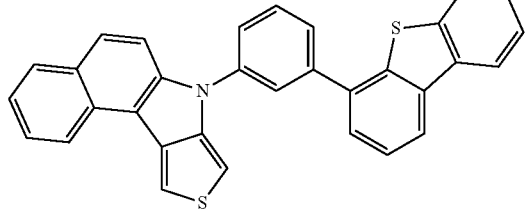
[79]
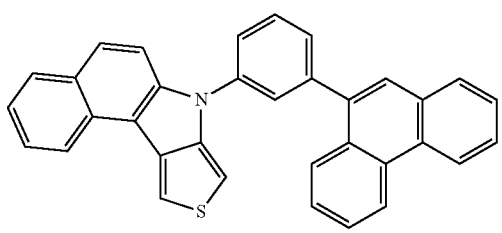
[80]
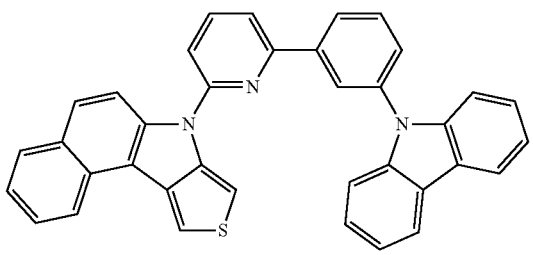
[81]
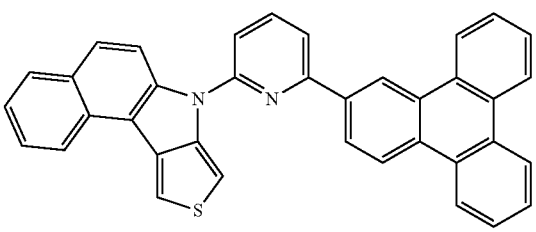
[82]
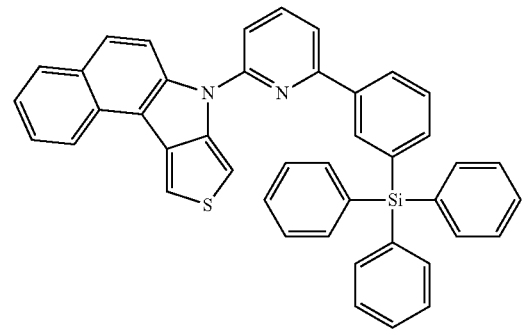
[83]
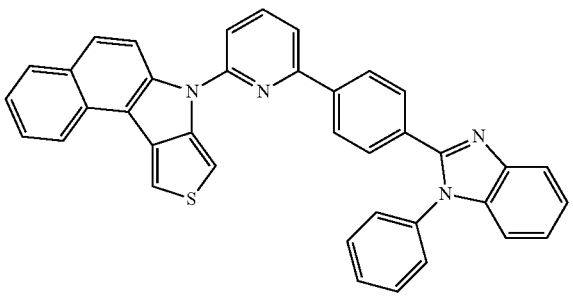
[84]
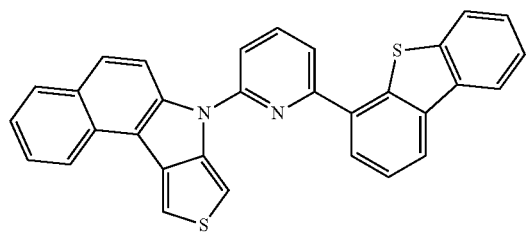

[85]

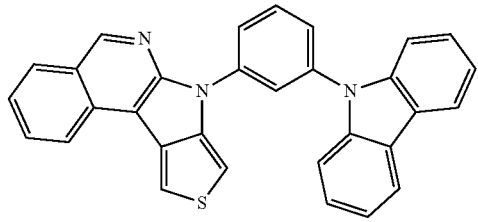

[86]

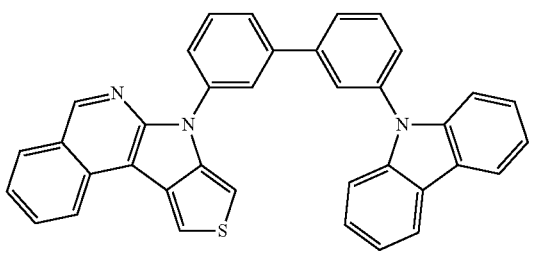

[87]

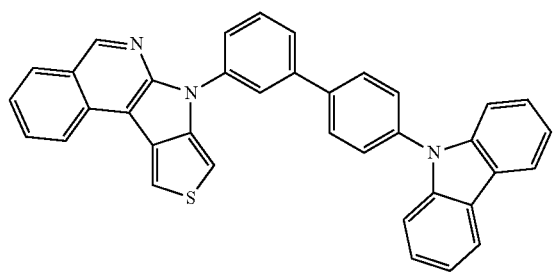

[88]

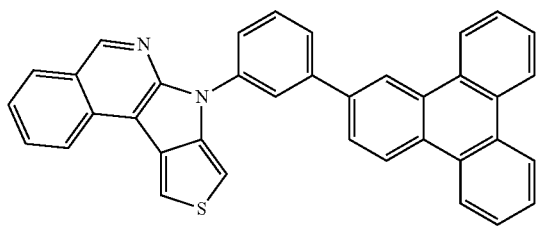

[89]

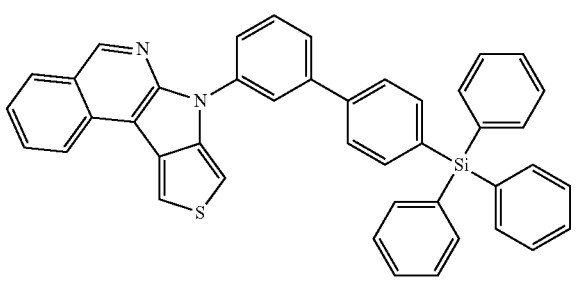

[90]

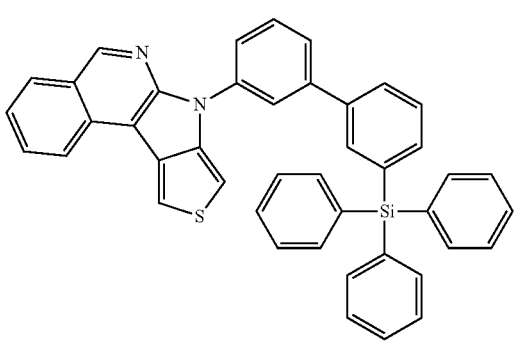

[91]

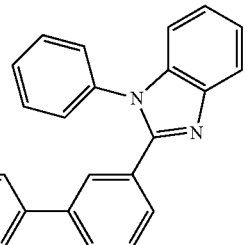

[92]

A weight ratio of the compound represented by one of the above Chemical Formulae 1 to 3 and the compound represented by the above Chemical Formula 4 may be about 0.01:0.99 to about 0.99:0.01.

According to another embodiment, an organic light emitting device includes an anode, a cathode, and an organic layer between the anode and the cathode. The organic layer may include the material for the organic light emitting device.

The organic layer may be an electron injection layer (EIL), an electron transport layer (ETL), a hole injection layer (HIL), a hole transport layer (HTL), or an emission layer.

The emission layer may further include a dopant and may have red, green, or blue light emitting characteristics.

According to yet another embodiment, a display device includes the organic light emitting device.

The organic light emitting device according to one embodiment has high efficiency and long life-span.

DETAILED DESCRIPTION

Figure 1:
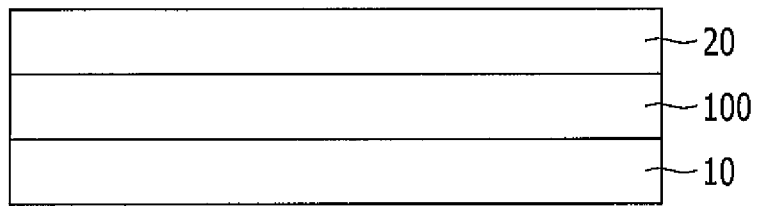
FIG. 1 is a cross-sectional view showing the structure of an organic light emitting device according to one embodiment.

Hereinafter, organic light emitting devices according to embodiments are described.

The embodiments will be described so that a person of an ordinary skill in the art may understand the spirit of the present invention, but the present invention is not limited thereto.

The embodiments may be embodied in many different forms within the spirit and scope of the present invention.

As used herein, when a definition is not otherwise provided, the term "substituted" may refer to a functional group substituted with a C1 to C30 alkyl group; a C1 to C10 alkylsilyl group; a C3 to C30 cycloalkyl group; a C6 to C30 aryl group; a C2 to C30 heteroaryl group; a C1 to C10 alkoxy group; a fluoro group; a C1 to C10 trifluoroalkyl group such as a trifluoromethyl group or the like; or a cyano group.

As used herein, when a definition is not otherwise provided, the term "hetero" may refer to a compound or substituent having 1 to 3 heteroatoms selected from B, N, O, S, P and Si, and the remaining being carbon.

As used herein, when a definition is not otherwise provided, the term "combination thereof" refers to at least two substituents bound to each other by a linking group, or at least two substituents condensed to each other.

As used herein, when a definition is not otherwise provided, the term "alkyl group" may refer to a "saturated alkyl group" without an alkene group or an alkyne group; or an "unsaturated alkyl group" including at least one of an alkenyl group or an alkynyl group.

The term "alkenyl group" may refer to a substituent in which at least two carbon atoms are bound with a carbon-carbon double bond; and the term "alkynyl group" refers to a substituent in which at least two carbon atoms are bound with a carbon-carbon triple bond.

The alkyl group may be a branched, linear, or cyclic alkyl group.

The alkyl group may be a C1 to C20 alkyl group, for example, a C1 to C6 alkyl group, a C7 to C10 alkyl group, or a C11 to C20 alkyl group.

For example, a C1-C4 alkyl group may have 1 to 4 carbon atoms, and may be selected from methyl, ethyl, propyl, iso-propyl, n-butyl, iso-butyl, sec-butyl, and t-butyl.

Examples of the alkyl group include a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

The term "aromatic group" may refer a substituent including a cyclic structure where all elements have p-orbitals which form conjugation.

Examples of the aromatic group include an aryl group and a heteroaryl group.

The term "aryl group" may refer to a monocyclic or fused ring-containing polycyclic (i.e., rings sharing adjacent pairs of carbon atoms) groups.

The "heteroaryl group" may refer to a functional group including 1 to 3 heteroatoms selected from N, O, S, or P as a ring-forming atom in an aryl group, and the remaining being carbon atoms.

When the heteroaryl group is a fused ring, each ring may include 1 to 3 heteroatoms.

As used herein, the term "and/or" refers to at least one of the listed constituent elements.

As used herein, constituent elements and/or portions are depicted using the words "first", "second", and the like, which are used for definite description.

As used herein, when a definition is not otherwise provided, it will be understood that when one constituent element is referred to as being "on" another constituent element, it may be directly on the other element or intervening elements may also be present.

In the drawings, the thicknesses and/or relative thicknesses of constituent elements are exaggerated for clarity so that embodiments of the present invention are definitely described.

The terms indicating positions such as "upper" or "under" are used for definite description of relative positions, and do not indicate absolute positions of constituent elements.

Hereinafter, organic light emitting devices according to embodiments of the present invention are described with reference to the drawings.

According to one embodiment, a material for an organic light emitting device includes a compound represented by one of the following Chemical Formulae 1 to 3 and a compound represented by the following Chemical Formula 4.

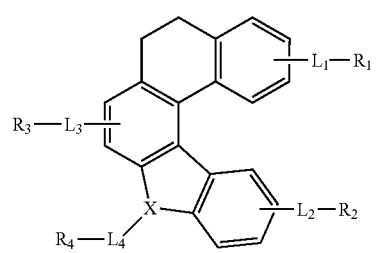

Chemical Formula 1

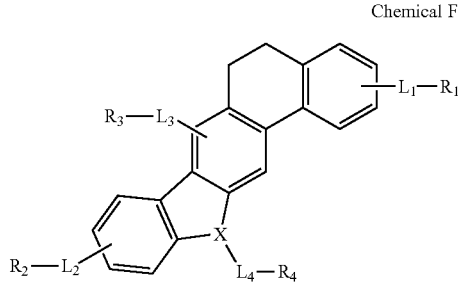

Chemical Formula 2

-continued

Chemical Formula 3

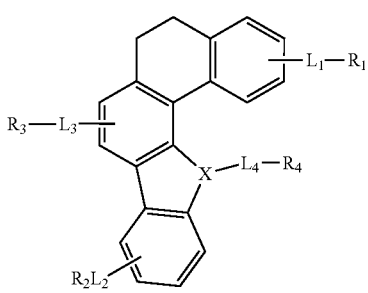

In the above Chemical Formulae 1 to 3, $L_1$ to $L_4$ are each independently a single bond, a substituted or unsubstituted C6 to C30 arylene group, a substituted or unsubstituted C3 to C30 heteroarylene group, or a combination thereof;

$R_1$ to $R_4$ are each independently hydrogen, deuterium, a substituted or unsubstituted C1 to C30 alkyl group, a substituted or unsubstituted C1 to C30 haloalkyl group, a halogen, a cyano group, a substituted or unsubstituted C3 to C30 cycloalkyl group, a substituted or unsubstituted C5 to C7 heterocycloalkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C1 to C30 alkoxy group, a substituted or unsubstituted C6 to C30 aryloxy group, a substituted or unsubstituted C3 to C30 heteroaryl group, a nitro group, $-P(=O)R_aR_b$, $-P(=S)R_aR_b$, a hydroxyl group, or a combination thereof, wherein $R_a$ and $R_b$ are each independently a substituted or unsubstituted C6 to C30 aryl group, a substituted or unsubstituted C3 to C30 heteroaryl group, or a combination thereof; and X is N, S or O.

When X=N, *-$L_4$-$R_4$ is not hydrogen.

Chemical Formula 4

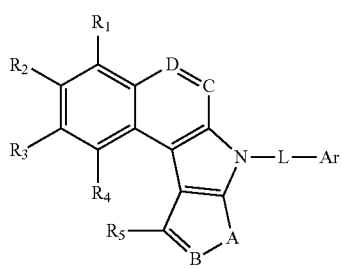

In the above Chemical Formula 4, $R_1$ and $R_5$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxyl group, a carboxyl group, or a combination thereof;

A is C, N, O or S; B is N, O or S;
C and D are each independently N or C;

L is a single bond, a substituted or unsubstituted C6 to C40 arylene group, or a substituted or unsubstituted C3 to C40 heteroarylene group; and Ar is a substituted or unsubstituted C6 to C40 aryl group, a substituted or unsubstituted C5 to C40 heterocycloalkyl group, a substituted or unsubstituted C3 to C40 heteroaryl group, or a combination thereof.

Compounds represented by the above Chemical Formulae 1 to 3 shows excellent (e.g., high) hole mobility, and a compound represented by the above Chemical Formula 4 shows excellent (e.g., high) electron mobility.

Accordingly, when a material obtained by mixing the compound represented by one of the above Chemical Formulae 1 to 3 and the compound represented by the above Chemical Formula 4 is applied to an organic light emitting device, excellent light emitting characteristics and life-span characteristics may be obtained.

In addition, these compounds are not applied to an organic light emitting device in a separate co-deposition method, but pre-mixed to prepare one host (i.e., a single host material) and thus, efficiency of a deposition process performed later may be increased.

For example, in the above Chemical Formulae 1 to 3, $L_1$ to $L_4$ may be each independently a substituted or unsubstituted C3 to C30 heteroarylene group.

For example, in the above Chemical Formulae 1 to 3, $R_1$ to $R_4$ may be each independently a substituted or unsubstituted C5 to C7 heterocycloalkyl group, a substituted or unsubstituted C3 to C30 heteroaryl group, or a combination thereof.

The heteroarylene group, heterocycloalkyl group and heteroaryl group may each independently include at least one heteroatom selected from B, N, O, S, P and Si.

In the above Chemical Formulae 1 to 3, $L_1$ to $L_4$ and $R_1$ to $R_4$ may be each independently further substituted with deuterium, a substituted or unsubstituted C1 to C30 alkyl group, a substituted or unsubstituted C1 to C30 haloalkyl group, a halogen, a cyano group, a substituted or unsubstituted C3 to C30 cycloalkyl group, a substituted or unsubstituted C5 to C7 heterocycloalkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C1 to C30 alkoxy group, a substituted or unsubstituted C6 to C30 aryloxy group, a substituted or unsubstituted C3 to C30 heteroaryl group, a nitro group, a hydroxyl group, or a combination thereof.

For example, in the above Chemical Formula 4, Ar may be phenyl, biphenyl, terphenyl, naphthyl, anthracenyl, phenanthryl, pyrenyl, fluorenyl, carbazolyl, N-carbazolephenyl, quinolinyl, isoquinolinyl, or a combination thereof, but is not limited thereto.

In the above Chemical Formula 4, Ar may be substituted with deuterium, a substituted or unsubstituted C1 to C40 alkyl group, a substituted or unsubstituted C3 to C40 cycloalkyl group, a substituted or unsubstituted C2 to C40 alkenyl group, a substituted or unsubstituted C1 to C40 alkoxy group, a substituted or unsubstituted C1 to C40 alkylamino group, a substituted or unsubstituted C6 to C40 aryl group, a substituted or unsubstituted C5 to 40 heteroaryl group, or a combination thereof.

In addition, these substituents may form a Spiro bond with adjacent groups, or a condensed ring with a substituted or unsubstituted C6 to C40 aliphatic cyclic group, a substituted or unsubstituted C6 to C40 aromatic ring group, a substituted or unsubstituted C6 to C40 heteroaliphatic cyclic group, or a substituted or unsubstituted C6 to C40 heteroaromatic ring group.
The compound represented by one of the above Chemical Formulae 1 to 3 may be one selected from the following chemical structures 1 to 68 of Group 1, but is not limited thereto.
Group 1
1
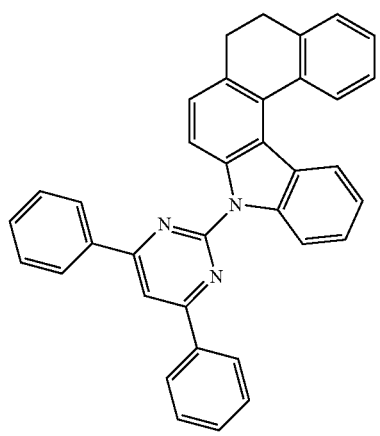
2
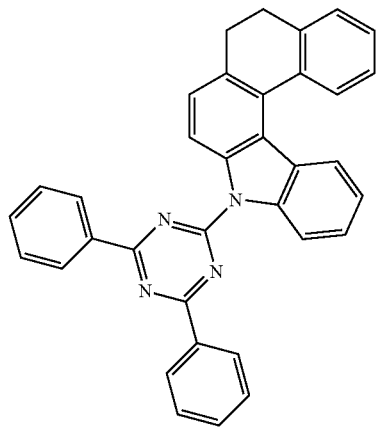
3
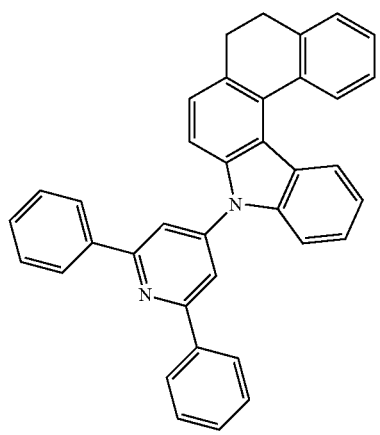
4
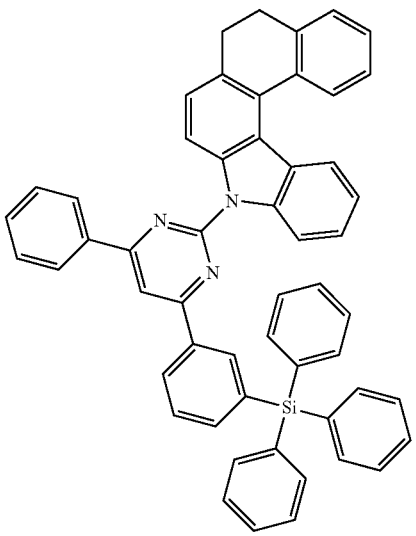
5
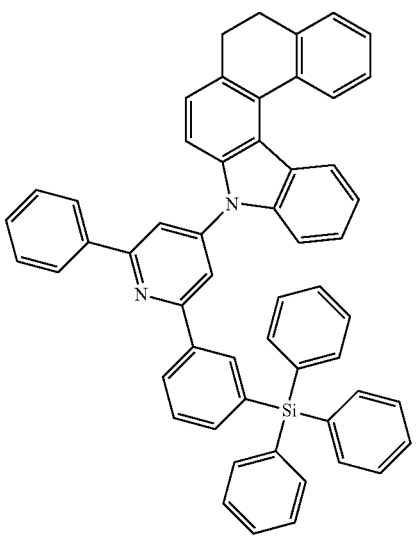
6
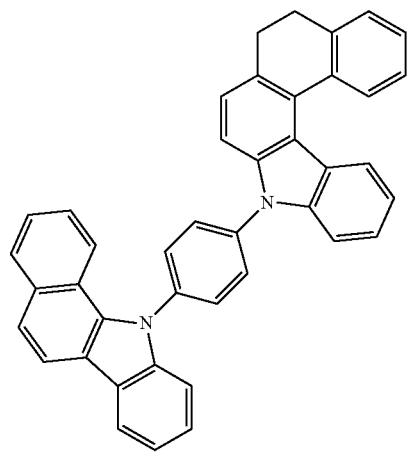

-continued
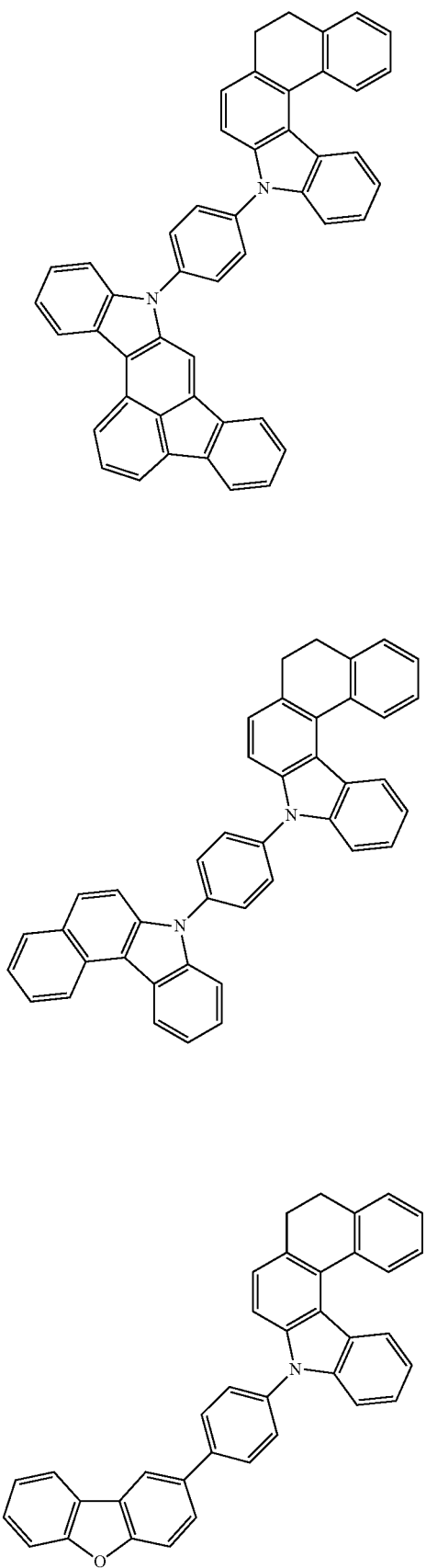
-continued
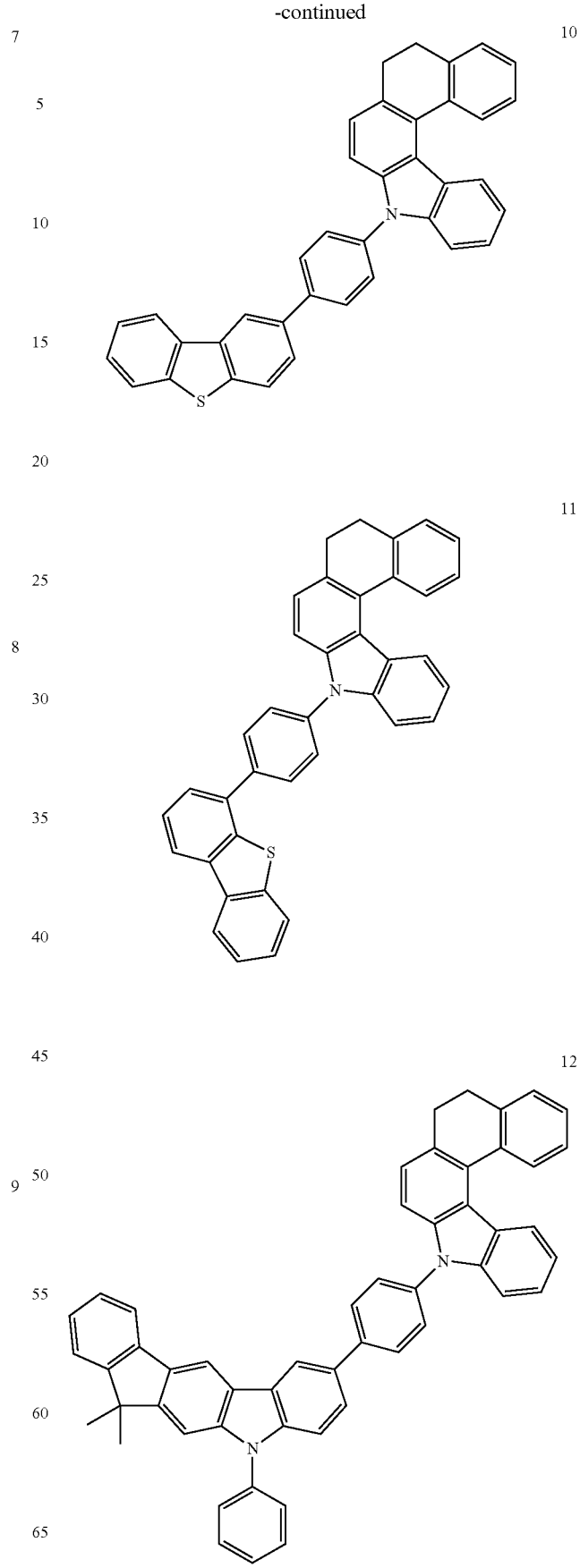

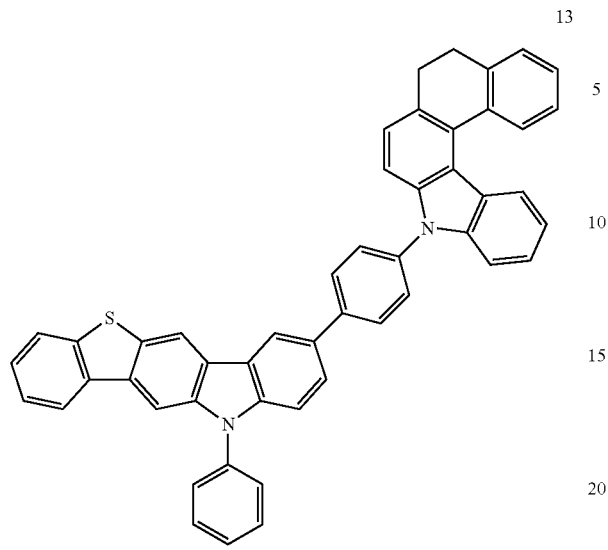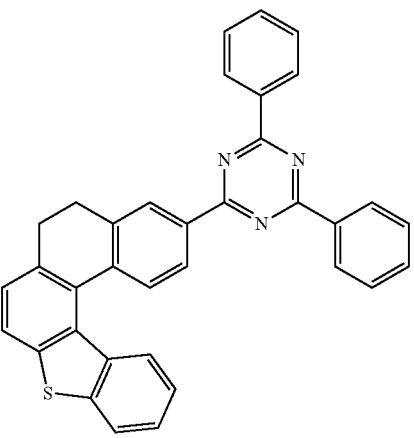

19
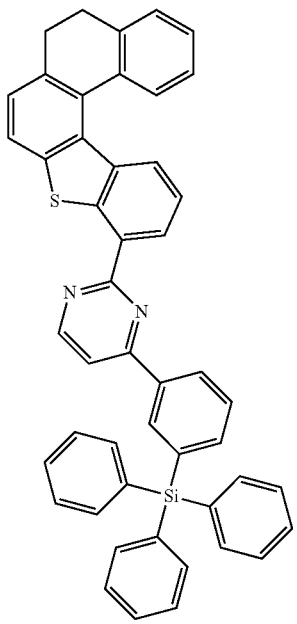
20
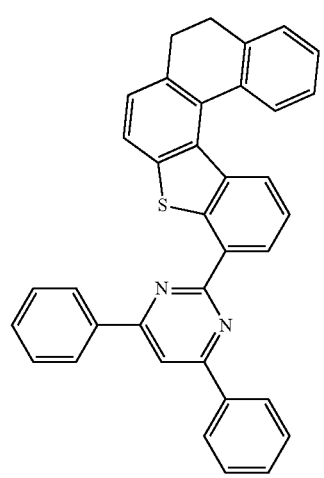
21
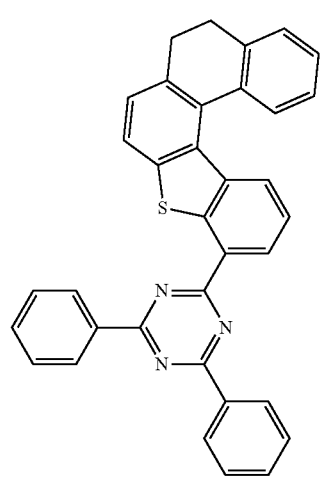
22
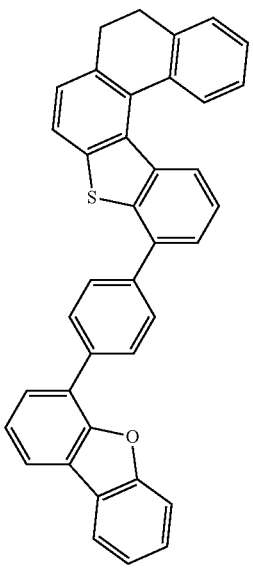
23
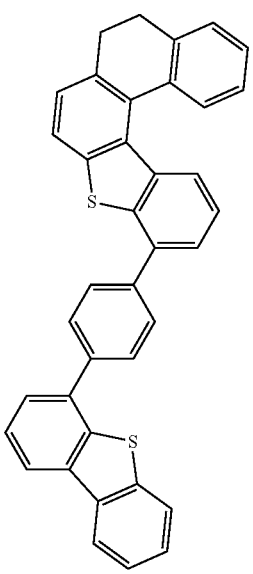
24
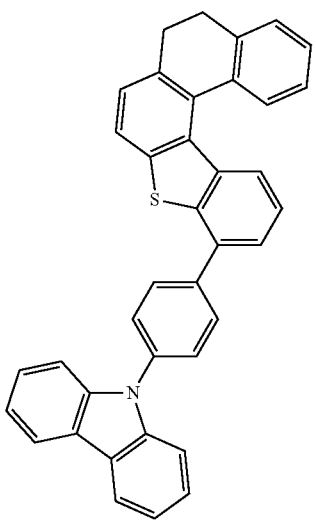

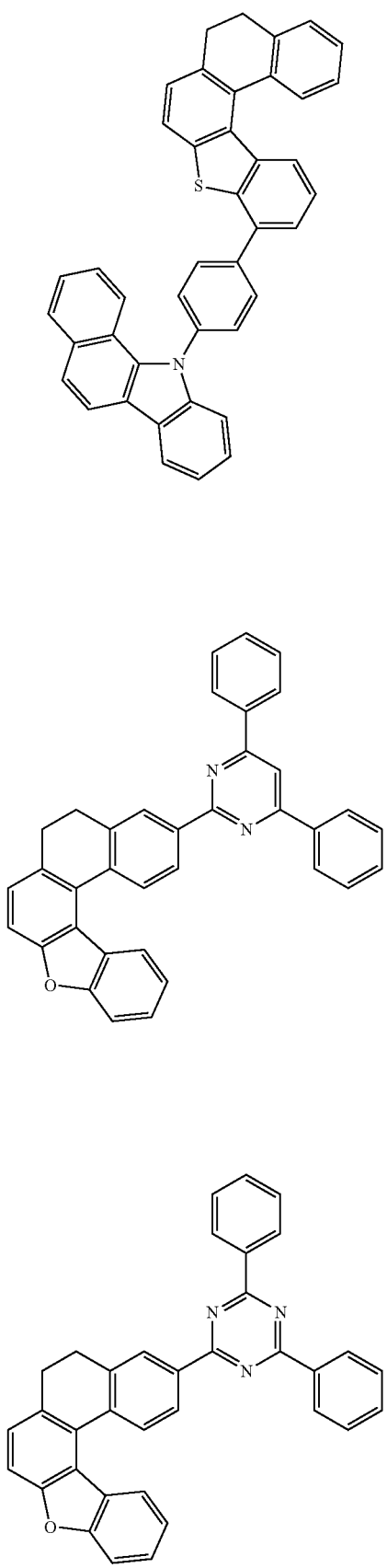
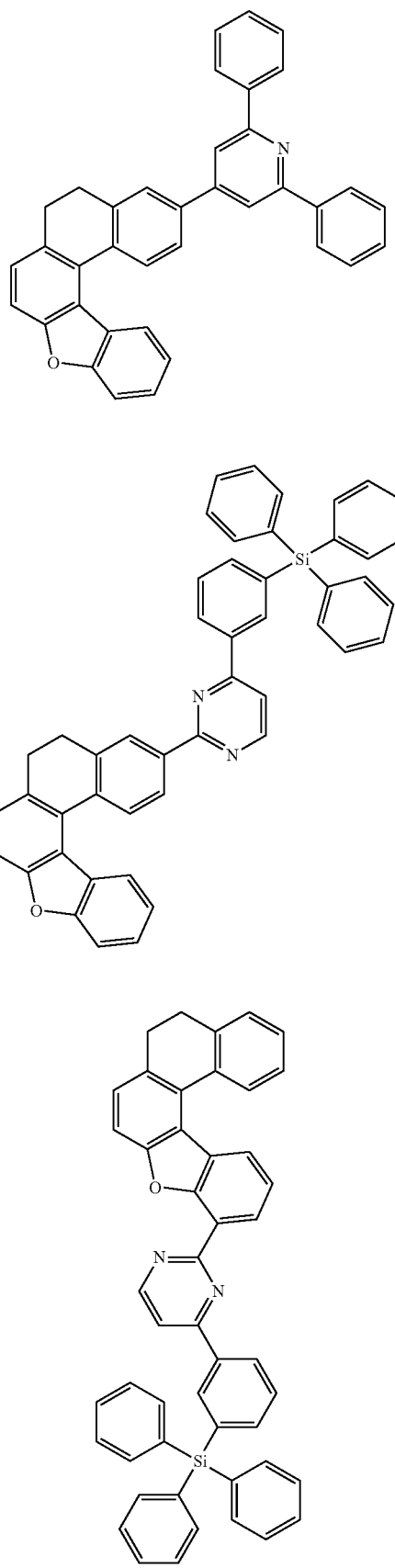

31
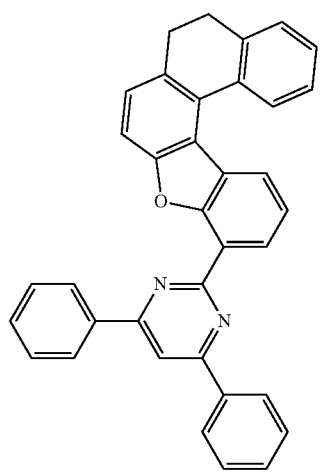
32
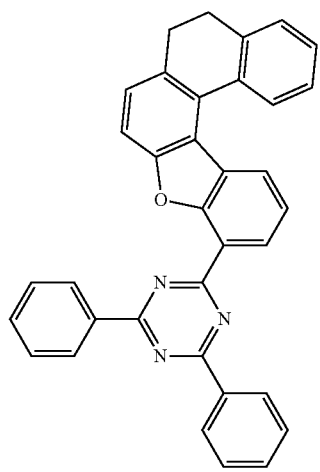
33
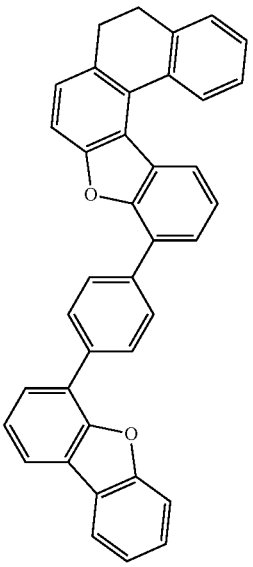
34
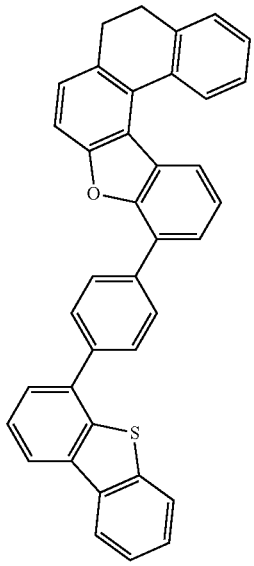
35
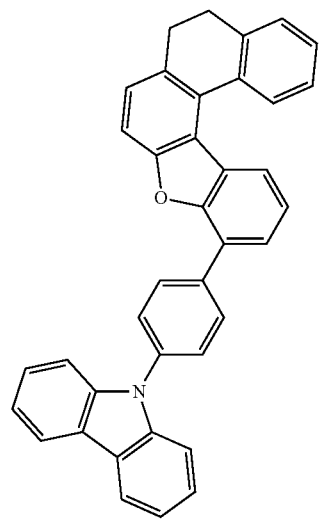
36
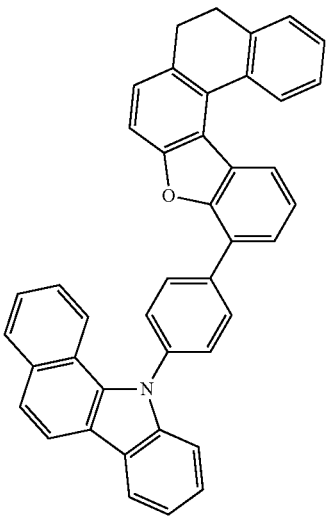

37
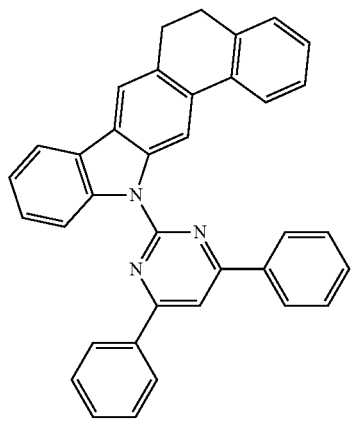
38
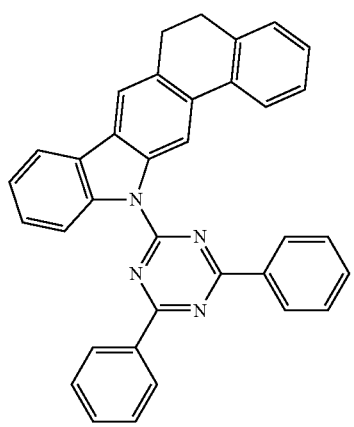
39
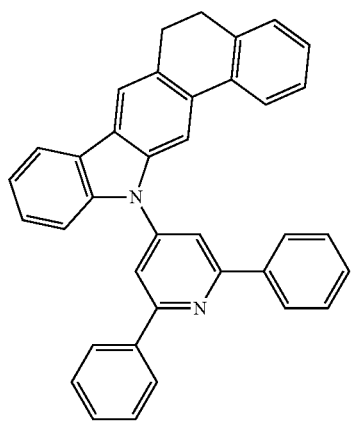
40
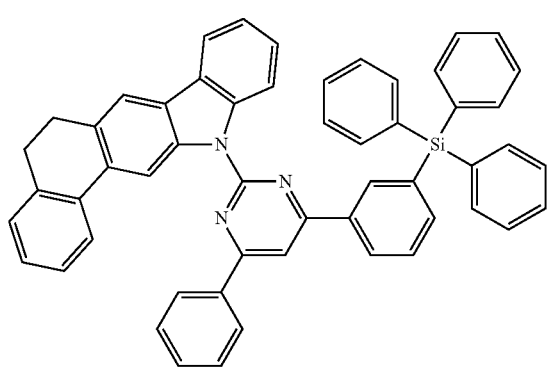
41
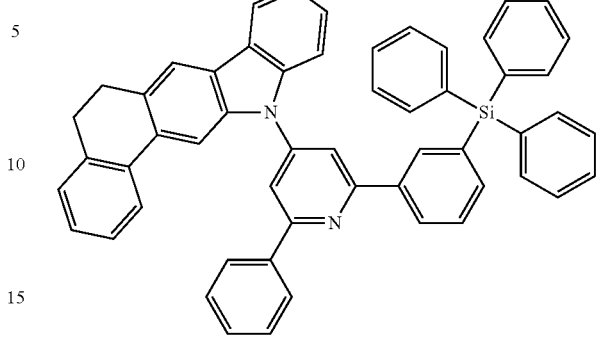
42
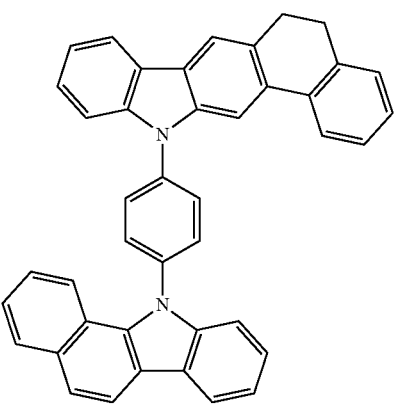
43
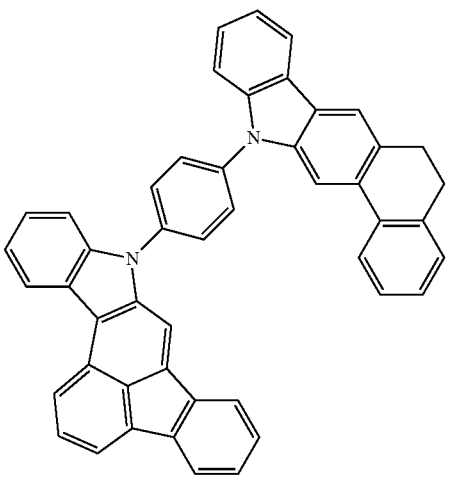

44
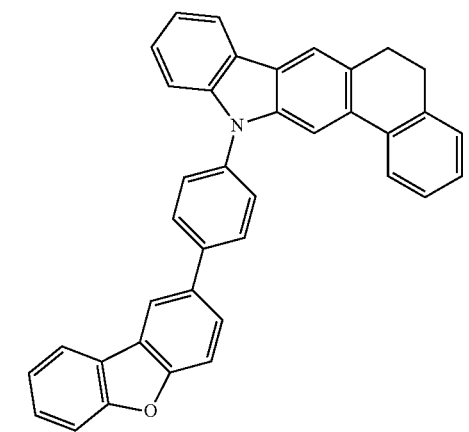
45
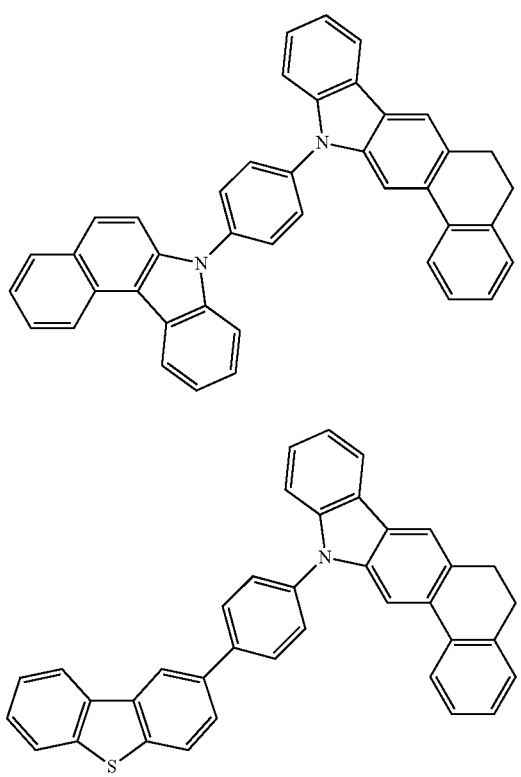
46
48
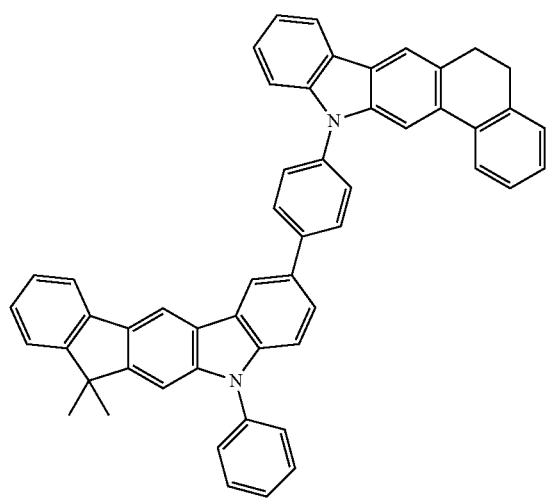
49
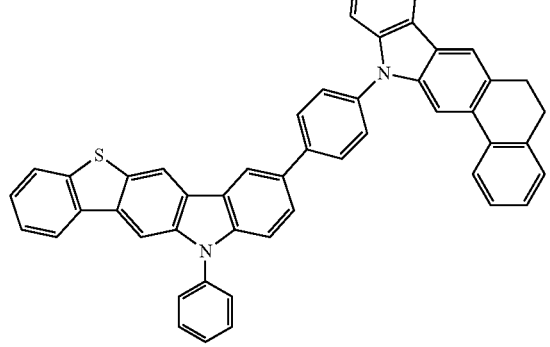
50
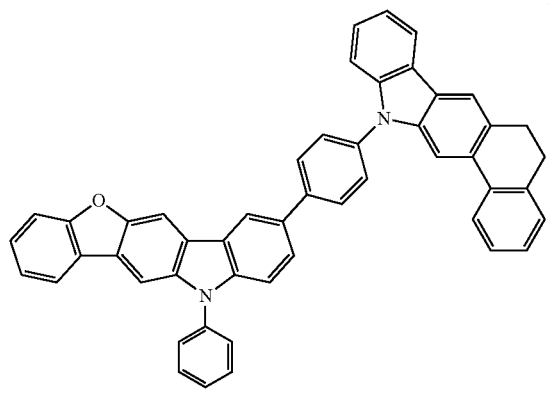

51
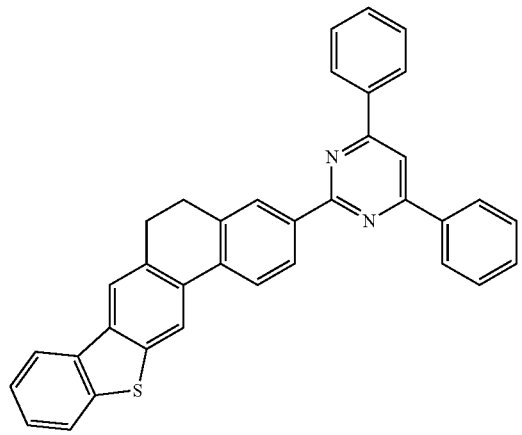
52
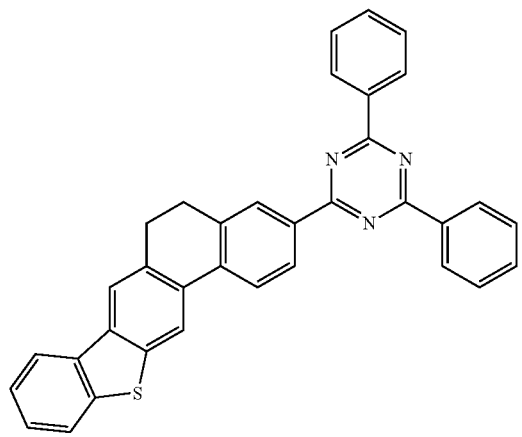
53
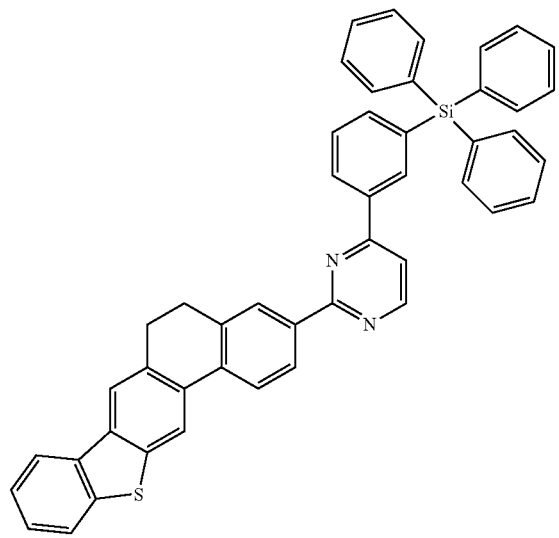
54
55
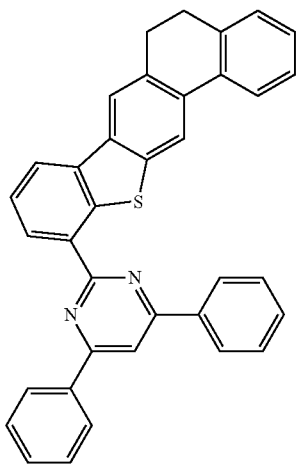
56

57
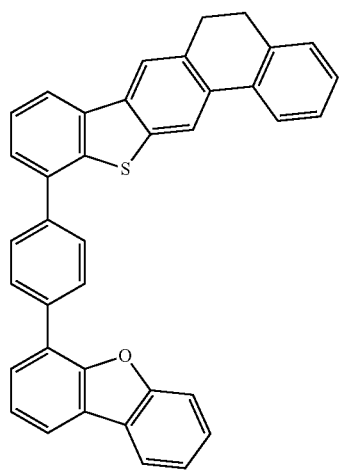
58
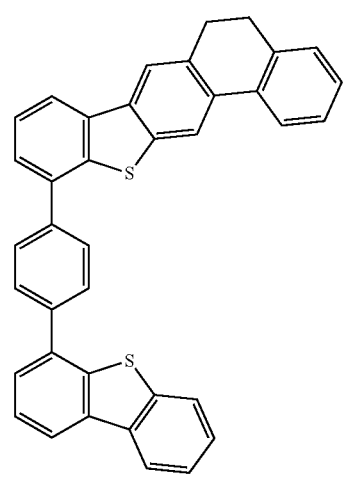
59
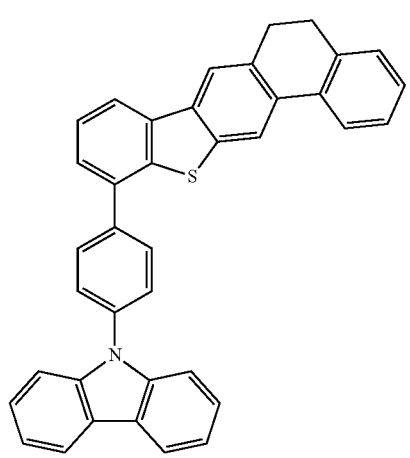
60
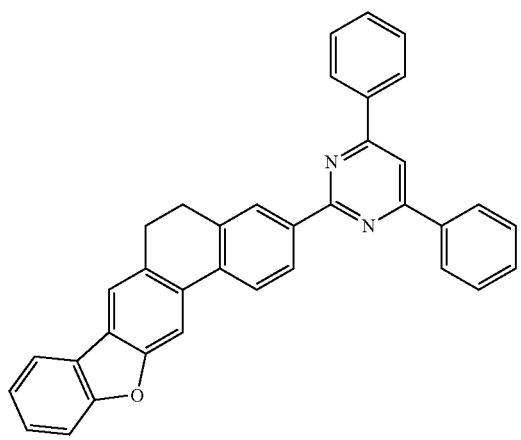
61
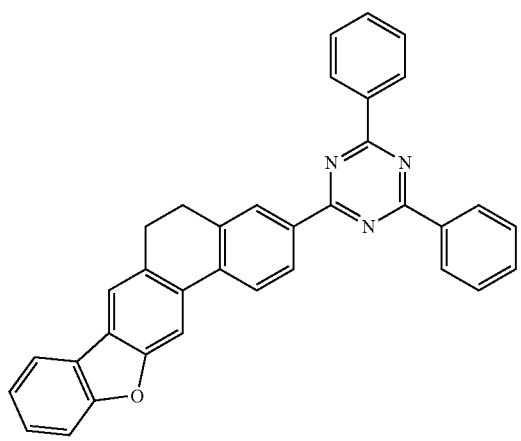
62
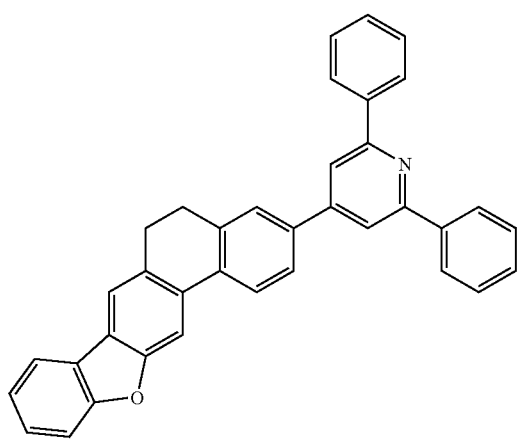

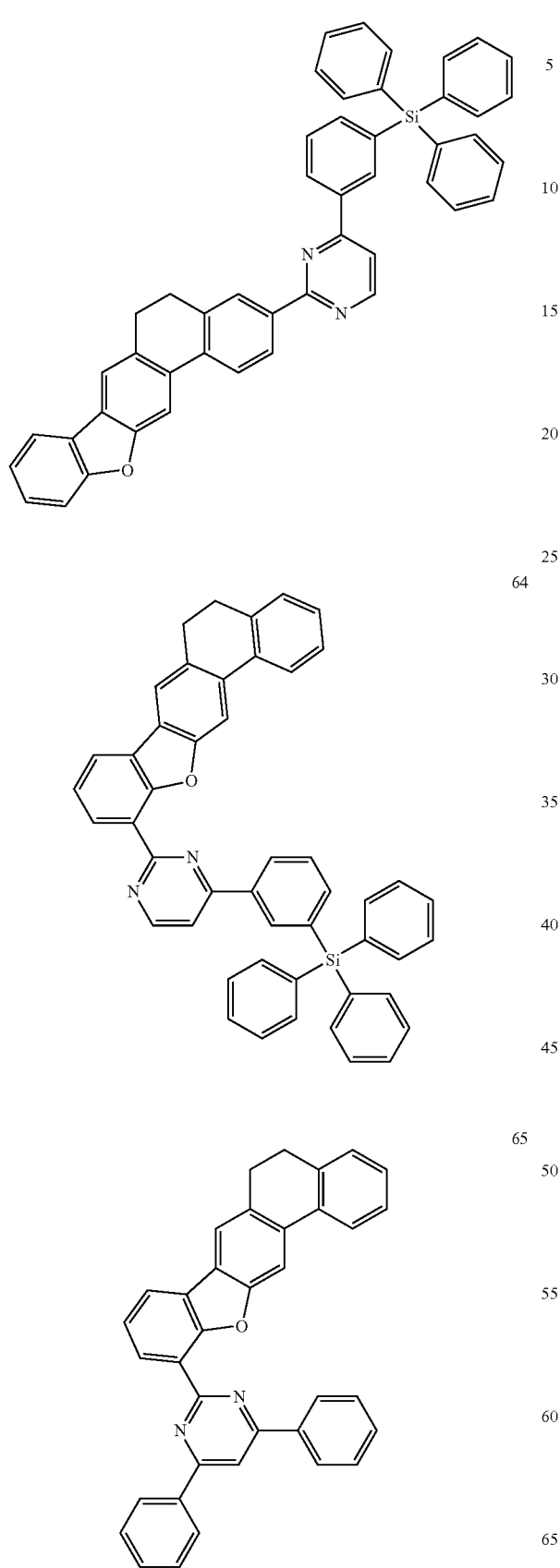
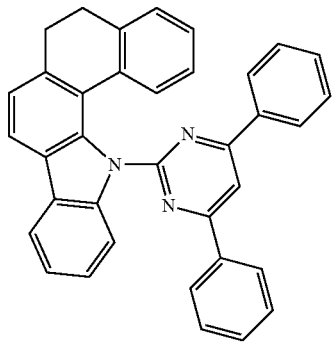
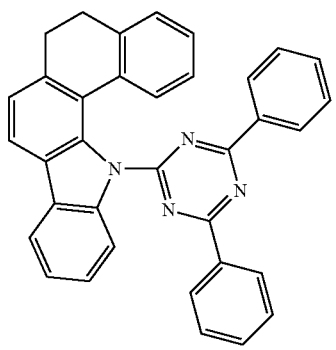
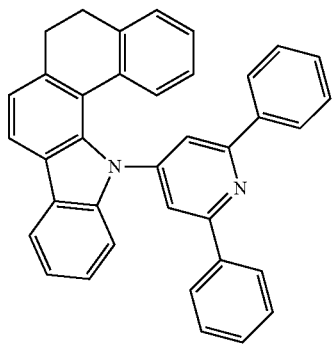
The compound represented by the above Chemical Formula 4 may be selected from one of the following chemical structures 69 to 92 of Group 2, but is not limited thereto.
Group 2
[69]
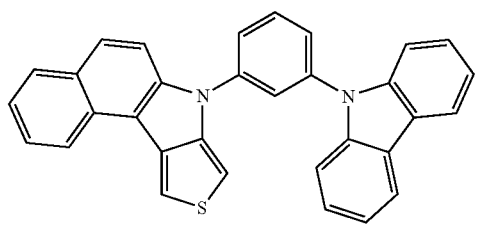

[70]
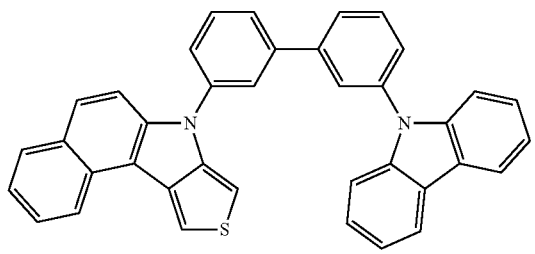
[71]
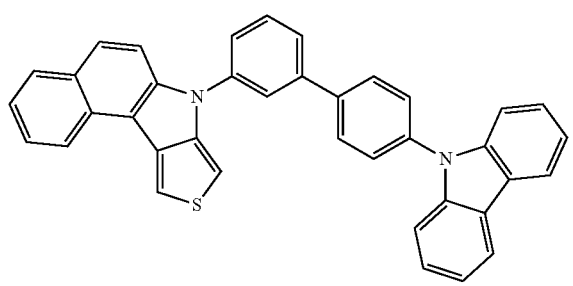
[72]
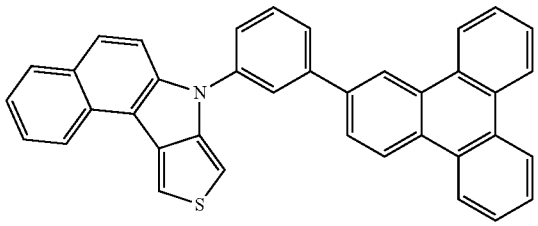
[73]
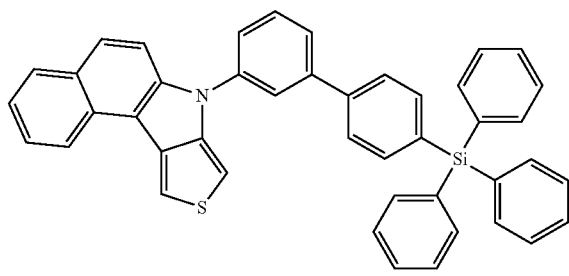
[74]
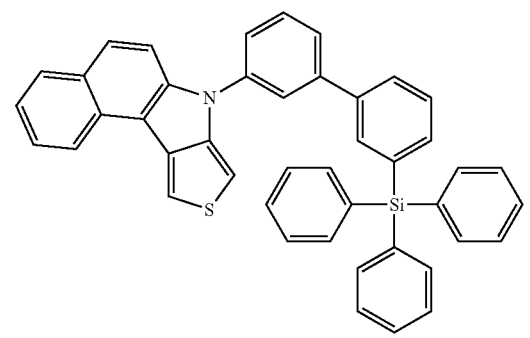
[75]
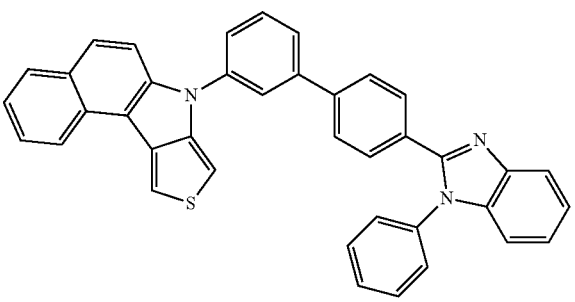
[76]
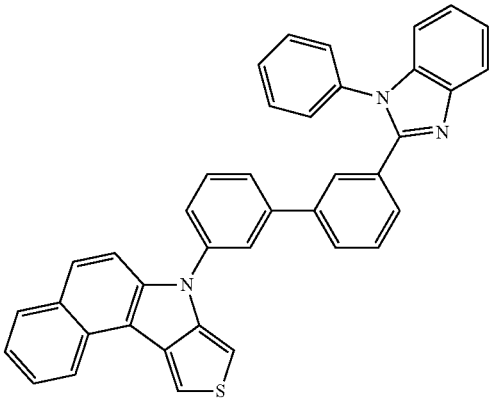
[77]
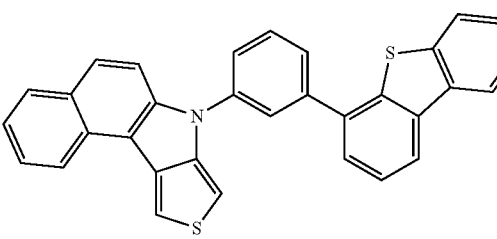
[78]
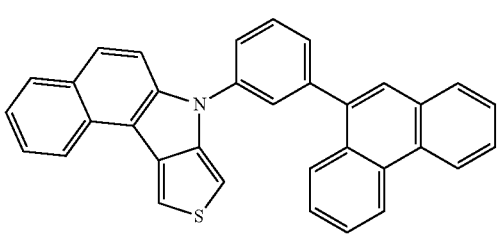
[79]
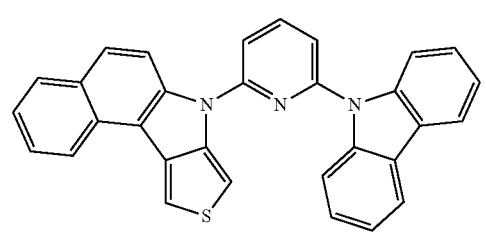

[80]
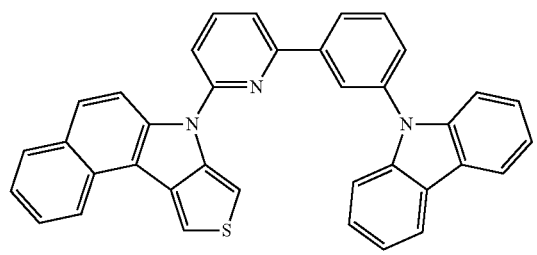
[81]
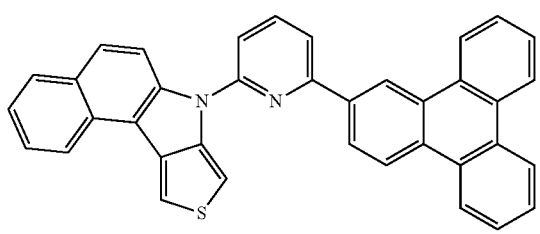
[82]
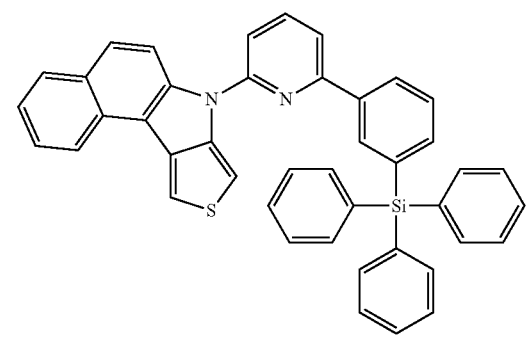
[83]
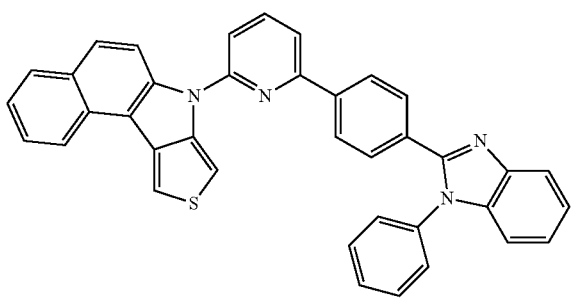
[84]
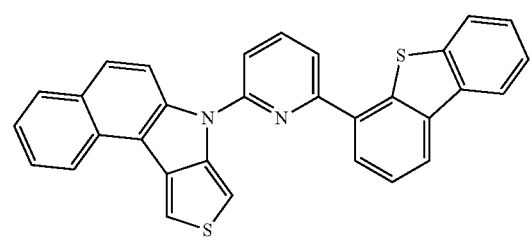
[85]
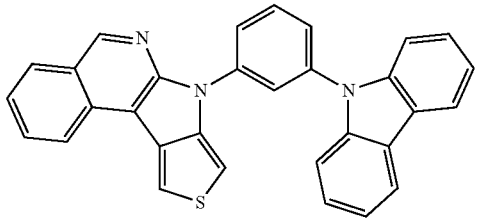
[86]
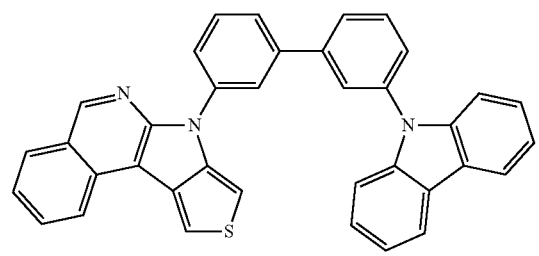
[87]
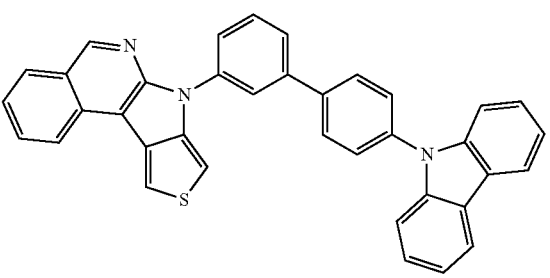
[88]
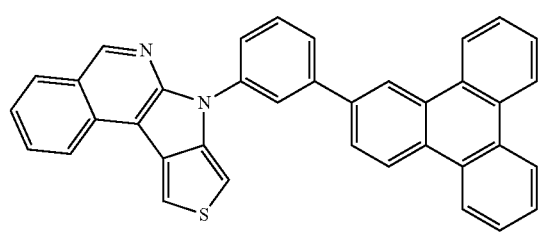
[89]
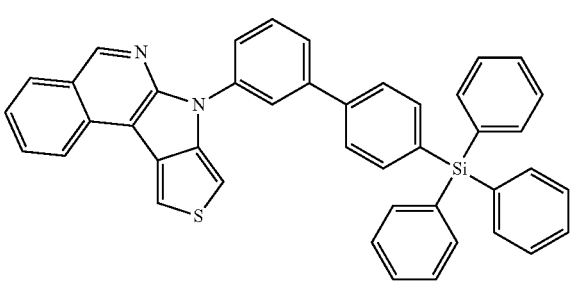

[90]

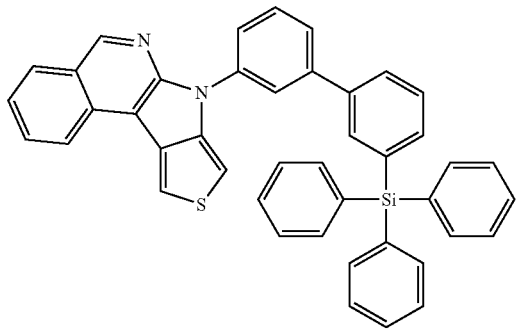

[91]

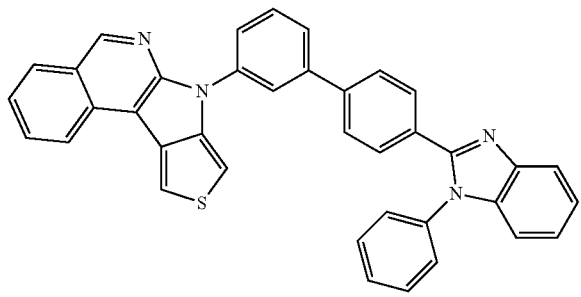

[92]

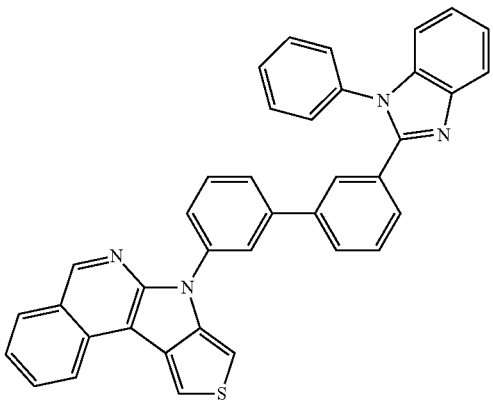

The compounds represented by the above Chemical Formulae 1 to 3 may be included in plural in the material for an organic light emitting device.

For example, the material for an organic light emitting device may concurrently (e.g., simultaneously) include a compound represented by the above Chemical Formula 1, a compound represented by the above Chemical Formula 2, and a compound represented by the above Chemical Formula 3.

On the other hand, the compound represented by one of the above Chemical Formulae 1 to 3 and the compound represented by the above Chemical Formula 4 are pre-mixed to form one host and may be, for example, mixed in a weight ratio ranging from about 0.01:0.99 to about 0.99:0.01, but the present invention is not limited thereto.

The compound represented by one of the above Chemical Formulae 1 to 3 and the compound represented by the above Chemical Formula 4 may be mixed in a substantially equivalent weight ratio.

The material for an organic light emitting device may further include a dopant, and the dopant may have red, green, or blue light emitting characteristics.

In this case, a weight ratio of the compound represented by one of the above Chemical Formulae 1 to 3, the compound represented by the above Chemical Formula 4, and the dopant may be, for example, (30 to 60): (30 to 60): (0.01 to 15), but is not limited thereto.

Hereinafter, organic light emitting devices according to another embodiment are described referring to FIGS. 1 to 3.

Figure 2:
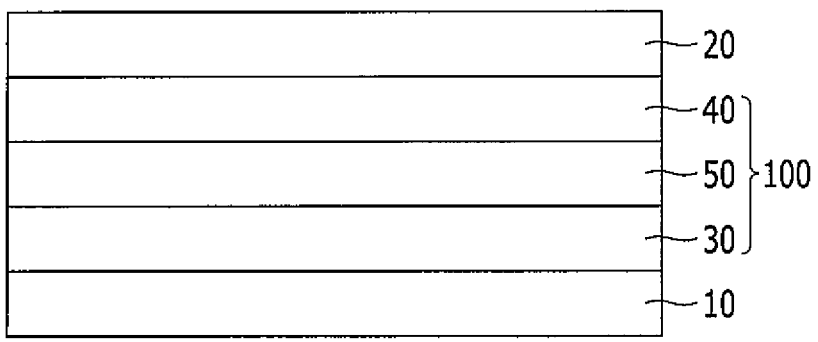
FIG. 2 is a cross-sectional view showing the structure of an organic light emitting device according to another embodiment.
Figure 3:
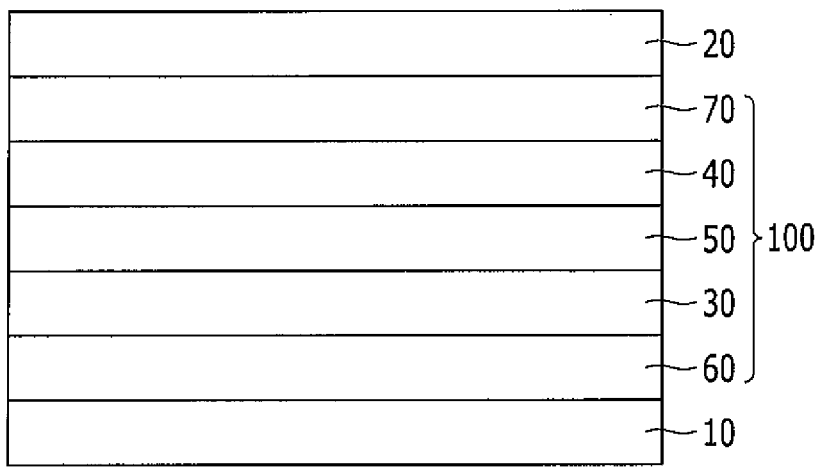
FIG. 3 is a cross-sectional view showing the structure of an organic light emitting device according to yet another embodiment.

FIGS. 1 to 3 are cross-sectional views showing organic light emitting devices according to embodiments of the present invention.

Referring to FIG. 1, an organic light emitting device according to one embodiment includes an anode 10, a cathode 20 facing the anode 10, and an organic layer 100 interposed between the anode 10 and the cathode 20.

The organic layer 100 includes the material (e.g., compound) according to the above embodiment.

The organic layer 10 may be, for example, formed according to various suitable methods such as vacuum deposition, spin coating, casting, or LB.

When the organic layer is formed by vacuum deposition, the deposition conditions may be different according to the compound used (utilized) as the material for the organic layer, the structure of the objective organic layer, and the thermal characteristics, but generally, may be appropriately selected from a deposit temperature of about 100 to about 500° C., a vacuum degree of about $10^{-8}$ to about $10^{-3}$ torr, and a deposition rate of about 0.01 to about 100 Å/sec, without being limited thereto.

When the organic layer is formed by spin coating, the coating conditions may be different according to the compound used (utilized) as the material for the organic layer, the structure of the objective organic layer, and the thermal characteristics or the like, but may be suitably selected from a coating speed of about 2000 rpm to about 5000 rpm, a heat treatment temperature of about 80° C. to about 200° C. for removing the solvent after coating, without being limited thereto.

A substrate may be disposed on the side of the anode 10 or on the side of the cathode 20.

The substrate may be made of an inorganic material (such as glass); an organic material (such as polycarbonate, polymethylmethacrylate, polyethyleneterephthalate, polyethylenenaphthalate, polyamide, polyethersulfone, or a combination thereof); silicon wafer; or the like.

The anode 10 may be a transparent electrode or an opaque electrode.

The transparent electrode may be formed of, for example, conductive oxides such as indium tin oxide (ITO), indium zinc oxide (IZO), tin oxide ($SnO_2$), zinc oxide (ZnO), or a combination thereof; or a metal such as aluminum, silver, or magnesium in a thin thickness. The opaque electrode may be formed of, for example, a metal such as aluminum, silver, or magnesium.

The cathode 20 may include a material having a small work function so that electrons might be easily injected.

For example, the cathode 20 may include a metal or an alloy thereof, such as magnesium, calcium, sodium, potassium, titanium, indium, yttrium, lithium, gadolinium, aluminum, silver, tin, lead, cesium, barium, or the like; a multi-layer structured material such as LiF/Al, $LiO_2$/Al, LiF/Ca, LiF/Al or $BaF_2$/Ca; but is not limited thereto.

In one embodiment, the cathode may be a metal electrode such as aluminum.

Hereinafter, an organic light emitting device according to one embodiment is described with reference to FIG. 2.

Referring to FIG. 2, an organic light emitting device according to another embodiment includes an anode 10, a cathode 20 facing the anode 10, and an organic layer 100 interposed between the anode 10 and the cathode 20, like in the above described embodiment.

The organic layer 100 includes an emission layer 50 interposed between the anode 10 and the cathode 20, a hole transport layer (HTL) 30 interposed between the anode 10 and the emission layer 50, and an electron transport layer (ETL) 40 interposed between the cathode 20 and the emission layer 50.

The hole transport layer (HTL) 30 may increase hole mobility by including the compound according to the above described embodiment.

The hole transport layer (HTL) 30 may further include a p-dopant so as to improve the film conductivity.

Non-limiting examples of the p-dopant may be a quinone derivative (such as tetracyanoquinone dimethane (TCNQ) or 2,3,5,6-tetrafluoro-tetracyano-1,4-benzoquinone dimethane (F4-CTNQ)), metal oxide (such as tungsten oxide or molybdenum oxide), or a cyano group-containing compound (such as the following compound 100), or the like, but is not limited thereto.

Compound 100

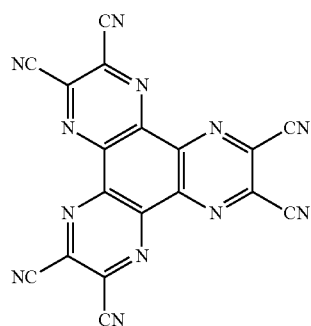 [SMILES: N#Cc1nc2c3nc(C#N)c(C#N)nc3c3nc(C#N)c(C#N)nc3c2nc1C#N]

When the hole transport layer (HTL) 30 further includes the p-dopant, the p-dopant may be, for example, uniformly dispersed in the layer or layers, or randomly distributed in the layer or layers.

The emission layer 50 may include a single compound or a mixture of the compound with another organic compound.

As for the mixture, one compound used (utilized) in a larger amount may act as a fluorescent or phosphorescent host, and the other compound in a smaller amount may act as a dopant.

Suitable hosts may be Alq$_3$, 4,4'-N,N'-dicarbazole-biphenyl (CBP), polyvinylcarbazole (PVK), 9,10-di(naphthalen-2-yl)anthracene (ADN), 4,4',4"-tris(carbazol-9-yl)-triphenylamine (TCTA), 1,3,5-tris(N-phenylbenzimidazol-2-yl) benzene (1,3,5-tris(N-phenylbenzimidazole-2-yl)benzene (TPBI), 3-tert-butyl-9,10-di(napht-2-yl)anthracene (TBADN), E3, distyrylarylene (DSA), or the like, but are not limited thereto.

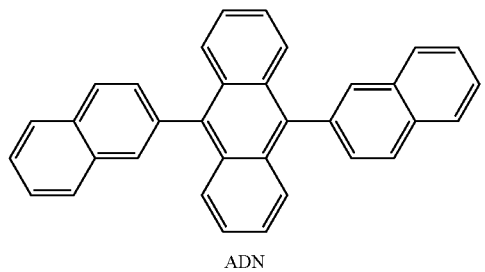 [SMILES: c1ccc2cc(-c3c4ccccc4c(-c4ccc5ccccc5c4)c4ccccc34)ccc2c1]

ADN

On the other hand, suitable red dopants may include PtOEP, Ir(piq)$_3$, Btp$_2$Ir(acac), DCJTB, or the like, but are not limited thereto.

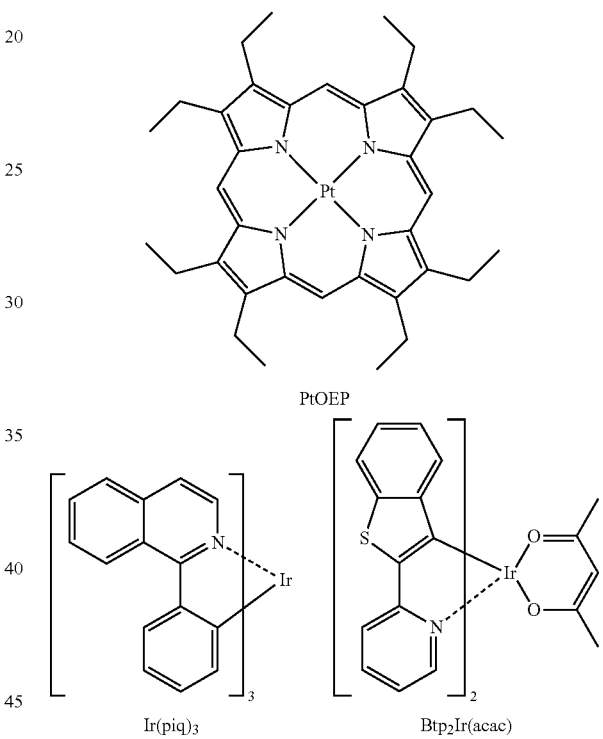

PtOEP

Ir(piq)$_3$  Btp$_2$Ir(acac)

In addition, suitable green dopants may include Ir(ppy)$_3$ (ppy=phenylpyridine), Ir(ppy)$_2$(acac), Ir(mpyp)$_3$, C545T, or the like, but are not limited thereto.

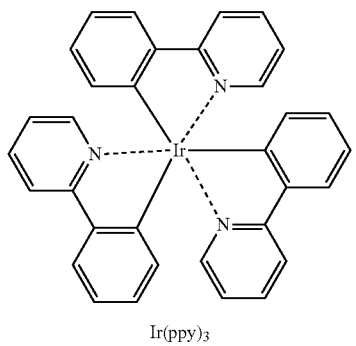

Ir(ppy)$_3$

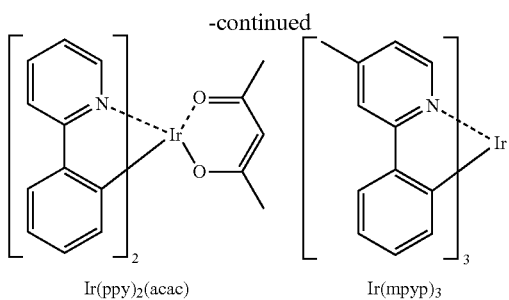

Ir(ppy)₂(acac)  Ir(mpyp)₃

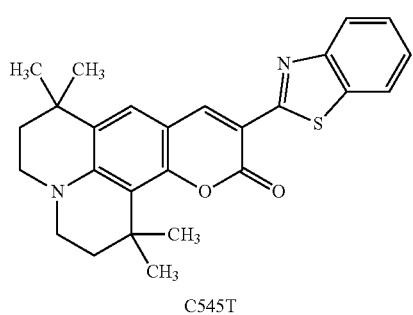

C545T

On the other hand, suitable blue dopants may include F₂Irpic, (F₂ppy)₂Ir(tmd), Ir(dfppz)₃, ter-fluorene, 4,4'-bis(4-diphenylaminostyryl)biphenyl(DPAVBi), 2,5,8,11-tetra-ter-butyl perylene (TBP), or the like, but are not limited thereto.

The dopant may be included in an amount of about 0.1 to about 15 parts by weight based on 100 parts by weight of the emission layer forming material (i.e., the total weight of the host and dopant is 100 parts by weight), without being limited thereto. In one embodiment, when the amount of the dopant is within the above range, a concentration extinction phenomenon is substantially suppressed.

The emission layer 50 may emit white light by a combination of the three primary colors, i.e., red, green and blue. The combination of colors may be implemented by the combination of adjacent sub-pixels to emit white light, or by stacking the primary colors in a vertical direction to emit white light.

The electron transport layer (ETL) may include a suitable electron transport layer (ETL)-forming material. For example, a suitable material such as a quinoline derivative such as tris(8-quinolinolate)aluminum (Alq₃), TAZ, Balq, or the like may be used (utilized), without being limited thereto.

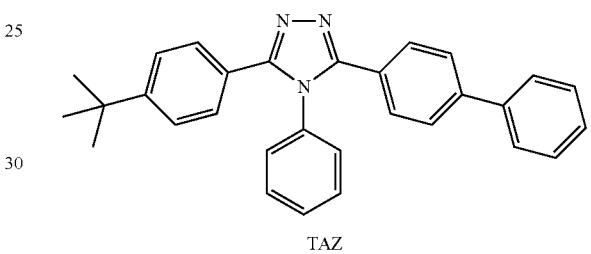

TAZ

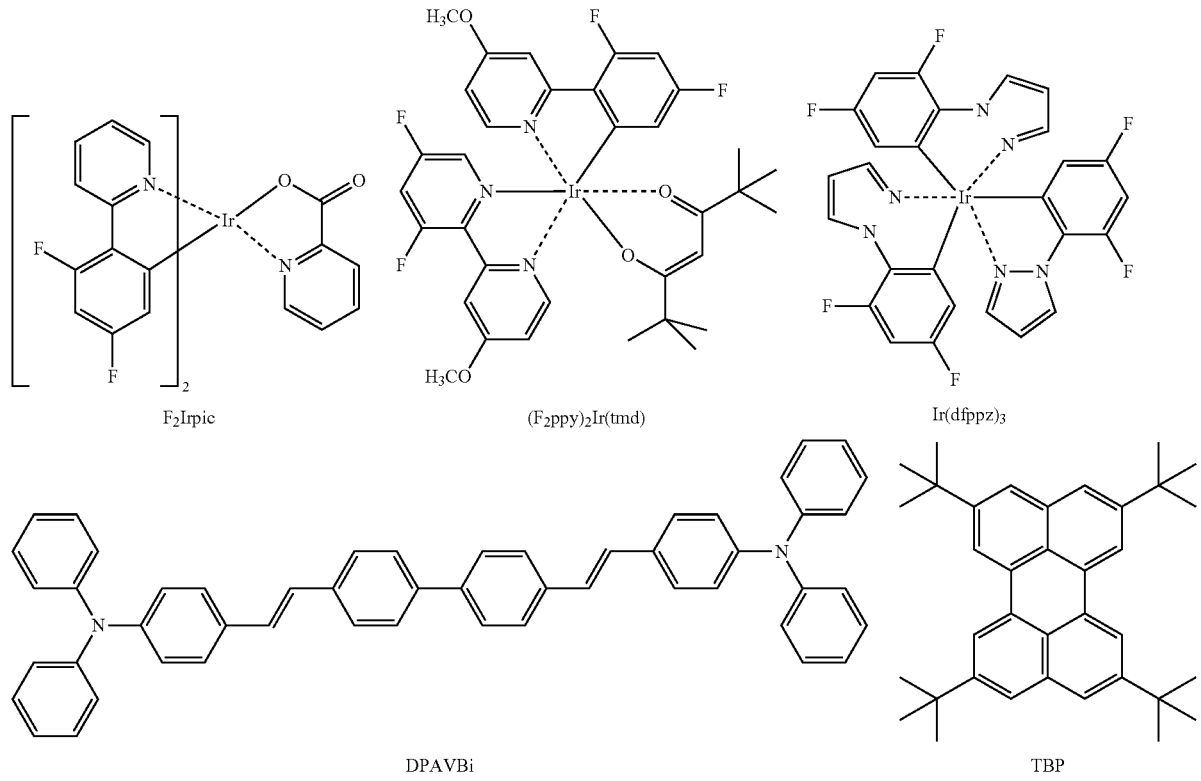

F₂Irpic  (F₂ppy)₂Ir(tmd)  Ir(dfppz)₃

DPAVBi  TBP

-continued

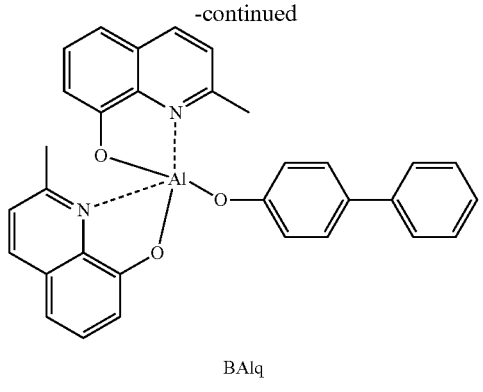

BAlq

An electron transport layer (ETL) of an organic light emitting diode device according to one embodiment may include an electron transport organic compound and a metal-containing material.

Non-limiting examples of the electron transport organic compound may include 9,10-di(naphthalen-2-yl)anthracene (ADN); and an anthracene-based compound such as the following compounds 101 or 102, but are not limited thereto.

Compound 101

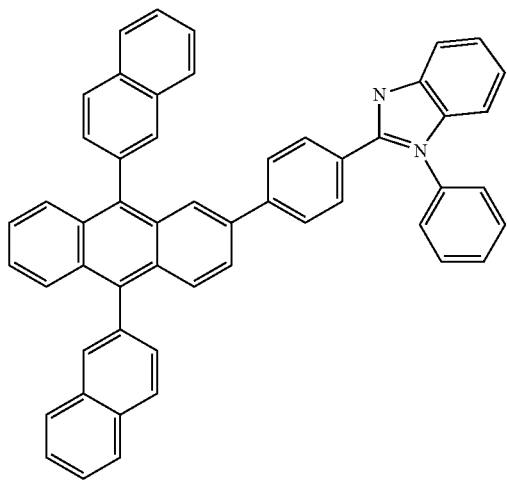

Compound 102

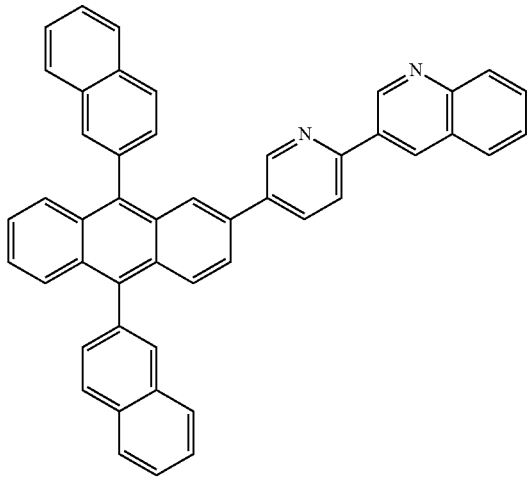

The metal-containing material may include a Li complex. Non-limiting examples of the Li complex may be lithium quinolate (LiQ) and the following compound 103, but are not limited thereto.

Compound 103

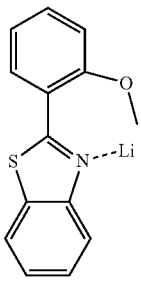

Hereinafter, an organic light emitting device according to one embodiment is described with reference to FIG. 3.

Referring to FIG. 3, an organic light emitting device according to another embodiment includes an anode 10, a cathode 20 facing the anode 10, an organic layer 50 interposed between the anode 10 and the cathode 20, a hole transport layer (HTL) 30 interposed between the anode 10 and the emission layer 50, and an electron transport layer (ETL) 40 interposed between the cathode 20 and the emission layer 50, like the above embodiment.

However, the organic light emitting device according to the present embodiment further includes a hole injection layer (HIL) 60 interposed between the anode 10 and the hole transport layer (HTL) 30, and an electron injection layer (EIL) 70 interposed between the cathode 20 and the electron transport layer (ETL) 40, unlike the above embodiment.

The hole injection layer (HIL) 60 may include a suitable hole injection material, for example, a phthalocyanine compound such as copperphthalocyanine or the like, m-MTDATA [4,4',4"-tris(3-methylphenylphenylamino)triphenylamine], NPB (N,N'-di(1-naphthyl)-N,N'-diphenylbenzidine), TDATA, 2T-NATA, Pani/DBSA (polyaniline/dodecylbenzenesulfonic acid), PEDOT/PSS (poly(3,4-ethylenedioxythiophene)/poly(4-styrenesulfonate)), Pani/CSA (polyaniline/camphor sulfonicacid), or PANI/PSS (polyaniline/poly(4-styrenesulfonate)), or the like, without being limited thereto.

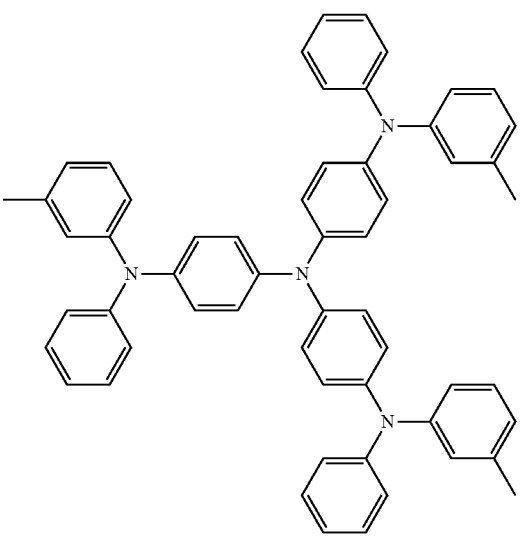

m-MTDATA

-continued

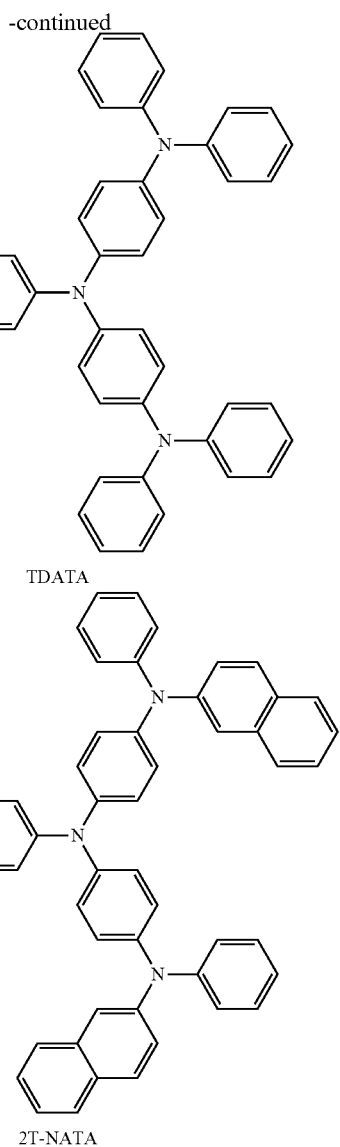

TDATA

2T-NATA

The hole injection layer (HIL) 60 may further include the above described p-dopant so as to improve the film conductivity.

When the hole injection layer (HIL) 60 further include the p-dopant, the p-dopant may be, for example, uniformly dispersed in the layer or layers or randomly distributed in the layer or layers.

The hole injection layer (HIL) 60 may be, for example, formed on the anode 10 according to various suitable methods such as vacuum deposition, spin coating, casting, or LB.

When the hole injection layer (HIL) 60 is formed by vacuum deposition, the deposition conditions may be different according to the compound used (utilized) as the material for the hole injection material, the structure of the objective hole injection layer (HIL), and/or the thermal characteristics, but generally, may be appropriately selected from a deposit temperature of about 100 to about 500° C., a vacuum degree of about $10^{-8}$ to about $10^{-3}$ torr, and a deposition rate of about 0.01 to about 100 Å/sec, without being limited thereto.

When the hole injection layer (HIL) 60 is formed by spin coating, the coating conditions may be different according to the compound used (utilized) as the material for the hole injection layer (HIL), the structure of the objective hole injection layer (HIL), the thermal characteristics, or the like, but may be suitably selected from a coating speed of about 2000 rpm to about 5000 rpm, and a heat treatment temperature of about 80° C. to about 200° C. for removing the solvent after coating, without being limited thereto.

When the emission layer 50 includes a phosphorescent dopant, a hole blocking layer may be formed on the emission layer 50 so as to reduce or prevent the diffusion of triplet excitons or holes into the electron transport layer (ETL).

Herein, a usable hole blocking material is not particularly limited, and any suitable hole blocking materials may be optionally used (utilized).

For example, the hole blocking material may be an oxadiazole derivative, a triazole derivative, a phenanthroline derivative, Balq, BCP, or the like.

On the electron transport layer (ETL) 40, an electron injection layer (EIL) 70 capable of easily injecting electrons from a cathode may be deposited.

The electron injection layer (EIL) 70 may be formed by using (utilizing) any suitable material such as LiF, NaCl, CsF, $Li_2O$, BaO, or the like, known for forming the electron injection layer (EIL).

The electron injection layer (EIL) 70 is in general formed under almost the same deposition and coating conditions as those for forming the hole injection layer (HIL) 60, but the conditions may vary depending on the compound used (utilized).

An organic light emitting diode device according to one embodiment may have a structure of anode/hole injection layer (HIL)/emission layer/cathode, anode/hole injection layer (HIL)/hole transport layer (HTL)/emission layer/electron transport layer (ETL)/cathode, or anode/hole injection layer (HIL)/hole transport layer (HTL)/emission layer/electron transport layer (ETL)/electron injection layer (EIL)/cathode.

In addition, the organic light emitting diode device may have a structure of anode/functional layer concurrently (e.g., simultaneously) having a hole injection function and a hole transport function/emission layer/electron transport layer (ETL)/cathode, or anode/functional layer concurrently (e.g., simultaneously) having a hole injection function and a hole transport function/emission layer/electron transport layer (ETL)/electron injection layer (EIL)/cathode.

Alternatively, the organic light emitting diode device may have a structure of anode/hole transport layer (HTL)/emission layer/functional layer concurrently (e.g., simultaneously) having an electron injection function and an electron transport function/cathode, anode/hole injection layer (HIL)/emission layer/functional layer concurrently (e.g., simultaneously) having an electron injection function and an electron transport function/cathode, or anode/hole injection layer (HIL)/hole transport layer (HTL)/emission layer/functional layer concurrently (e.g., simultaneously) having an electron injection function and an electron transport function/cathode.

The organic light emitting device may be electrically coupled (e.g., connected) to, for example, a thin film transistor, and herein, the thin film transistor may be disposed between the substrate and an electrode.

In addition, according to one embodiment, the layer (e.g., first layer) in the organic light emitting device may be formed by depositing the organic compound (according to one or more of the above described embodiments); or according to another embodiment, the layer in the organic light emitting device may be formed by coating the organic compound (according to one or more of the above described embodiments) prepared as a solution in a wet method.

Yet another embodiment provides a display device including an organic light emitting device according to the above embodiments.

Hereinafter, the present disclosure is illustrated in more detail with reference to examples.

However, these examples are exemplary, and the present disclosure is not limited thereto.

Manufacture of Organic Light Emitting Device

EXAMPLE 1

In order to manufacture an anode, a 15 Ω/cm² (500 Å) ITO glass substrate (Corning Inc.) was cut into a size of 50 mm×50 mm×0.5 mm, washed with an ultrasonic wave by using (utilizing) isopropyl alcohol for 10 minutes and pure water for 10 minutes, radiated by ultraviolet (UV) for 10 minutes, exposed to an ozone, and then, washed again. Then, the glass substrate was mounted on a vacuum deposition device.

Subsequently, 2-TNATA was vacuum-deposited on the glass substrate to form a 600 Å-thick hole injection layer (HIL); and 4,4'-bis[N-(1-naphthyl)-N-phenylamino]biphenyl (hereinafter, NPB) as a hole transport compound was vacuum-deposited on the hole injection layer (HIL) to form a 300 Å-thick hole transport layer (HTL).

Subsequently, one host (material) was prepared by mixing a compound represented by the following formula 1 (a host A) and a compound represented by the following formula 69 (a host B).

Then, the hosts A and B along with (piq)₂Ir(acac) [bis-(1-phenylisoquinolyl)iridium (III) acetylacetonate] (D1) as a red phosphorescent dopant were concurrently (e.g., simultaneously) deposited in a weight ratio of 45:45:10 to form a 300 Å-thick emission layer on the hole transport layer (HTL) (hosts A:hosts B:red phosphorescent dopant=45:45:10).

Subsequently, Alq₃ was deposited on the emission layer to form a 300 Å-thick electron transport layer (ETL); and Al was vacuum-deposited on the electron transport layer (ETL) to form a 1200 Å-thick Al electrode (a cathode), thereby complete the manufacturing of an organic light emitting device.

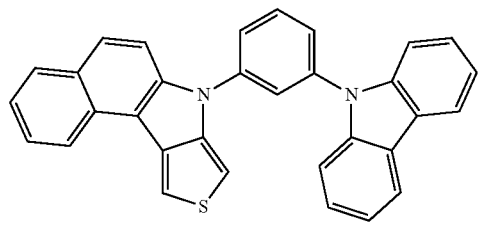

The organic light emitting device had a color coordinate of (0.66, 0.32), and a luminous efficiency of 70.5 cd/A at a current density of 10 MA/cm², a driving voltage of 4 V, and a light emitting luminance of 3700 cd/m², and thus, showed high efficiency.

EXAMPLE 2

An organic light emitting device was manufactured according to the same method as Example 1 except for using (utilizing) the dopant: the host A: the host B in a weight ratio of 10:30:60.

EXAMPLE 3

An organic light emitting device was manufactured according to the same method as Example 1 except for using (utilizing) the dopant: the host A: the host B in a weight ratio of 10:60:30.

EXAMPLE 4

An organic light emitting device was manufactured according to the same method as Example 1 except for using (utilizing) a compound represented by the following formula 2 as the host A and a compound represented by the following formula 70 as the host B.

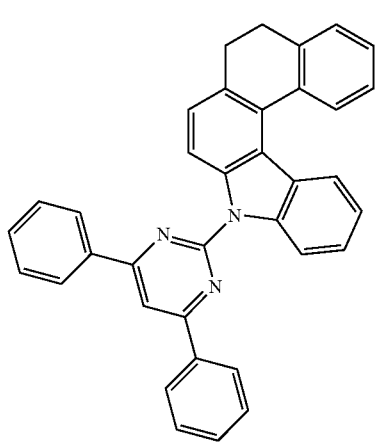

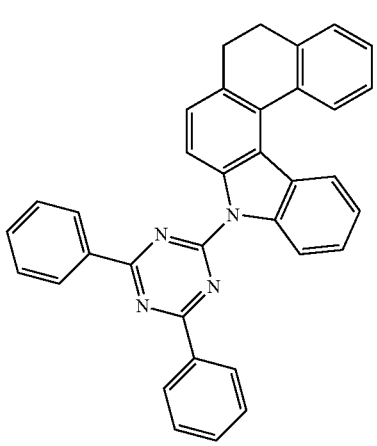

EXAMPLE 5

An organic light emitting device was manufactured according to the same method as Example 4 except for using (utilizing) the dopant: the host A: the host B in a weight ratio of 10:30:60.

EXAMPLE 6

An organic light emitting device was manufactured according to the same method as Example 4 except for using (utilizing) the dopant: the host A: the host B in a weight ratio of 10:60:30.

EXAMPLE 7

An organic light emitting device was manufactured according to the same method as Example 1 except for using (utilizing) a compound represented by the following formula 5 as the host A and a compound represented by the following formula 80 as the host B.

EXAMPLE 8

An organic light emitting device was manufactured according to the same method as Example 4 except for using (utilizing) the dopant: the host A: the host B in a weight ratio of 10:30:60.

EXAMPLE 9

An organic light emitting device was manufactured according to the same method as Example 4 except for using (utilizing) the dopant: the host A: the host B in a weight ratio of 10:60:30.

The evaluation results of the organic light emitting devices according to Examples 1 to 9 are provided in Table 1.

TABLE 1

| | host A | host B | dopant | mixing ratio (A:B) | dopant ratio | luminance | voltage (V) | efficiency (cd/A) | life-span (T90%) |
|---|---|---|---|---|---|---|---|---|---|
| Example 1 | 1 | 69 | D1 | 45:45 | 10 | 3700 | 4 | 70.5 | 1000 |
| Example 2 | 1 | 69 | D1 | 30:60 | 10 | 3700 | 4.5 | 63.1 | 1350 |
| Example 3 | 1 | 69 | D1 | 60:30 | 10 | 3700 | 4.8 | 60.2 | 1000 |
| Example 4 | 2 | 70 | D1 | 45:45 | 10 | 3700 | 4.2 | 68.5 | 1500 |
| Example 5 | 2 | 70 | D1 | 30:60 | 10 | 3700 | 4.8 | 60.5 | 1400 |
| Example 6 | 2 | 70 | D1 | 60:30 | 10 | 3700 | 4.3 | 59.8 | 1100 |
| Example 7 | 5 | 80 | D1 | 45:45 | 10 | 3700 | 4.1 | 70.2 | 1710 |
| Example 8 | 5 | 80 | D1 | 30:60 | 10 | 3700 | 4.9 | 66.1 | 1200 |
| Example 9 | 5 | 80 | D1 | 60:30 | 10 | 3700 | 4.4 | 65.3 | 1100 |

Referring to Table 1, the organic light emitting devices according to Examples 1 to 9 had excellent efficiency characteristics and life-span characteristics.

REFERENCE EXAMPLE 1

An organic light emitting device was manufactured according to the same method as Example 1 by depositing Ir(ppy)3 as a phosphorescence dopant and a compound represented by the following formula 1 in a weight ratio of 13:87 to form the emission layer.

The organic light emitting device showed a driving voltage of 4.8 V at a current density of 6.1 mA/cm², a luminous efficiency of 16.5 cd/A at a light emitting luminance of 1000 cd/m², and green light emission.

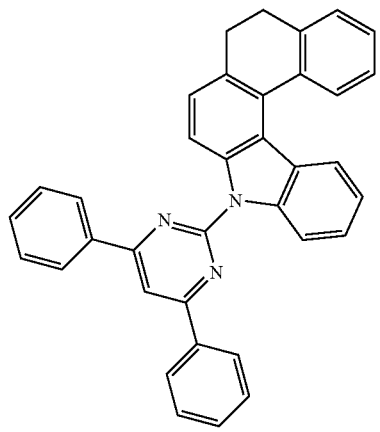

1

REFERENCE EXAMPLE 2

An organic light emitting device was manufactured according to the same method as Reference Example 1 except for using (utilizing) a compound represented by the following formula 4 instead of the compound represented by formula 1 to form the emission layer.

The organic light emitting device showed a driving voltage of 5.2 V at a current density of 6.7 mA/cm², and a luminous efficiency of 17.4 cd/A at a light emitting luminance of 1000 cd/m², and green light emission.

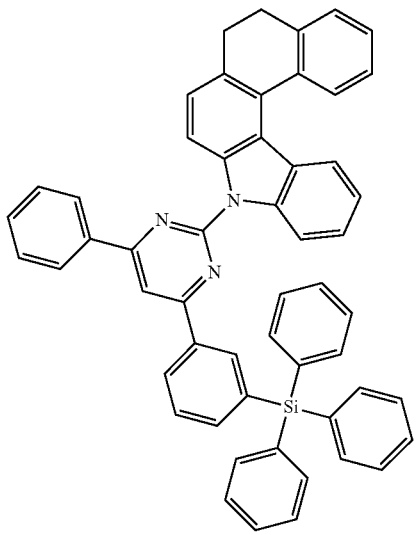

4

REFERENCE EXAMPLE 3

An organic light emitting device was manufactured according to the same method as Reference Example 1 except for using (utilizing) a compound represented by the following formula 6 instead of the compound represented by formula 1 to form the emission layer.

The organic light emitting device showed a driving voltage of 5.5 V at a current density of 5.8 mA/cm², and a luminous efficiency of 14.7 cd/A at a light emitting luminance of 1000 cd/m², and green light emission.

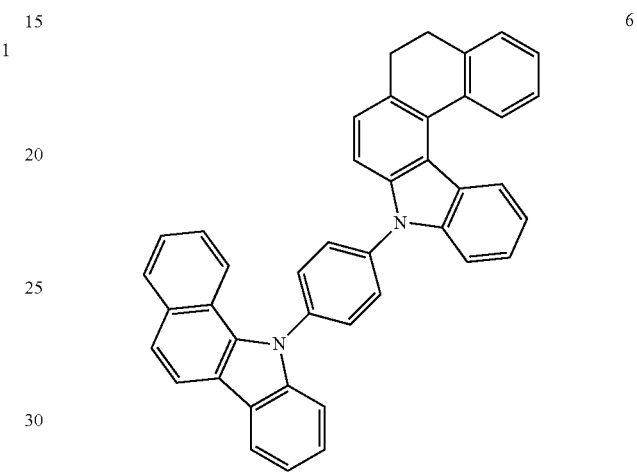

6

REFERENCE EXAMPLE 4

An organic light emitting device was manufactured according to the same method as Reference Example 1 except for using (utilizing) a compound represented by the following formula 9 instead of the compound represented by formula 1 to form the emission layer.

The organic light emitting device showed a driving voltage of 5.7 V at a current density of 5.5 mA/cm², and a luminous efficiency of 12.5 cd/A at a light emitting luminance of 1000 cd/m², and green light emission.

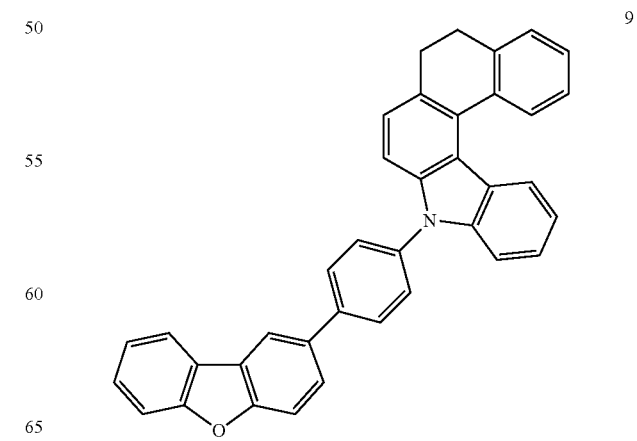

9

REFERENCE EXAMPLE 5

A light emitting device was manufactured according to the same method as Reference Example 1 except for using (utilizing) a compound represented by the following formula 10 instead of the compound represented by formula 1 to form the emission layer.

The organic light emitting device showed a driving voltage of 6.0 V at a current density of 6.9 mA/cm$^2$, and a luminous efficiency of 15.9 cd/A at a light emitting luminance of 1000 cd/m$^2$, and green light emission.

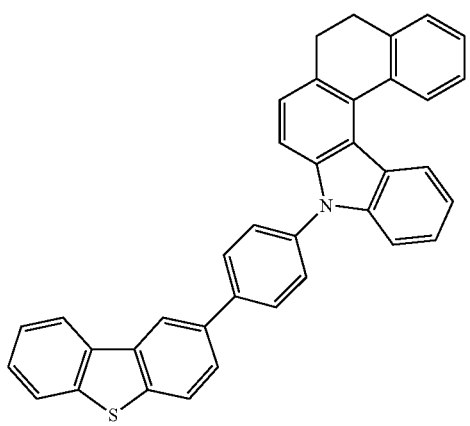

10

REFERENCE EXAMPLE 6

An organic light emitting device was manufactured according to the same method as Reference Example 1 except for using (utilizing) a compound represented by the following formula 16 instead of the compound represented by formula 1 to form the emission layer.

The organic light emitting device showed a driving voltage of 6.1 V at a current density of 6.2 mA/cm$^2$, and a luminous efficiency of 13.9 cd/A at a light emitting luminance of 1000 cd/m$^2$, and green light emission.

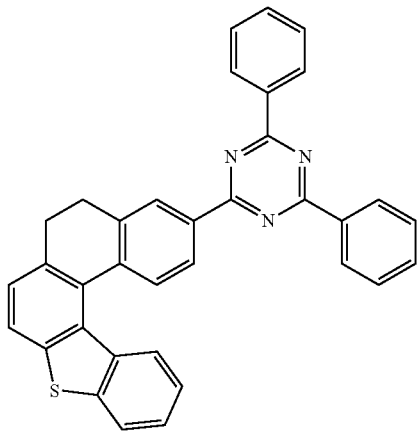

16

REFERENCE EXAMPLE 7

An organic light emitting device was manufactured according to the same method as Reference Example 1 except for using (utilizing) a compound represented by the following formula 17 instead of the compound represented by formula 1 to form the emission layer.

The organic light emitting device showed a driving voltage of 5.0 V at a current density of 5.2 mA/cm$^2$, and a luminous efficiency of 13.1 cd/A at a light emitting luminance of 1000 cd/m$^2$, and green light emission.

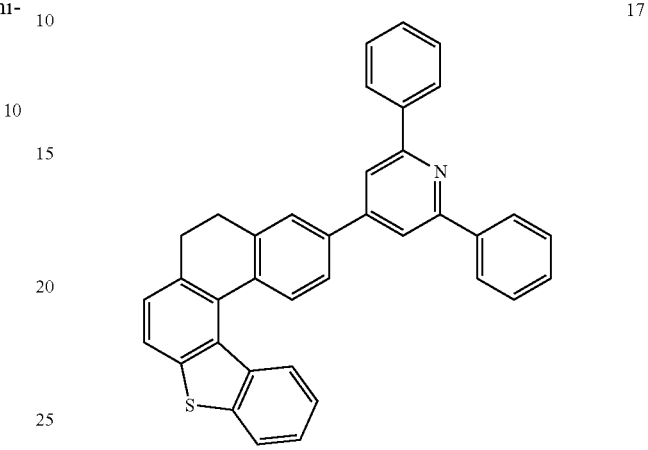

17

REFERENCE EXAMPLE 8

An organic light emitting device was manufactured according to the same method as Reference Example 1 except for using (utilizing) a compound represented by the following formula 18 instead of the compound represented by formula 1 to form the emission layer.

The organic light emitting device showed a driving voltage of 6.9 V at a current density of 6.6 mA/cm$^2$, and a luminous efficiency of 16.4 cd/A at a light emitting luminance of 1000 cd/m$^2$, and green light emission.

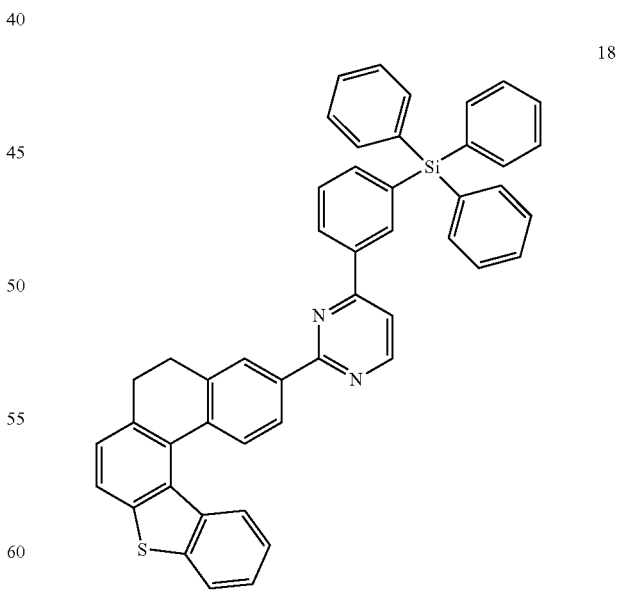

18

REFERENCE EXAMPLE 9

An organic light emitting device was manufactured according to the same method as Reference Example 1 except for using (utilizing) a compound represented by the following formula 19 instead of the compound represented by formula 1 to form the emission layer.

The organic light emitting device showed a driving voltage of 5.1 V at a current density of 6.7 mA/cm², and a luminous efficiency of 17.0 cd/A at a light emitting luminance of 1000 cd/m², and green light emission.

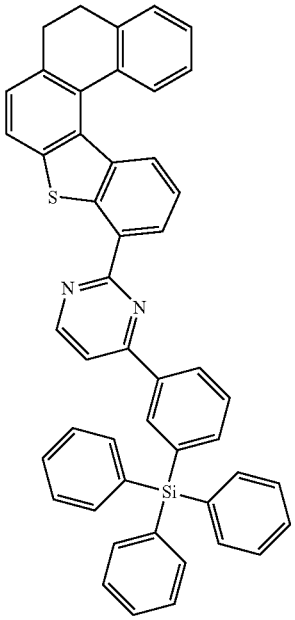

19

REFERENCE EXAMPLE 10

An organic light emitting device was manufactured according to the same method as Reference Example 1 except for using (utilizing) a compound represented by the following formula 25 instead of the compound represented by formula 1 to form the emission layer.

The organic light emitting device showed a driving voltage of 5.9 V at a current density of 7.1 mA/cm², and a luminous efficiency of 15.1 cd/A at a light emitting luminance of 1000 Cd/m², and green light emission.

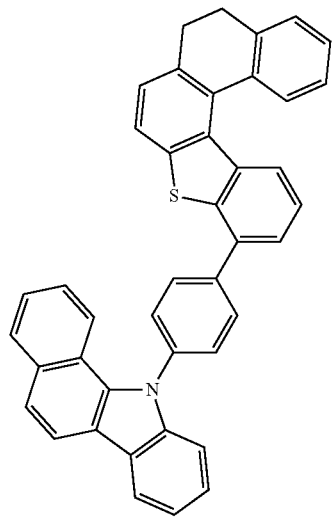

25

REFERENCE EXAMPLE 11

An organic light emitting device was manufactured according to the same method as Reference Example 1 except for using (utilizing) a compound represented by the following formula 29 instead of the compound represented by formula 1 to form the emission layer.

The organic light emitting device showed a driving voltage of 6.7 V at a current density of 5.29 mA/cm², and a luminous efficiency of 16.3 cd/A at a light emitting luminance of 1000 cd/m², and green light emission.

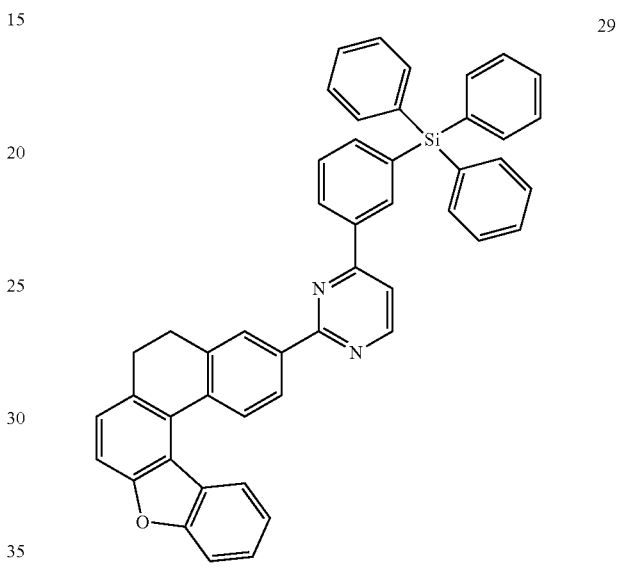

29

CONTRAST REFERENCE EXAMPLE 1

An organic light emitting device was manufactured according to the same method as Reference Example 1 except for using (utilizing) CBP as a host instead of the compound represented by formula 1 to form the emission layer, and bis(2-methyl-8-quinolinato)(p-phenylphenolreito) aluminum (III) (BAlq) to form the hole blocking layer.

The organic light emitting device showed a driving voltage of 7.8 V at a current density of 5.5 mA/cm², and a luminous efficiency of 11.2 cd/A at a light emitting luminance of 1000 cd/m², and green light emission.

CONTRAST REFERENCE EXAMPLE 2

An organic light emitting device was manufactured according to the same method as Reference Example 1 except for using (utilizing) the following compound A as a host instead of the compound represented by formula 1 to form the emission layer and bis(2-methyl-8-quinolinato)(p-phenylphenolreito)aluminum (Ill) (BAlq) to form the hole blocking layer.

The organic light emitting device showed a driving voltage of 6.8 V at a current density of 5.5 mA/cm², and a luminous efficiency of 15.2 cd/A at a light emitting luminance of 1000 cd/m², and green light emission.

Compound A

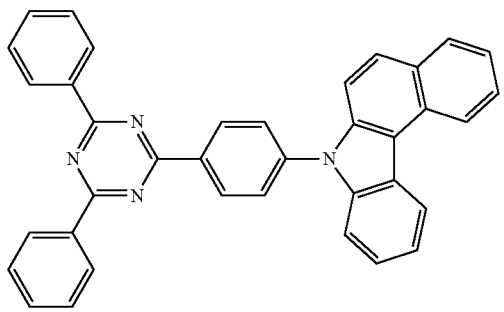

CONTRAST REFERENCE EXAMPLE 3

An organic light emitting device was manufactured according to the same method as Reference Example 1 except for using (utilizing) the following compound B as a host instead of the compound represented by formula 1 to form the emission layer, and bis(2-methyl-8-quinolinato)(p-phenylphenolreito)aluminum (Ill) (BAlq) to form the hole blocking layer.

The organic light emitting device showed a driving voltage of 8.1 V at a current density of 5.5 mA/cm$^2$, and a luminous efficiency of 18.4 cd/A at a light emitting luminance of 1000 cd/m$^2$, and green light emission.

Compound B

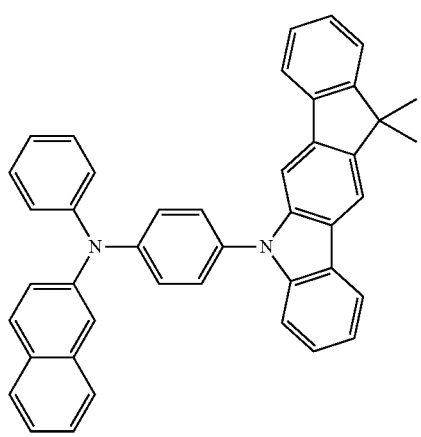

Life-span characteristics of the organic light emitting devices according to Reference Examples 1 to 11 and Contrast Reference Examples 1 to 3 are provided in Table 2.

TABLE 2

|  | light emitting material | T97 life-span (hr@100 mA/cm$^2$) |
| --- | --- | --- |
| Reference Example 1 | compound 1 | 970 |
| Reference Example 2 | compound 4 | 921 |
| Reference Example 3 | compound 6 | 943 |
| Reference Example 4 | compound 9 | 921 |
| Reference Example 5 | compound 10 | 991 |
| Reference Example 6 | compound 16 | 937 |
| Reference Example 7 | compound 17 | 897 |
| Reference Example 8 | compound 18 | 911 |
| Reference Example 9 | compound 19 | 956 |
| Reference Example 10 | compound 25 | 971 |

TABLE 2-continued

|  | light emitting material | T97 life-span (hr@100 mA/cm$^2$) |
| --- | --- | --- |
| Reference Example 11 | compound 29 | 923 |
| Contrast Reference Example 1 | CBP | 675 |
| Contrast Reference Example 2 | compound A | 866 |
| Contrast Reference Example 3 | compound B | 921 |

Referring to Table 2, when the compound according to one or more embodiments of the present invention was used (utilized) as a light emitting material, the compound showed excellent life-span characteristics and excellent electric stability and easily transported energy compared with a comparable light emitting material.

In addition, when the compound according to one or more embodiments of the present invention was used (utilized) as a light emitting material in the structure of a device, power consumption may be improved without a hole blocking layer by decreasing the driving voltage as well as realizing excellent light emitting characteristics and thus, increasing the power efficiency.

While this disclosure has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims, and equivalents thereof.

| Description of Symbols |
| --- |
| 10: anode    20: cathode |
| 30: hole transport layer (HTL) 40: electron transport layer (ETL) |
| 50: emission layer    60: hole injection layer (HIL) |
| 70: electron injection layer (EIL) |
| 100: organic layer |

What is claimed is:

1. A material for an organic light emitting device comprising:

a compound represented by one of the following Chemical Formulae 1 to 3; and a compound represented by the following Chemical Formula 4:

Chemical Formula 1

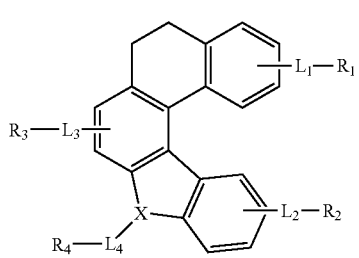

Chemical Formula 2

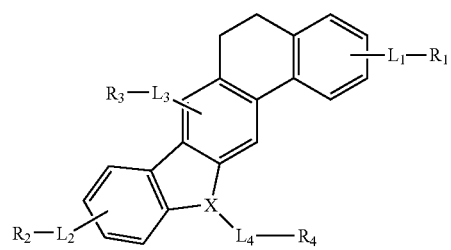

Chemical Formula 3

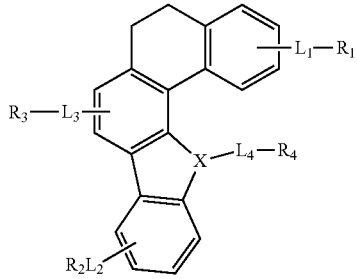

wherein, in the above Chemical Formulae 1 to 3, $L_1$ to $L_4$ are each independently a single bond, a substituted or unsubstituted C6 to C30 arylene group, a substituted or unsubstituted C3 to C30 heteroarylene group, or a combination thereof;

$R_1$ to $R_4$ are each independently hydrogen, deuterium, a substituted or unsubstituted C1 to C30 alkyl group, a substituted or unsubstituted C1 to C30 haloalkyl group, a halogen, a cyano group, a substituted or unsubstituted C3 to C30 cycloalkyl group, a substituted or unsubstituted C5 to C7 heterocycloalkyl group, a substituted or unsubstituted C2 to C30 alkenyl group, a substituted or unsubstituted C2 to C30 alkynyl group, a substituted or unsubstituted C6 to C30 aryl group, a substituted or unsubstituted C1 to C30 alkoxy group, a substituted or unsubstituted C6 to C30 aryloxy group, a substituted or unsubstituted C3 to C30 heteroaryl group, a nitro group, —P(=O)$R_aR_b$, —P(=S)$R_aR_b$, a hydroxyl group, or a combination thereof, wherein $R_a$ and $R_b$ are each independently a substituted or unsubstituted C6 to C30 aryl group, a substituted or unsubstituted C3 to C30 heteroaryl group, or a combination thereof; and X is N or S, provided that when X is N, *-$L_4$-$R_4$ is not hydrogen and when X is S, *-$L_4$-$R_4$ is not included;

Chemical Formula 4

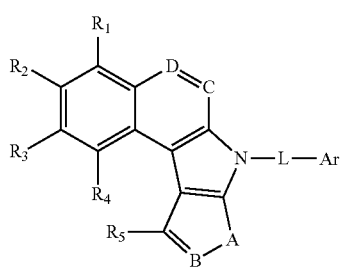

wherein, in the above Chemical Formula 4, $R_1$ to $R_5$ are each independently hydrogen, deuterium, a halogen, a substituted or unsubstituted C1 to C30 alkyl group, a substituted or unsubstituted C2 to C30 alkenyl group, a substituted or unsubstituted C2 to C30 alkynyl group, a substituted or unsubstituted C3 to C30 cycloalkyl group, a substituted or unsubstituted C1 to C30 alkoxy group, a substituted or unsubstituted C6 to C30 aryloxy group, a substituted or unsubstituted C6 to C30 arylthiol group, a substituted or unsubstituted C6 to C30 aryl group, a substituted or unsubstituted C2 to C30 heteroaryl group, a substituted or unsubstituted C1 to C30 amine group, a substituted or unsubstituted silyl group, a cyano group, a nitro group, a hydroxyl group, a carboxyl group, or a combination thereof;

A is $CH_2$, NH, O or S; B is N;

C and D are each independently N or CH;

L is a single bond, a substituted or unsubstituted C6 to C40 arylene group, or a substituted or unsubstituted C3 to C40 heteroarylene group; and Ar is a substituted or unsubstituted C6 to C40 aryl group, a substituted or unsubstituted C5 to C40 heterocycloalkyl group, a substituted or unsubstituted C3 to C40 heteroaryl group, or a combination thereof.

2. The material for the organic light emitting device of claim 1, wherein, in the above Chemical Formulae 1 to 3, $L_1$ to $L_4$ are each independently a substituted or unsubstituted C3 to C30 heteroarylene group; and $R_1$ to $R_4$ are each independently a substituted or unsubstituted C5 to C7 heterocycloalkyl group, a substituted or unsubstituted C3 to C30 heteroaryl group, or a combination thereof, wherein the heteroarylene group, heterocycloalkyl group and heteroaryl group each independently comprises at least one heteroatom selected from B, N, O, S, P and Si.

3. The material for the organic light emitting device of claim 1, wherein, in the above Chemical Formula 4, Ar is phenyl, biphenyl, terphenyl, naphthyl, anthracenyl, phenanthryl, pyrenyl, fluorenyl, carbazolyl, N-carbazolephenyl, quinolinyl, isoquinolinyl, or a combination thereof.

4. The material for the organic light emitting device of claim 1, wherein the compound represented by one of the above Chemical Formulae 1 to 3 is one selected from the following chemical structures 1 to 68 of Group 1:

Group 1

1

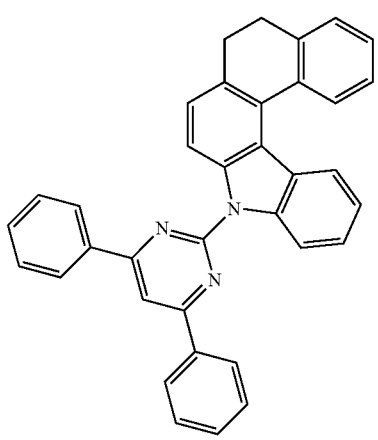

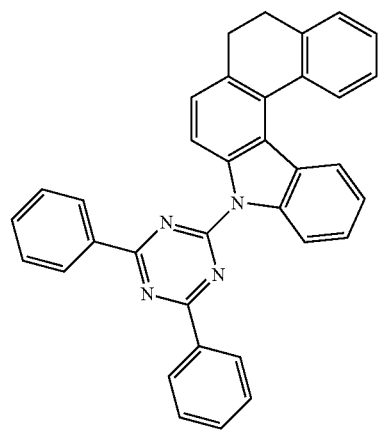
2
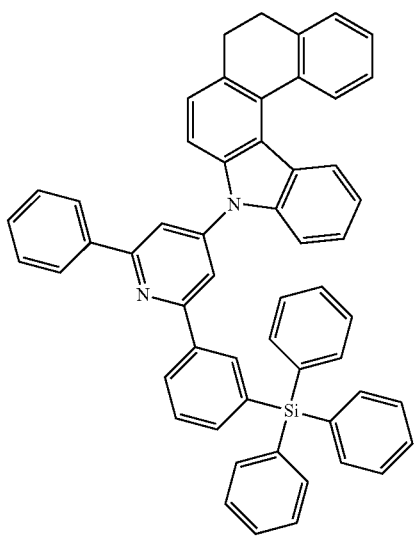
5
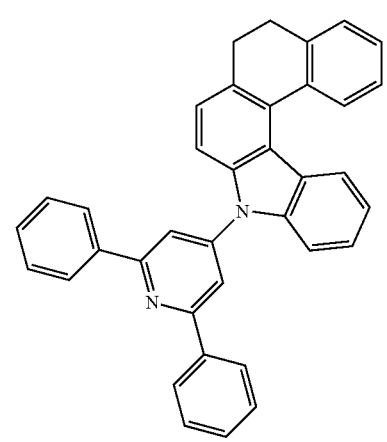
3
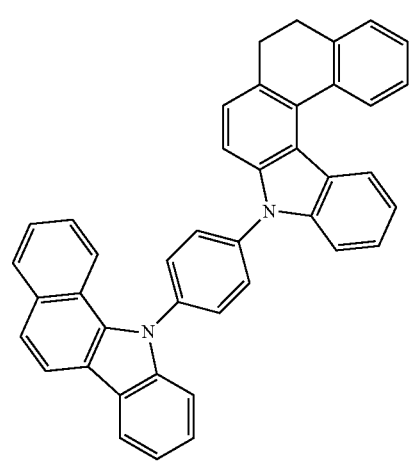
6
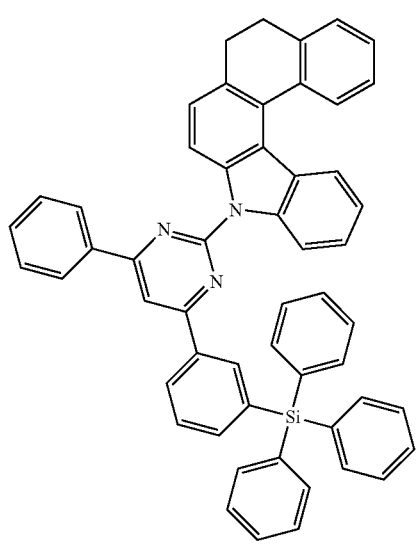
4
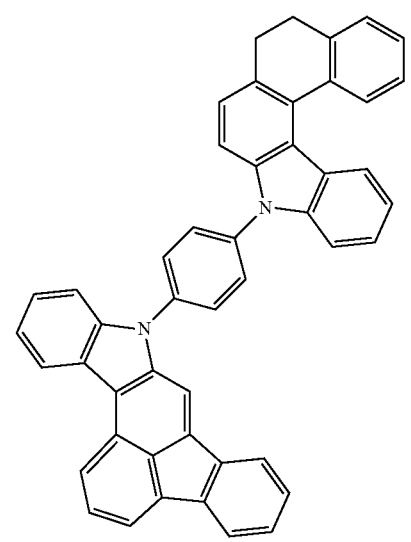
7

-continued
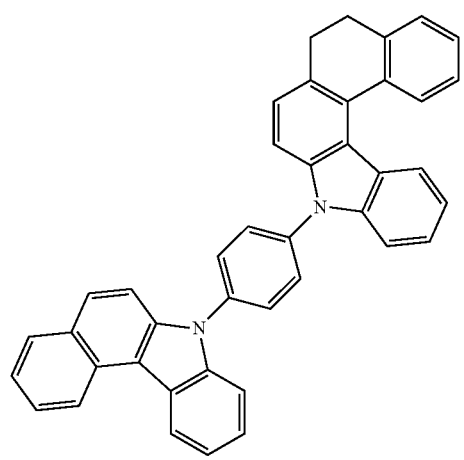
8
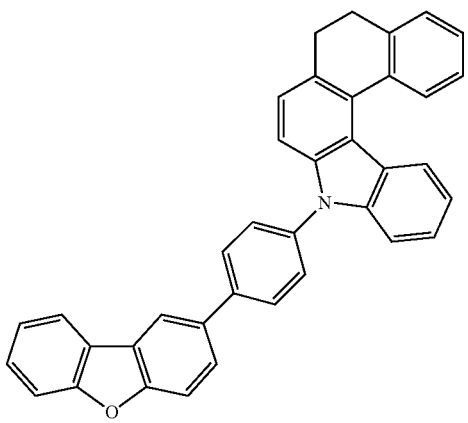
9
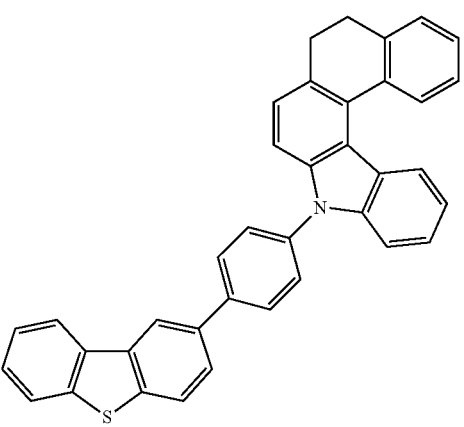
10
-continued
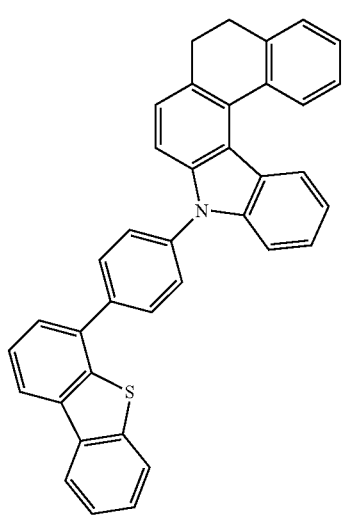
11
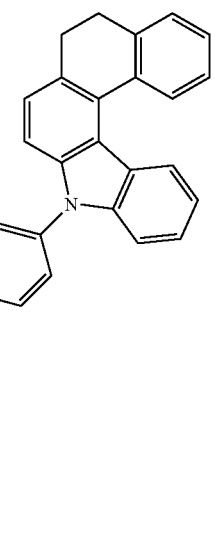
12
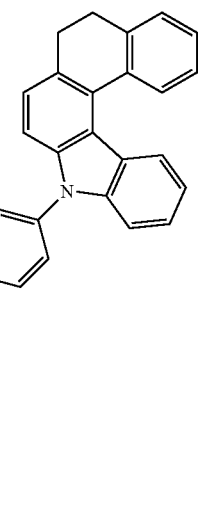
13

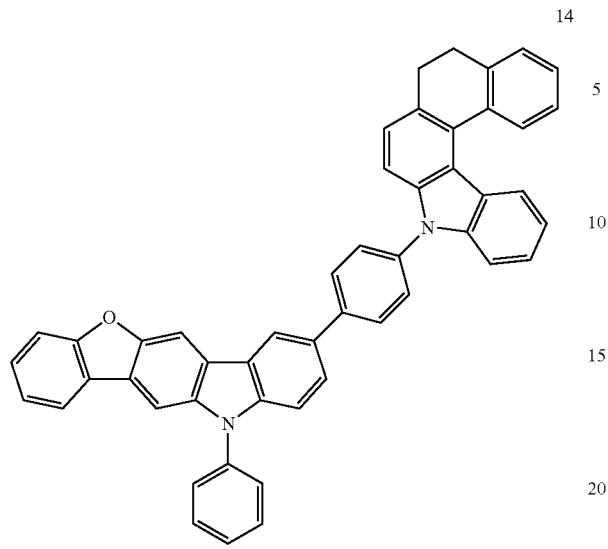
14
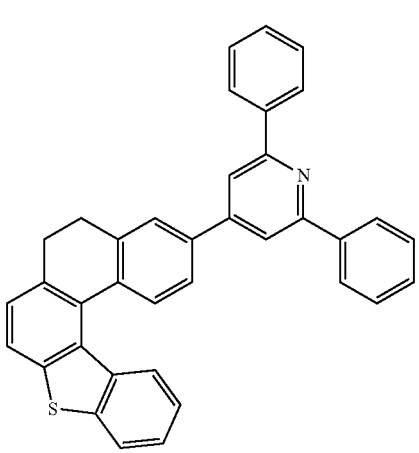
17
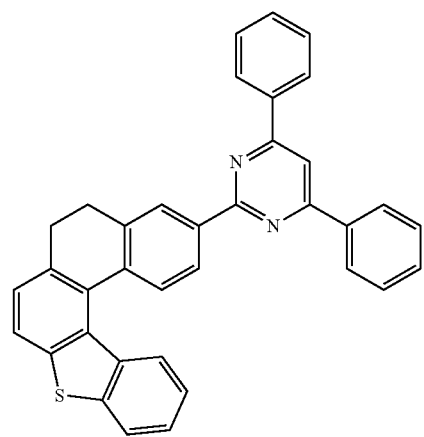
15
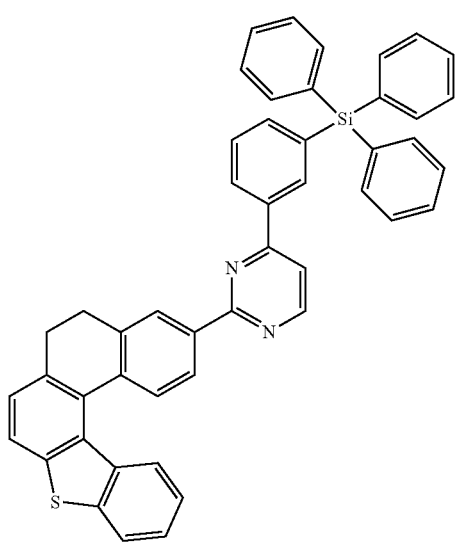
18
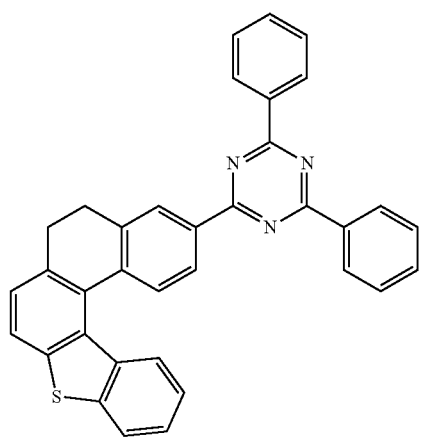
16
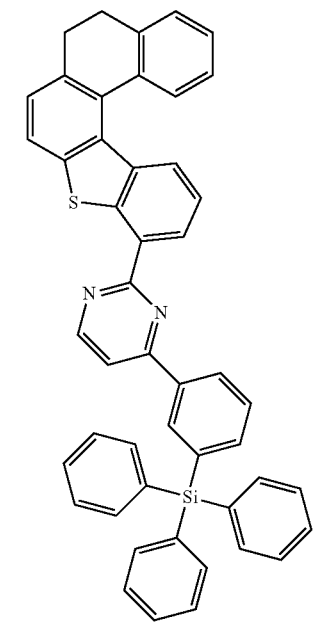
19

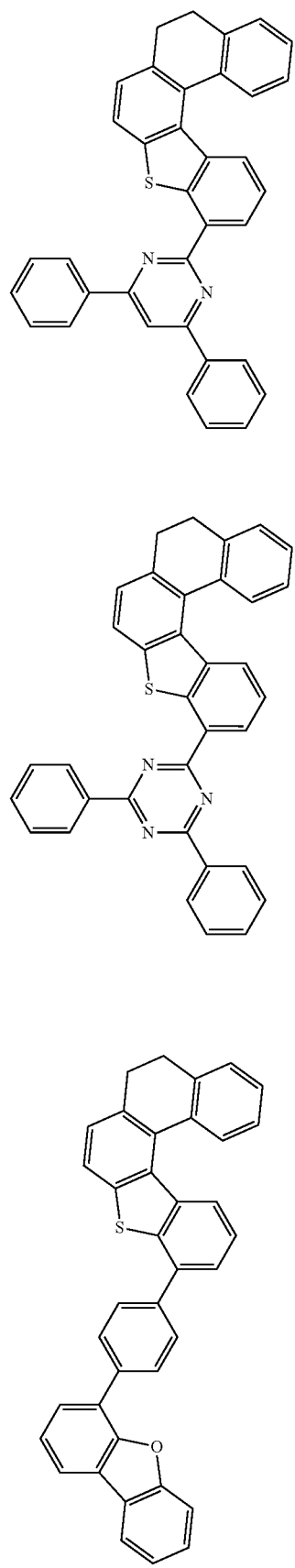
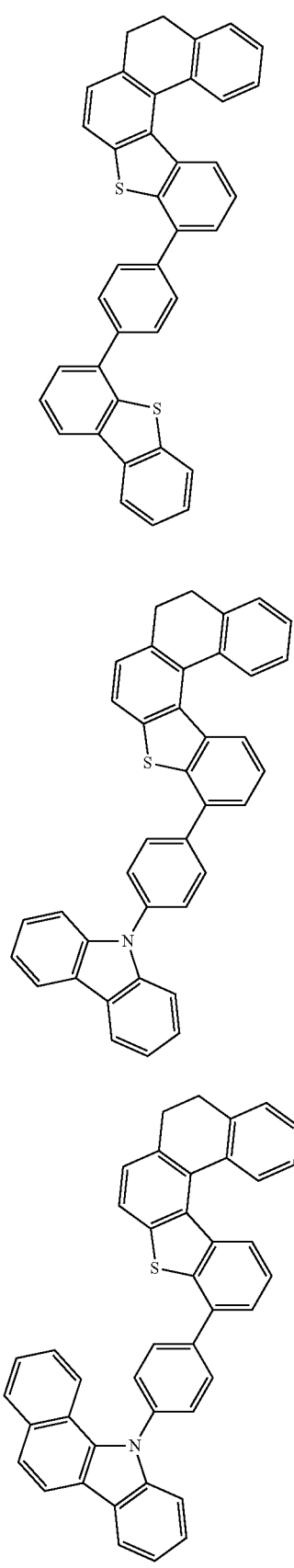

26
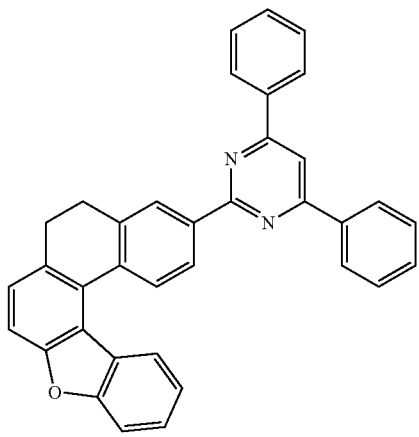
27
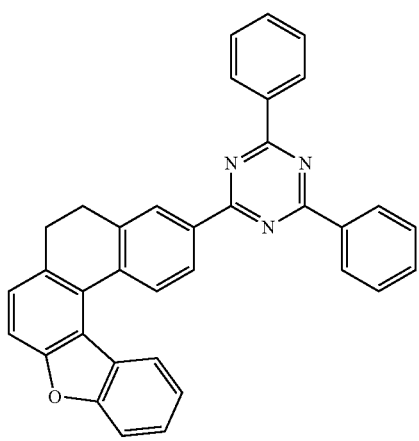
28
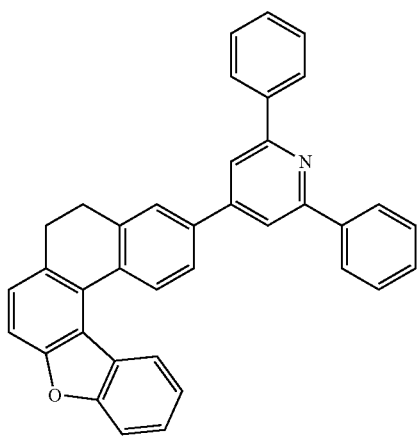
29
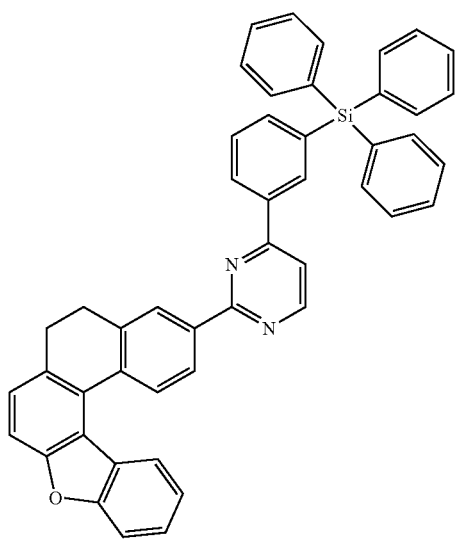
30
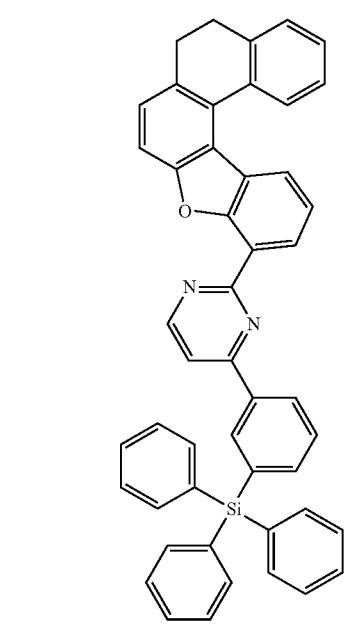
31
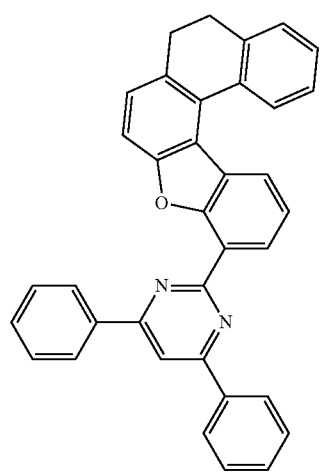

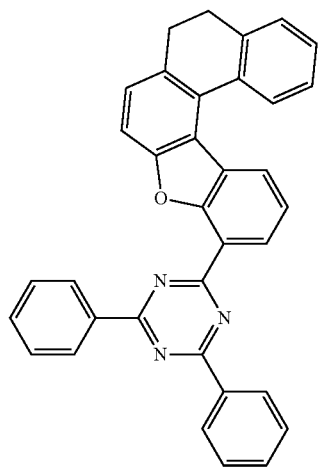
32
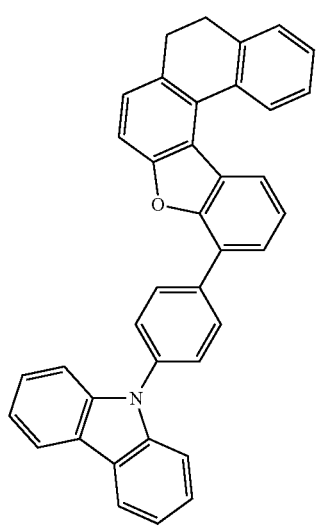
35
33
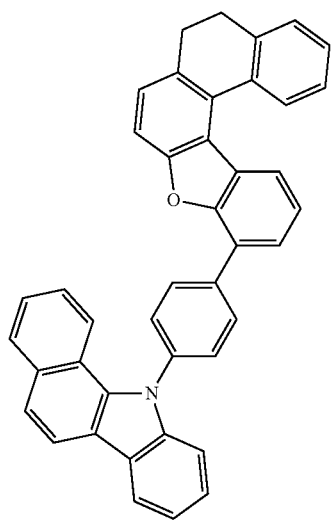
36
34
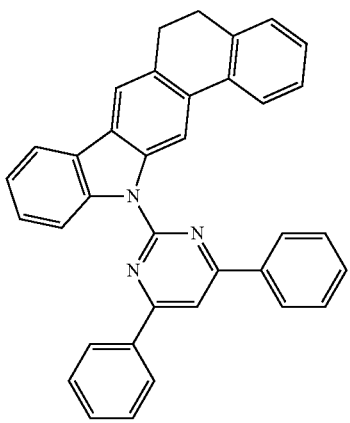
37

38
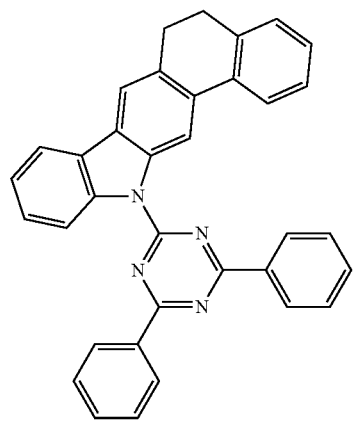
39
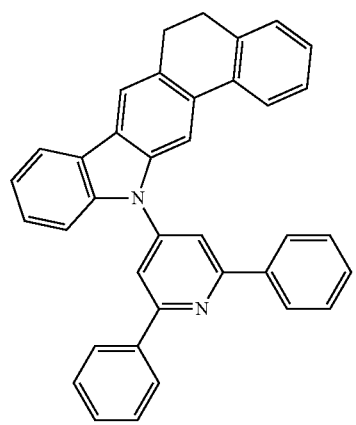
40
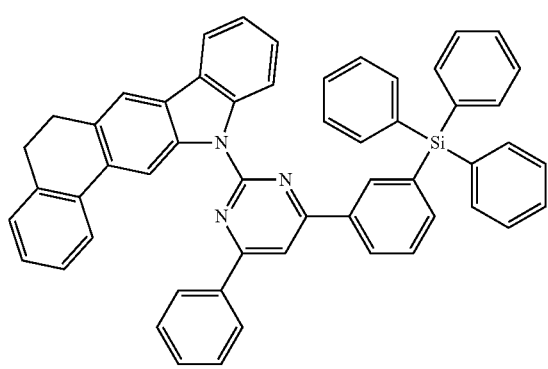
41
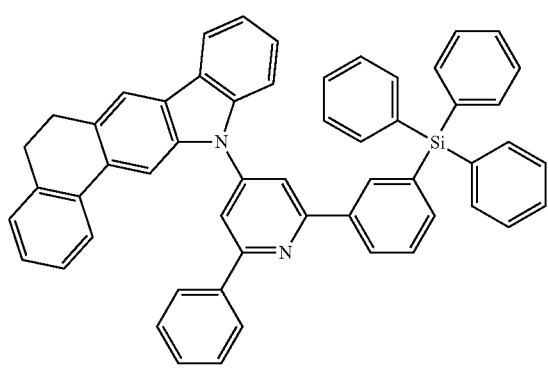
42
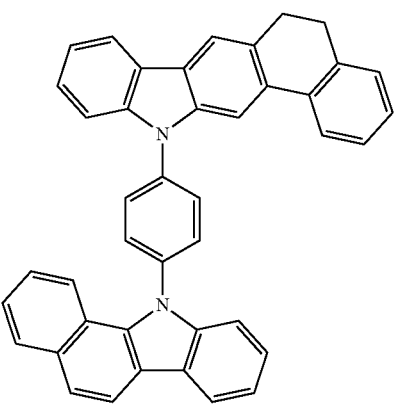
43
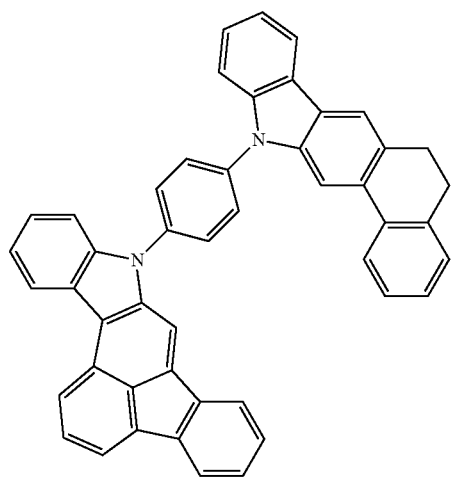
44
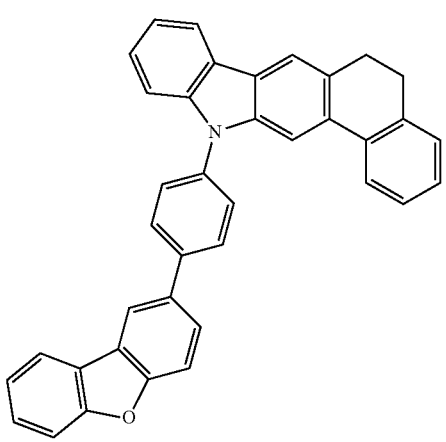

99
-continued
45
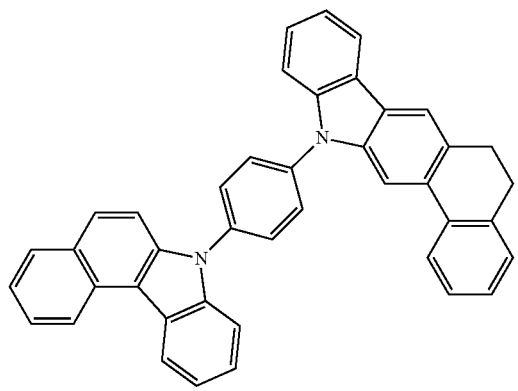
46
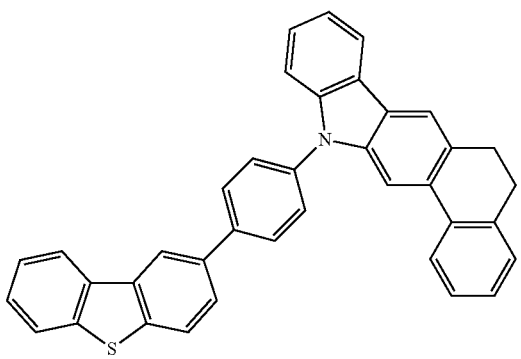
47
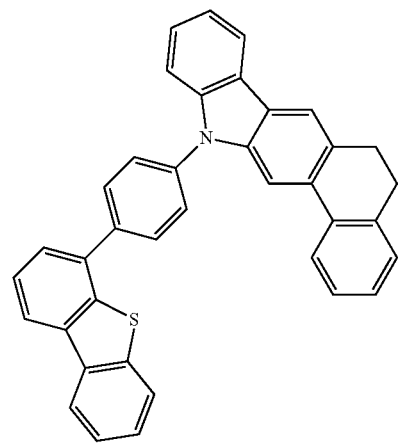
100
-continued
48
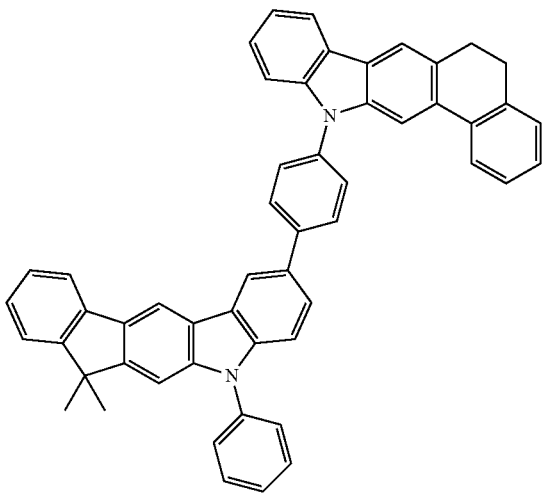
49
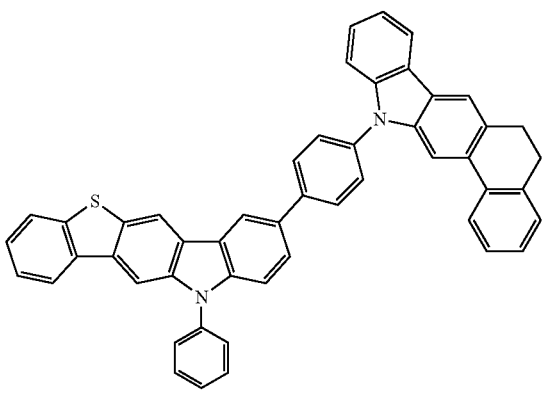
50
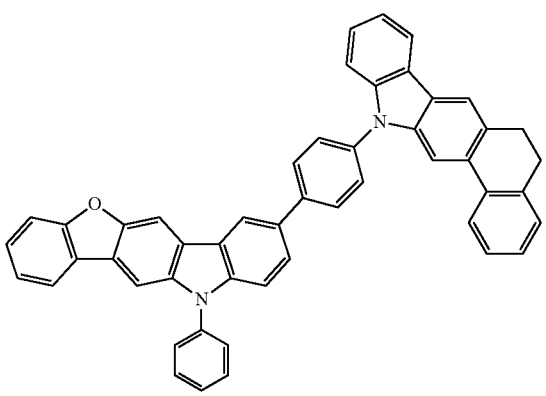

101
-continued
51
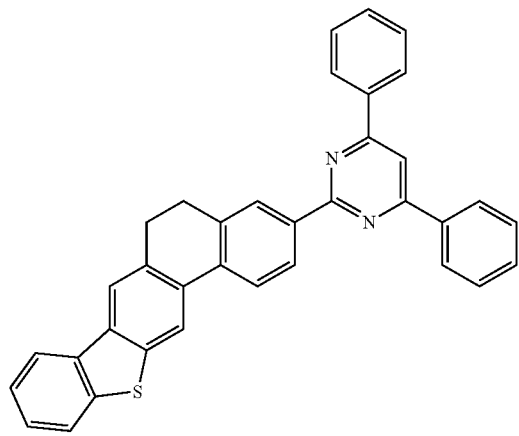
52
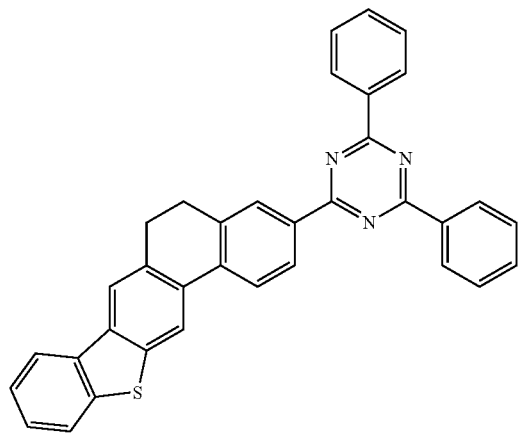
53
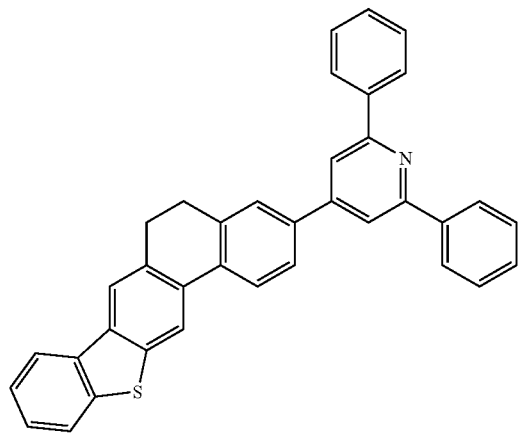
102
-continued
54
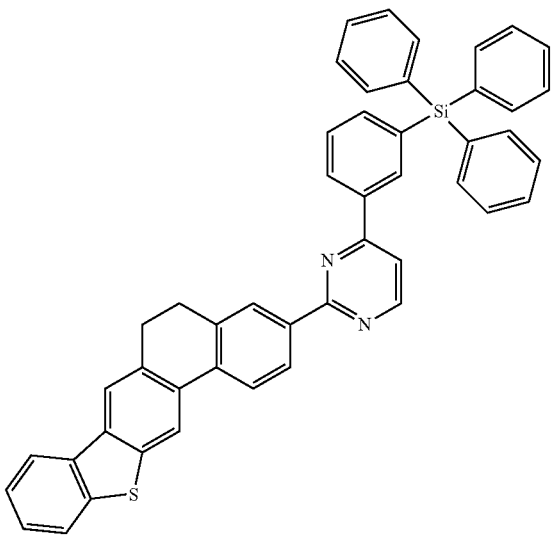
55
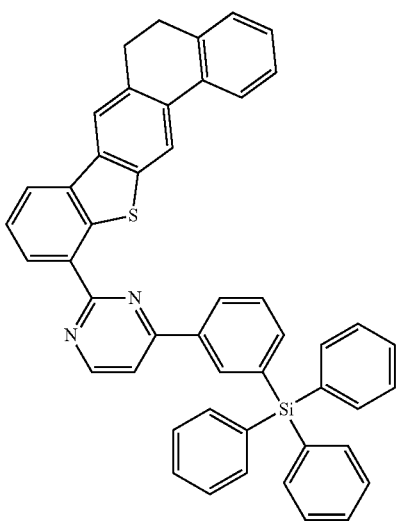
56
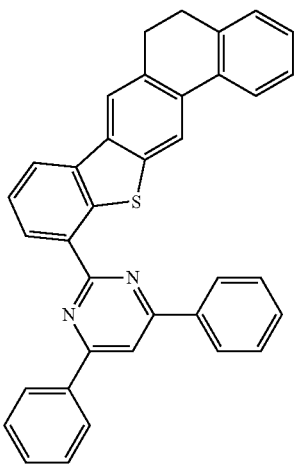

| 103 -continued | 104 -continued |
|---|---|
| 57 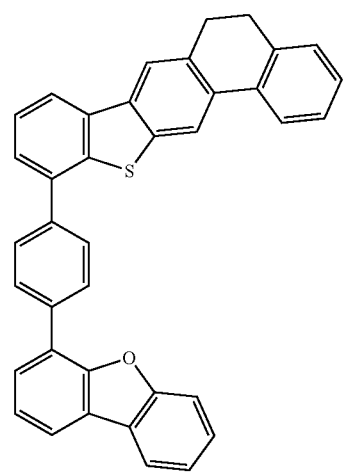 | 60 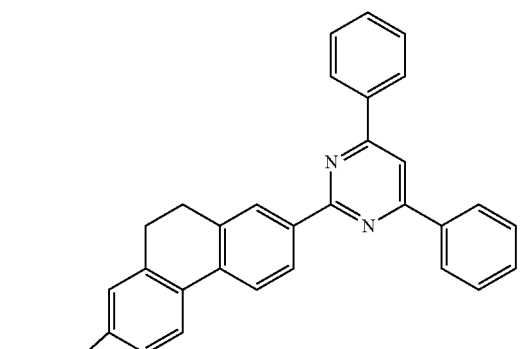 |
| 58 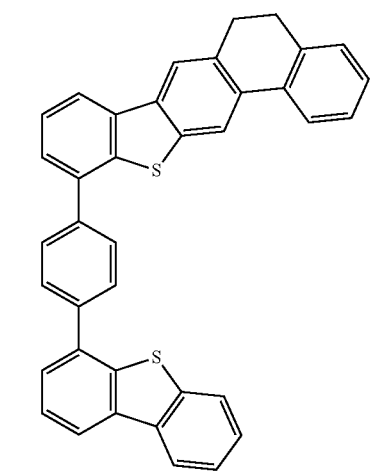 | 61 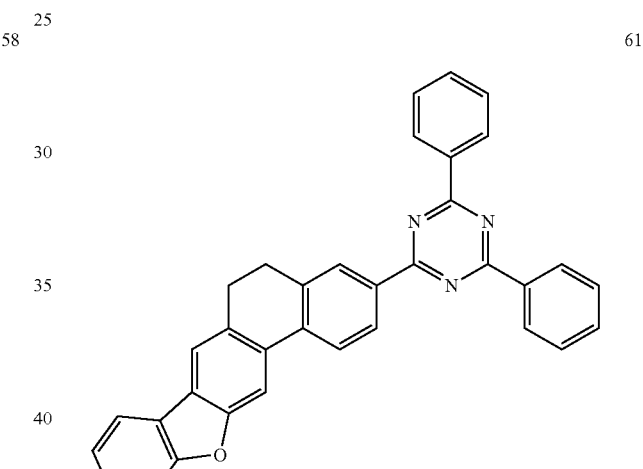 |
| 59 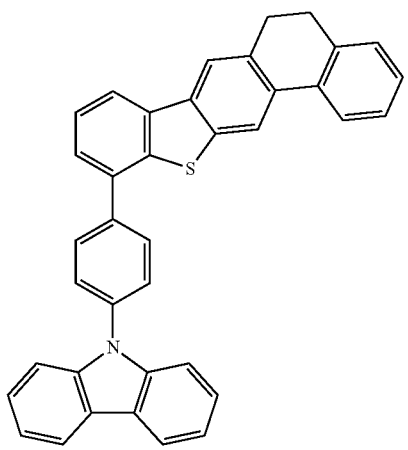 | 62 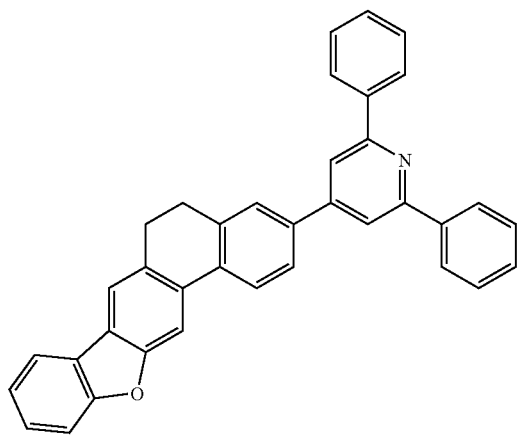 |

63
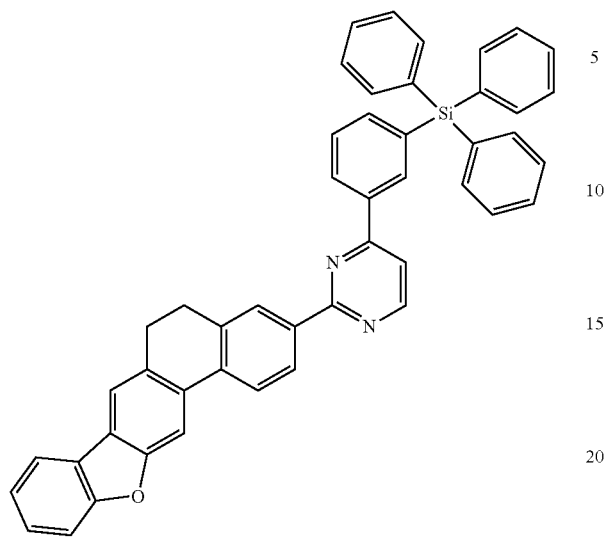
64
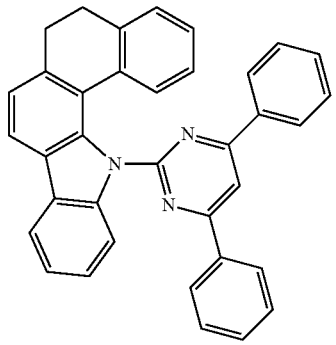
65
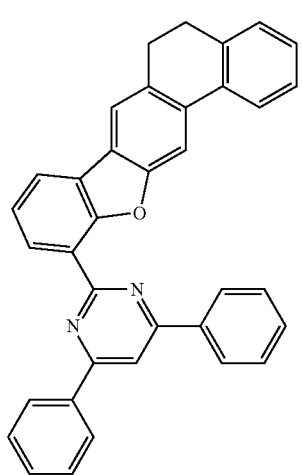
66
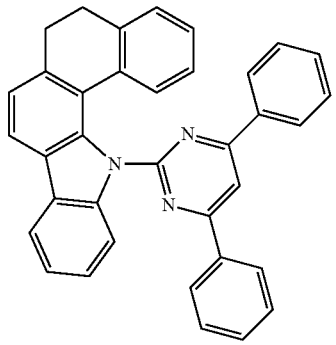
67
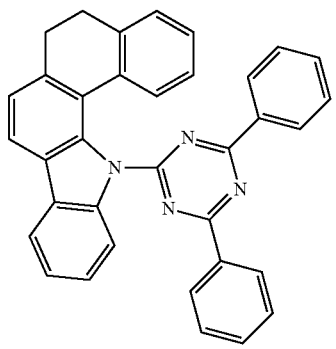
68
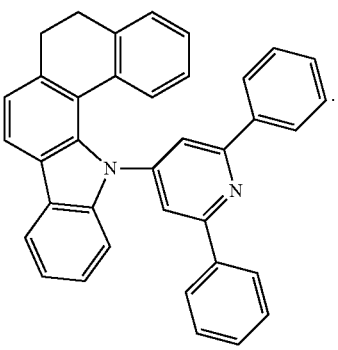
5. The material for the organic light emitting device of claim 1, wherein the compound represented by the above Chemical Formula 4 is one selected from the following chemical structures 69 to 92 of Group 2:
Group 2
[69]
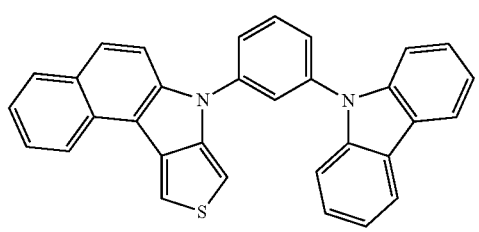

[70]
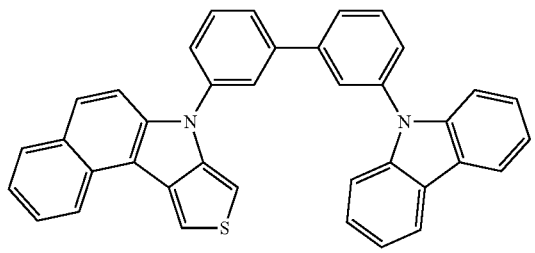
[71]
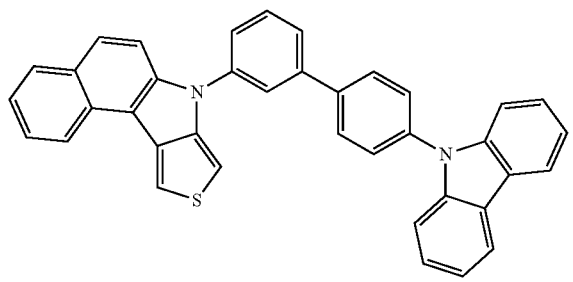
[72]
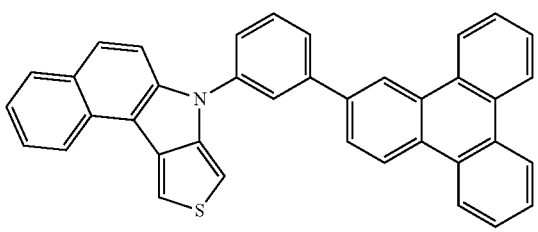
[73]
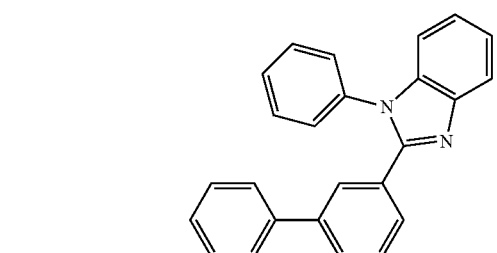
[74]
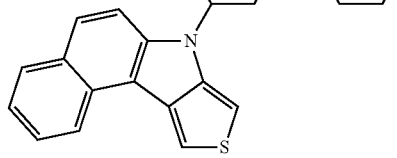
[75]
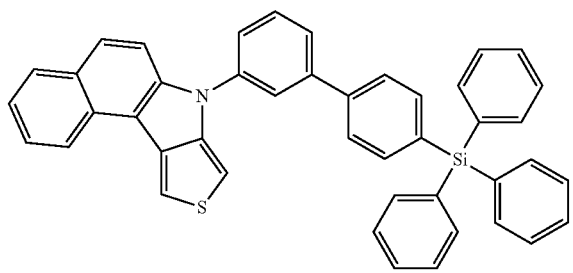
[76]
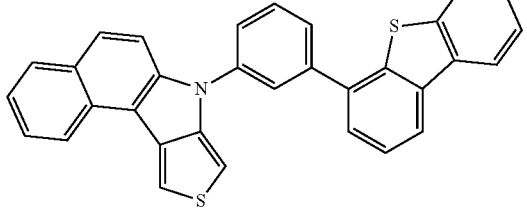
[77]
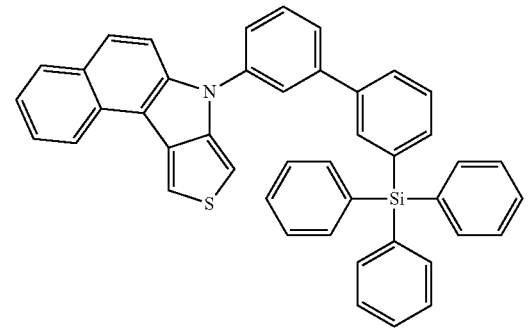
[78]
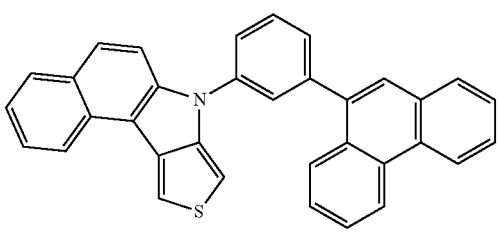
[79]
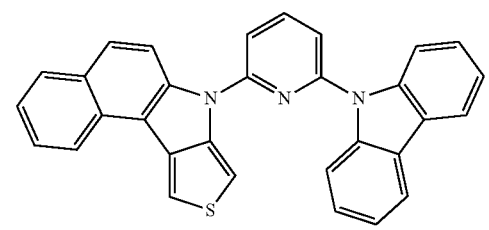

[80]
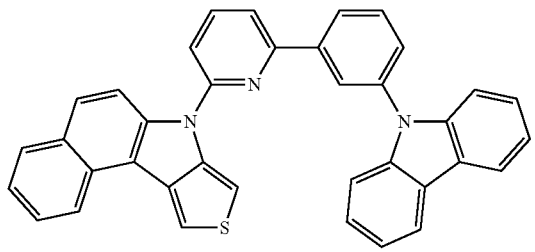
[81]
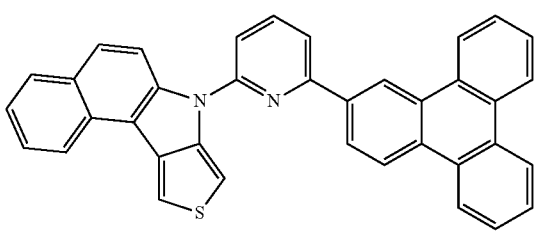
[82]
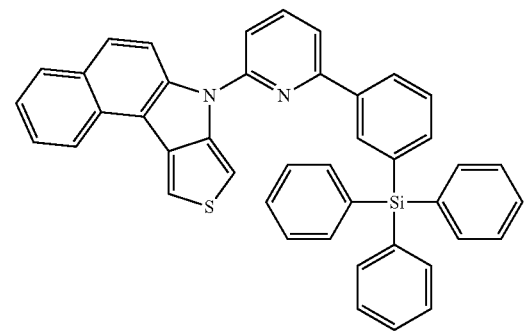
[83]
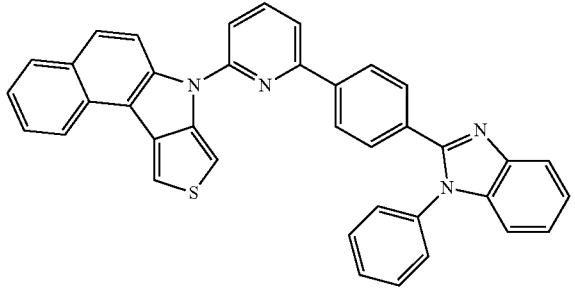
[84]
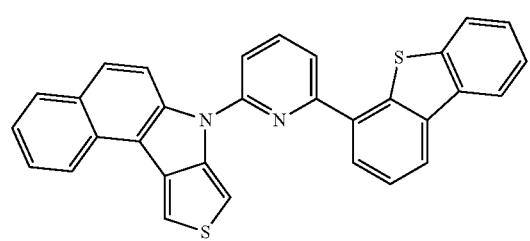
[85]
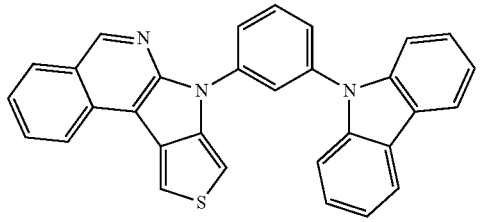
[86]
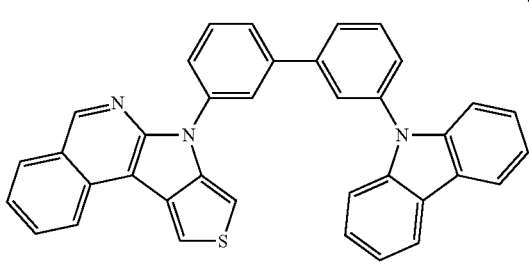
[87]
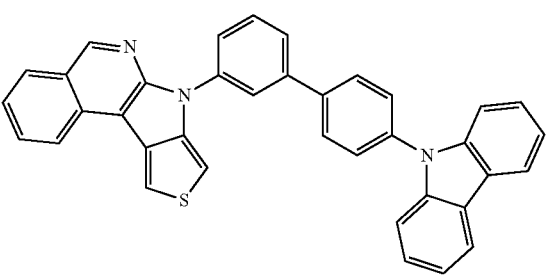
[88]
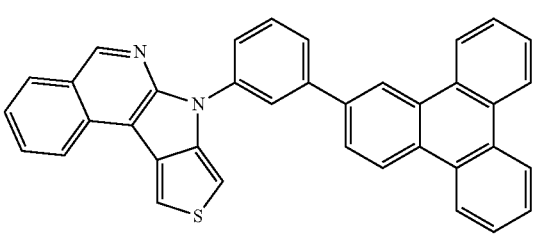

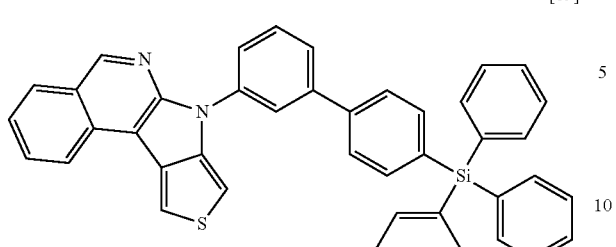

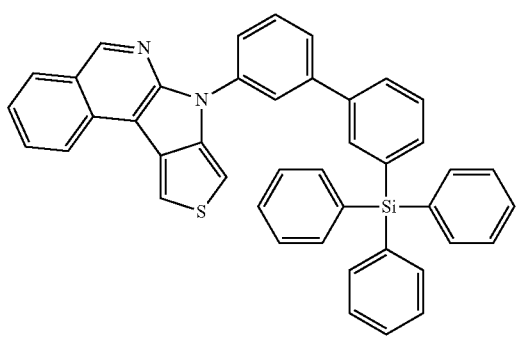

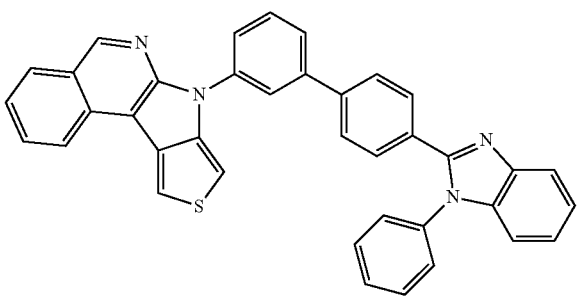

6. The material for the organic light emitting device of claim 1, wherein a weight ratio of the compound represented by one of the above Chemical Formulae 1 to 3 and the compound represented by Chemical Formula 4 is about 0.01:0.99 to about 0.99:0.01.

7. An organic light emitting device, comprising
an anode;
a cathode facing the anode; and
an organic layer between the anode and the cathode,
wherein the organic layer comprises the material for the organic light emitting device of claim 1.

8. The organic light emitting device of claim 7, wherein the organic layer is an electron injection layer (EIL), an electron transport layer (ETL), a hole injection layer (HIL), a hole transport layer (HTL), or an emission layer.

9. The organic light emitting device of claim 8, wherein the organic layer is an emission layer.

10. The organic light emitting device of claim 9, wherein the emission layer further comprises a dopant having red, green, or blue light emitting characteristics.

11. A display device comprising the organic light emitting device of claim 8.

* * * * *